US009943589B2

(12) United States Patent
Jiang et al.

(10) Patent No.: US 9,943,589 B2
(45) Date of Patent: Apr. 17, 2018

(54) IMMUNOPOTENTIATOR-LINKED OLIGOMERIC INFLUENZA IMMUNOGENIC COMPOSITIONS

(71) Applicant: New York Blood Center, Inc., New York, NY (US)

(72) Inventors: Shibo Jiang, New York, NY (US); Lanying Du, Rego Park, NY (US)

(73) Assignee: NEW YORK BLOOD CENTER, INC., New York, NY (US)

( * ) Notice: Subject to any disclaimer, the term of this patent is extended or adjusted under 35 U.S.C. 154(b) by 0 days.

(21) Appl. No.: 15/416,968

(22) Filed: Jan. 26, 2017

(65) Prior Publication Data

US 2017/0182148 A1    Jun. 29, 2017

Related U.S. Application Data

(62) Division of application No. 12/897,997, filed on Oct. 5, 2010, now Pat. No. 9,592,287.

(60) Provisional application No. 61/250,442, filed on Oct. 9, 2009.

(51) Int. Cl.
| | |
|---|---|
| *A61K 39/145* | (2006.01) |
| *C12N 7/00* | (2006.01) |
| *A61K 39/00* | (2006.01) |

(52) U.S. Cl.
CPC ............. *A61K 39/145* (2013.01); *C12N 7/00* (2013.01); *C12Y 302/01* (2013.01); *A61K 2039/6056* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 8,053,553 B2 | 11/2011 | Strongin et al. | |
| 2006/0014148 A1 | 1/2006 | Haynes et al. | |
| 2007/0042002 A1 | 2/2007 | Weeks-Levy et al. | |
| 2009/0186025 A1 | 7/2009 | Colaco | |
| 2010/0040635 A1 | 2/2010 | Horowitz et al. | |
| 2010/0098724 A1 | 4/2010 | Jiang et al. | |

FOREIGN PATENT DOCUMENTS

| | | |
|---|---|---|
| WO | 97/49423 A2 | 12/1997 |
| WO | 2007/052058 A1 | 5/2007 |
| WO | 2007/107797 | 9/2007 |
| WO | 2008/015480 A2 | 2/2008 |

OTHER PUBLICATIONS

De Filette et al. "An Influenza A Vaccine Based on Tetrameric Ectodomain of Matrix Protein 2." The Journal of Biological Chemistry, vol. 283, No. 17, pp. 11382-11387, Apr. 25, 2008.
Farzan et al. "Stabilization of Human Immunodeficiency Virus Type 1 Envelope Glycoprotein Trimers by Disulfide Bonds Introduced into the gp41 Glycoprotein Ectodomain." Journal of Virology, Sep. 1998, p. 7620-7625, vol. 72, No. 9.
Louis et al. "Design and Properties of NCCG-gp41, a Chimeric gp41 Molecule with Nanomolar HIV Fusion Inhibitory Activity." The Journal of Biological Chemistry, vol. 276, No. 31, Aug. 3, pp. 29485-29489, 2001.
Nelson et al. "Antibody Elicited Against the gp41 N-Heptad Repeat (NHR) Coiled-Coil Can Neutralize HIV-1 with Modest Potency but Non-neutralizing Antibodies Also Bind to NHR Mimetics." Virology, Jul. 20, 2008; 377(1): 170-183.
Watanabe et al. "Protection against influenza virus infection by intranasal administration of C3d-fused hemagglutinin." Vaccine 21 (2003) 4532-4538.
Yang et al. "Highly Stable Trimers Formed by Human Immunodeficiency Virus Type 1 Envelope Glycoproteins Fused with the Trimeric Motif of T4 Bacteriophage Fibritin." Journal of Virology, May 2002, p. 4634-4642, vol. 76, No. 9.
Wei et al., C"omparative efficacy of neutralizing antibodies elicited by recombinant hemagglutinin proteins from avian H5N1 influenza virus." Journal of Virology, vol. 82, No. 13, pp. 6200-6208 (2008).
Yano et al. "An ingenious design for peptide vaccines." Vaccine 23:2322-2326, 2005.
Chiu et al. "Immunological study of HA1 domain of hemagglutinin of influenza H5N1 virus." Biochem Biophys Res Comm 383:27-31, 2009.
Zoth et al. "Potential use of the hemagglutinin-neuraminidase glycoprotein of Newcastle Disease Virus expressed in *Rachiplusia nu* larvae as an immunogen for chickens." Clin Vaccine Immunol 16:775-778, 2009.
Song et al. "Efficacious recombinant influenza vaccines produced by high yield bacterial expression: a solution to global pandemic and seasonal needs." PLoS One. 3:e2257, 2008.
Li et al. "A recombinant protein containing highly conserved hemagglutinin residues 81-122 of influenza H5N1 induces strong humoral and mucosal immune responses." BioScience Trends 7:139-137, 2013.
Du et al. "A critical HA1 neutralizing domain of H5N1 influenza in an optimal conformation induces strong cross-protection." PLoS One 8:e53568, 2013.
Khurana et al. "Bacterial HA1 vaccine against pandemic H5N1 influenza virus: evidence of oligomerization, hemagglutination, and cross-protective immunity in ferrets." J Virol 85:1246-1256, 2011.
Du et al. "Identification and structural characterization of a broadly neutralizing antibody targeting a novel conserved epitope on the influenza virus H5N1 hemagglutinin." J Viral 87:2215, 2013.
Du et al. "A recombinant vaccine of H5N1 HA1 fused with foldon and human IgG Fc induced complete cross-clade protection against divergent H5N1 viruses." PLoS One 6:e16555, 2011.

(Continued)

*Primary Examiner* — Benjamin P Blumel
(74) *Attorney, Agent, or Firm* — K&L Gates LLP; Louis C. Cullman; David Diamond

(57) ABSTRACT

Disclosed herein are immunogenic compositions for preventing infection with influenza viruses wherein the immunogenic compositions comprises an immunogen such as a hemagglutinin of an influenza virus, and an immunopotentiator such as an Fc fragment of human IgG and optionally a stabilization sequence. The immunogen is linked to the stabilization sequence which in turn is linked to the immunopotentiator.

8 Claims, 24 Drawing Sheets

(56) References Cited

OTHER PUBLICATIONS

Alvarez et al., "A new expression system for protein crystalization using trimeric coiled-coil adaptors", 2008, Protein Engineering, Design and Selection, vol. 21, No. 1, pp. 11-18.

Ando et al., Preparation of influenza virosome vaccine with muramyldipeptide derivative B30-MDP, 1997, Journal of Microencapsulation, vol. 14, No. 1, pp. 79-90.

He et al., Recombinant Ov-ASP-1, a Th1-Biased Protein Adjuvant Derived from the Helminth Onchocerca volvulus, Can Directly Bind and Activate Antigen-Presenting Cells, 2009, Journal of Immunology, vol. 182, pates 4005-4016.

Ma et al., Carcinoembryonic antigen-immunoglobulin Fc fusion protein (CEA-Fc) for identification and activation of anti-CEA immunoglobulin-T-Cell receptor-modified T Cells, representative of a new class of Ig fusion proteins, 2004, Cancer Gene Therapy, vol. 11, pp. 297-306.

Xiao et al., Evaluation of recombinant Onchocerca volvulus activation associated protein-1 (ASP-1) as a potent Th1-biased adjuvant with a panel of protein or peptide-based antigens and commercial inacivated vaccines, 2008, Vaccine, vol. 26, pp. 5022-5029.

Cai, et al. "A novel fluorescence intensity screening assay identifies new low-molecular-weight inhibitors of the gp41 coiled-coil domain of human immunodeficiency virus type 1." Antimicrob Agents Chemother 51:2388, 2007.

Connor "Scientists create new flu vaccine that works against many different strains of the virus." The Independent May 22, 2013.

FIG. 16

Neutralizing Ab titers vs H5N1 pseudoviruses (HK-HA, 1194-HA, QH-HA, XJ-HA, AH-HA) for HA1-hFc, HA1-Fd-hFc, and PBS.

FIG. 17

SEQUENCE LISTING

```
<160> NUMBER OF SEQ ID NOS: 48

<210> SEQ ID NO 1
<211> LENGTH: 567
<212> TYPE: PRT
<213> ORGANISM: Influenza virus

<400> SEQUENCE: 1

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
```

```
            115                 120                 125
Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Asn Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Val Lys Ser Glu Val Glu Tyr Gly
            275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Arg Arg Lys Arg Gly Leu Phe Gly Ala Ile Ala
            340                 345                 350

Gly Phe Ile Glu Gly Gly Trp Gln Gly Met Val Asp Gly Trp Tyr Gly
            355                 360                 365

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
            435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
            515                 520                 525

Tyr Gln Ile Leu Ser Ile Tyr Ser Thr Val Ala Ser Ser Leu Ala Leu
    530                 535                 540
```

```
Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 2
<211> LENGTH: 320
<212> TYPE: PRT
<213> ORGANISM: Influenza virus

<400> SEQUENCE: 2

Ile Cys Ile Gly Tyr His Ala Asn Asn Ser Thr Glu Gln Val Asp Thr
1               5                   10                  15

Ile Met Glu Lys Asn Val Thr Val Thr His Ala Gln Asp Ile Leu Glu
            20                  25                  30

Lys Thr His Asn Gly Lys Leu Cys Asp Leu Asp Gly Val Lys Pro Leu
        35                  40                  45

Ile Leu Arg Asp Cys Ser Val Ala Gly Trp Leu Leu Gly Asn Pro Met
    50                  55                  60

Cys Asp Glu Phe Ile Asn Val Pro Glu Trp Ser Tyr Ile Val Glu Lys
65                  70                  75                  80

Ala Asn Pro Ala Asn Asp Leu Cys Tyr Pro Gly Asn Phe Asn Asp Tyr
                85                  90                  95

Glu Glu Leu Lys His Leu Leu Ser Arg Ile Asn His Phe Glu Lys Ile
            100                 105                 110

Gln Ile Ile Pro Lys Ser Ser Trp Ser Asp His Glu Ala Ser Ser Gly
        115                 120                 125

Val Ser Ser Ala Cys Pro Tyr Gln Gly Thr Pro Ser Phe Phe Arg Asn
    130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
            180                 185                 190

Thr Thr Tyr Ile Ser Val Gly Thr Ser Thr Leu Asn Gln Arg Leu Val
        195                 200                 205

Pro Lys Ile Ala Thr Arg Ser Lys Val Asn Gly Gln Asn Gly Arg Met
    210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys Gly Asp Ser Ala Ile Val Lys Ser Glu Val Glu Tyr Gly Asn Cys
            260                 265                 270

Asn Thr Lys Cys Gln Thr Pro Ile Gly Ala Ile Asn Ser Ser Met Pro
        275                 280                 285

Phe His Asn Ile His Pro Leu Thr Ile Gly Glu Cys Pro Lys Tyr Val
    290                 295                 300

Lys Ser Asn Lys Leu Val Leu Ala Thr Gly Leu Arg Asn Ser Pro Leu
305                 310                 315                 320

<210> SEQ ID NO 3
<211> LENGTH: 222
<212> TYPE: PRT
```

-continued

```
<213> ORGANISM: Influenza virus

<400> SEQUENCE: 3

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
            20                  25                  30

Gly Tyr Ala Ala Asp Lys Glu Ser Thr Gln Lys Ala Ile Asp Gly Val
        35                  40                  45

Thr Asn Lys Val Asn Ser Ile Ile Asp Lys Met Asn Thr Gln Phe Glu
    50                  55                  60

Ala Val Gly Arg Glu Phe Asn Asn Leu Glu Arg Arg Ile Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Tyr Asp Lys Val Arg Leu Gln Leu Arg Asp
        115                 120                 125

Asn Ala Lys Glu Leu Gly Asn Gly Cys Phe Glu Phe Tyr His Lys Cys
    130                 135                 140

Asp Asn Glu Cys Met Glu Ser Val Arg Asn Gly Thr Tyr Asp Tyr Pro
145                 150                 155                 160

Gln Tyr Ser Glu Glu Ala Arg Leu Lys Arg Glu Glu Ile Ser Gly Val
                165                 170                 175

Lys Leu Glu Ser Ile Gly Thr Tyr Gln Ile Leu Ser Ile Tyr Ser Thr
            180                 185                 190

Val Ala Ser Ser Leu Ala Leu Ala Ile Met Val Ala Gly Leu Ser Leu
        195                 200                 205

Trp Met Cys Ser Asn Gly Ser Leu Gln Cys Arg Ile Cys Ile
    210                 215                 220

<210> SEQ ID NO 4
<211> LENGTH: 155
<212> TYPE: PRT
<213> ORGANISM: Influenza virus

<400> SEQUENCE: 4

Leu Ser Arg Ile Asn His Phe Glu Lys Ile Gln Ile Ile Pro Lys Ser
1               5                   10                  15

Ser Trp Ser Asp His Glu Ala Ser Ser Gly Val Ser Ser Ala Cys Pro
            20                  25                  30

Tyr Gln Gly Thr Pro Ser Phe Phe Arg Asn Val Val Trp Leu Ile Lys
        35                  40                  45

Lys Asn Asn Thr Tyr Pro Thr Ile Lys Arg Ser Tyr Asn Asn Thr Asn
    50                  55                  60

Gln Glu Asp Leu Leu Ile Leu Trp Gly Ile His His Ser Asn Asp Ala
65                  70                  75                  80

Ala Glu Gln Thr Lys Leu Tyr Gln Asn Pro Thr Thr Tyr Ile Ser Val
                85                  90                  95

Gly Thr Ser Thr Leu Asn Gln Arg Leu Val Pro Lys Ile Ala Thr Arg
            100                 105                 110

Ser Lys Val Asn Gly Gln Asn Gly Arg Met Asp Phe Phe Trp Thr Ile
        115                 120                 125

Leu Lys Pro Asn Asp Ala Ile Asn Phe Glu Ser Asn Gly Asn Phe Ile
```

```
                130                 135                 140
Ala Pro Glu Tyr Ala Tyr Lys Ile Val Lys Lys
145                 150                 155

<210> SEQ ID NO 5
<211> LENGTH: 20
<212> TYPE: PRT
<213> ORGANISM: Artificial Sequence
<220> FEATURE:
<223> OTHER INFORMATION: Interleukin 2 signal sequence

<400> SEQUENCE: 5

Met Tyr Arg Met Gln Leu Leu Ser Cys Ile Ala Leu Ser Leu Ala Leu
1               5                   10                  15

Val Thr Asn Ser
            20

<210> SEQ ID NO 6
<211> LENGTH: 27
<212> TYPE: PRT
<213> ORGANISM: Bacteriophage T4

<400> SEQUENCE: 6

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 7
<211> LENGTH: 229
<212> TYPE: PRT
<213> ORGANISM: Homo sapiens

<400> SEQUENCE: 7

Arg Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190
```

```
Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
    210                 215                 220

Leu Ser Pro Gly Lys
225

<210> SEQ ID NO 8
<211> LENGTH: 594
<212> TYPE: PRT
<213> ORGANISM: Artificial Sequence
<220> FEATURE:
<223> OTHER INFORMATION: HA-Fd fusion protein

<400> SEQUENCE: 8

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Asn Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Val Lys Ser Glu Val Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320
```

```
Tyr Val Lys Ser Asn Lys Leu Val Leu Ala Thr Gly Leu Arg Asn Ser
            325                 330                 335

Pro Leu Arg Glu Arg Arg Lys Arg Gly Leu Phe Gly Ala Ile Ala
        340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
        370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro G

-continued

```
                85                  90                  95

Glu Glu Leu Lys His Leu Leu Ser Arg Ile Asn His Phe Glu Lys Ile
            100                 105                 110

Gln Ile Ile Pro Lys Ser Ser Trp Ser Asp His Glu Ala Ser Ser Gly
        115                 120                 125

Val Ser Ser Ala Cys Pro Tyr Gln Gly Thr Pro Ser Phe Phe Arg Asn
    130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
            180                 185                 190

Thr Thr Tyr Ile Ser Val Gly Thr Ser Thr Leu Asn Gln Arg Leu Val
        195                 200                 205

Pro Lys Ile Ala Thr Arg Ser Lys Val Asn Gly Gln Asn Gly Arg Met
    210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys Gly Asp Ser Ala Ile Val Lys Ser Glu Val Glu Tyr Gly Asn Cys
            260                 265                 270

Asn Thr Lys Cys Gln Thr Pro Ile Gly Ala Ile Asn Ser Ser Met Pro
        275                 280                 285

Phe His Asn Ile His Pro Leu Thr Ile Gly Glu Cys Pro Lys Tyr Val
    290                 295                 300

Lys Ser Asn Lys Leu Val Leu Ala Thr Gly Leu Arg Asn Ser Pro Leu
305                 310                 315                 320

Gly Tyr Ile Pro Glu Ala Pro Arg Asp Gly Gln Ala Tyr Val Arg Lys
                325                 330                 335

Asp Gly Glu Trp Val Leu Leu Ser Thr Phe Leu
            340                 345

<210> SEQ ID NO 10
<211> LENGTH: 249
<212> TYPE: PRT
<213> ORGANISM: Artificial Sequence
<220> FEATURE:
<223> OTHER INFORMATION: HA2-Fd fusion protein

<400> SEQUENCE: 10

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
            20                  25                  30

Gly Tyr Ala Ala Asp Lys Glu Ser Thr Gln Lys Ala Ile Asp Gly Val
        35                  40                  45

Thr Asn Lys Val Asn Ser Ile Ile Asp Lys Met Asn Thr Gln Phe Glu
    50                  55                  60

Ala Val Gly Arg Glu Phe Asn Asn Leu Glu Arg Arg Ile Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
```

```
                        100                 105                 110
Ser Asn Val Lys Asn Leu Tyr Asp Lys Val Arg Leu Gln Leu Arg Asp
            115                 120                 125

Asn Ala Lys Glu Leu Gly Asn Gly Cys Phe Glu Phe Tyr His Lys Cys
        130                 135                 140

Asp Asn Glu Cys Met Glu Ser Val Arg Asn Gly Thr Tyr Asp Tyr Pro
145                 150                 155                 160

Gln Tyr Ser Glu Glu Ala Arg Leu Lys Arg Glu Glu Ile Ser Gly Val
                165                 170                 175

Lys Leu Glu Ser Ile Gly Thr Tyr Gln Ile Leu Ser Ile Tyr Ser Thr
            180                 185                 190

Val Ala Ser Ser Leu Ala Leu Ala Ile Met Val Ala Gly Leu Ser Leu
        195                 200                 205

Trp Met Cys Ser Asn Gly Ser Leu Gln Cys Arg Ile Cys Ile Gly Tyr
    210                 215                 220

Ile Pro Glu Ala Pro Arg Asp Gly Gln Ala Tyr Val Arg Lys Asp Gly
225                 230                 235                 240

Glu Trp Val Leu Leu Ser Thr Phe Leu
                245

<210> SEQ ID NO 11
<211> LENGTH: 182
<212> TYPE: PRT
<213> ORGANISM: Artificial Sequence
<220> FEATURE:
<223> OTHER INFORMATION: HA-RBD-Fd fusion protein

<400> SEQUENCE: 11

Leu Ser Arg Ile Asn His Phe Glu Lys Ile Gln Ile Ile Pro Lys Ser
1               5                   10                  15

Ser Trp Ser Asp His Glu Ala Ser Ser Gly Val Ser Ser Ala Cys Pro
            20                  25                  30

Tyr Gln Gly Thr Pro Ser Phe Phe Arg Asn Val Val Trp Leu Ile Lys
        35                  40                  45

Lys Asn Asn Thr Tyr Pro Thr Ile Lys Arg Ser Tyr Asn Asn Thr Asn
    50                  55                  60

Gln Glu Asp Leu Leu Ile Leu Trp Gly Ile His His Ser Asn Asp Ala
65                  70                  75                  80

Ala Glu Gln Thr Lys Leu Tyr Gln Asn Pro Thr Thr Tyr Ile Ser Val
                85                  90                  95

Gly Thr Ser Thr Leu Asn Gln Arg Leu Val Pro Lys Ile Ala Thr Arg
            100                 105                 110

Ser Lys Val Asn Gly Gln Asn Gly Arg Met Asp Phe Phe Trp Thr Ile
        115                 120                 125

Leu Lys Pro Asn Asp Ala Ile Asn Phe Glu Ser Asn Gly Asn Phe Ile
    130                 135                 140

Ala Pro Glu Tyr Ala Tyr Lys Ile Val Lys Lys Gly Tyr Ile Pro Glu
145                 150                 155                 160

Ala Pro Arg Asp Gly Gln Ala Tyr Val Arg Lys Asp Gly Glu Trp Val
                165                 170                 175

Leu Leu Ser Thr Phe Leu
            180

<210> SEQ ID NO 12
<211> LENGTH: 796
<212> TYPE: PRT
```

<213> ORGANISM: Artificial Sequence
<220> FEATURE:
<223> OTHER INFORMATION: HA-hFc fusion protein

<400> SEQUENCE: 12

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Asn Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Val Lys Ser Glu Val Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Arg Arg Lys Arg Gly Leu Phe Gly Ala Ile Ala
            340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
```

385                 390                 395                 400

Ile Asp Lys Met Asn Thr Gln Phe Glu Ala Val Gly Arg Glu Phe Asn
                    405                 410                 415

Asn Leu Glu Arg Arg Ile Glu Asn Leu Asn Lys Lys Met Glu Asp Gly
                420                 425                 430

Phe Leu Asp Val Trp Thr Tyr Asn Ala Glu Leu Leu Val Leu Met Glu
            435                 440                 445

Asn Glu Arg Thr Leu Asp Phe His Asp Ser Asn Val Lys Asn Leu Tyr
        450                 455                 460

Asp Lys Val Arg Leu Gln Leu Arg Asp Asn Ala Lys Glu Leu Gly Asn
    465                 470                 475                 480

Gly Cys Phe Glu Phe Tyr His Lys Cys Asp Asn Glu Cys Met Glu Ser
                    485                 490                 495

Val Arg Asn Gly Thr Tyr Asp Tyr Pro Gln Tyr Ser Glu Glu Ala Arg
                500                 505                 510

Leu Lys Arg Glu Glu Ile Ser Gly Val Lys Leu Glu Ser Ile Gly Thr
            515                 520                 525

Tyr Gln Ile Leu Ser Ile Tyr Ser Thr Val Ala Ser Leu Ala Leu
        530                 535                 540

Ala Ile Met Val Ala Gly Leu Ser Leu Trp Met Cys Ser Asn Gly Ser
    545                 550                 555                 560

Leu Gln Cys Arg Ile Cys Ile Arg Ser Asp Lys Thr His Thr Cys Pro
                    565                 570                 575

Pro Cys Pro Ala Pro Glu Leu Leu Gly Gly Pro Ser Val Phe Leu Phe
                580                 585                 590

Pro Pro Lys Pro Lys Asp Thr Leu Met Ile Ser Arg Thr Pro Glu Val
            595                 600                 605

Thr Cys Val Val Val Asp Val Ser His Glu Asp Pro Glu Val Lys Phe
        610                 615                 620

Asn Trp Tyr Val Asp Gly Val Glu Val His Asn Ala Lys Thr Lys Pro
    625                 630                 635                 640

Arg Glu Glu Gln Tyr Asn Ser Thr Tyr Arg Val Val Ser Val Leu Thr
                    645                 650                 655

Val Leu His Gln Asp Trp Leu Asn Gly Lys Glu Tyr Lys Cys Lys Val
                660                 665                 670

Ser Asn Lys Ala Leu Pro Ala Pro Ile Glu Lys Thr Ile Ser Lys Ala
            675                 680                 685

Lys Gly Gln Pro Arg Glu Pro Gln Val Tyr Thr Leu Pro Pro Ser Arg
        690                 695                 700

Glu Glu Met Thr Lys Asn Gln Val Ser Leu Thr Cys Leu Val Lys Gly
    705                 710                 715                 720

Phe Tyr Pro Ser Asp Ile Ala Val Glu Trp Glu Ser Asn Gly Gln Pro
                    725                 730                 735

Glu Asn Asn Tyr Lys Thr Thr Pro Pro Val Leu Asp Ser Asp Gly Ser
                740                 745                 750

Phe Phe Leu Tyr Ser Lys Leu Thr Val Asp Lys Ser Arg Trp Gln Gln
            755                 760                 765

Gly Asn Val Phe Ser Cys Ser Val Met His Glu Ala Leu His Asn His
        770                 775                 780

Tyr Thr Gln Lys Ser Leu Ser Leu Ser Pro Gly Lys
    785                 790                 795

<210> SEQ ID NO 13

-continued

<211> LENGTH: 549
<212> TYPE: PRT
<213> ORGANISM: Artificial Sequence
<220> FEATURE:
<223> OTHER INFORMATION: HA1-hFc fusion protein

<400> SEQUENCE: 13

```
Ile Cys Ile Gly Tyr His Ala Asn Asn Ser Thr Glu Gln Val Asp Thr
1               5                   10                  15

Ile Met Glu Lys Asn Val Thr Val Thr His Ala Gln Asp Ile Leu Glu
            20                  25                  30

Lys Thr His Asn Gly Lys Leu Cys Asp Leu Asp Gly Val Lys Pro Leu
        35                  40                  45

Ile Leu Arg Asp Cys Ser Val Ala Gly Trp Leu Leu Gly Asn Pro Met
    50                  55                  60

Cys Asp Glu Phe Ile Asn Val Pro Glu Trp Ser Tyr Ile Val Glu Lys
65                  70                  75                  80

Ala Asn Pro Ala Asn Asp Leu Cys Tyr Pro Gly Asn Phe Asn Asp Tyr
                85                  90                  95

Glu Glu Leu Lys His Leu Leu Ser Arg Ile Asn His Phe Glu Lys Ile
            100                 105                 110

Gln Ile Ile Pro Lys Ser Ser Trp Ser Asp His Glu Ala Ser Ser Gly
        115                 120                 125

Val Ser Ser Ala Cys Pro Tyr Gln Gly Thr Pro Ser Phe Phe Arg Asn
    130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
            180                 185                 190

Thr Thr Tyr Ile Ser Val Gly Thr Ser Thr Leu Asn Gln Arg Leu Val
        195                 200                 205

Pro Lys Ile Ala Thr Arg Ser Lys Val Asn Gly Gln Asn Gly Arg Met
    210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys Gly Asp Ser Ala Ile Val Lys Ser Glu Val Glu Tyr Gly Asn Cys
            260                 265                 270

Asn Thr Lys Cys Gln Thr Pro Ile Gly Ala Ile Asn Ser Ser Met Pro
        275                 280                 285

Phe His Asn Ile His Pro Leu Thr Ile Gly Glu Cys Pro Lys Tyr Val
    290                 295                 300

Lys Ser Asn Lys Leu Val Leu Ala Thr Gly Leu Arg Asn Ser Pro Leu
305                 310                 315                 320

Arg Ser Asp Lys Thr His Thr Cys Pro Pro Cys Pro Ala Pro Glu Leu
                325                 330                 335

Leu Gly Gly Pro Ser Val Phe Leu Phe Pro Pro Lys Pro Lys Asp Thr
            340                 345                 350

Leu Met Ile Ser Arg Thr Pro Glu Val Thr Cys Val Val Val Asp Val
        355                 360                 365

Ser His Glu Asp Pro Glu Val Lys Phe Asn Trp Tyr Val Asp Gly Val
    370                 375                 380
```

```
Glu Val His Asn Ala Lys Thr Lys Pro Arg Glu Glu Gln Tyr Asn Ser
385                 390                 395                 400

Thr Tyr Arg Val Val Ser Val Leu Thr Val Leu His Gln Asp Trp Leu
                405                 410                 415

Asn Gly Lys Glu Tyr Lys Cys Lys Val Ser Asn Lys Ala Leu Pro Ala
            420                 425                 430

Pro Ile Glu Lys Thr Ile Ser Lys Ala Lys Gly Gln Pro Arg Glu Pro
            435                 440                 445

Gln Val Tyr Thr Leu Pro Pro Ser Arg Glu Glu Met Thr Lys Asn Gln
    450                 455                 460

Val Ser Leu Thr Cys Leu Val Lys Gly Phe Tyr Pro Ser Asp Ile Ala
465                 470                 475                 480

Val Glu Trp Glu Ser Asn Gly Gln Pro Glu Asn Asn Tyr Lys Thr Thr
                485                 490                 495

Pro Pro Val Leu Asp Ser Asp Gly Ser Phe Phe Leu Tyr Ser Lys Leu
            500                 505                 510

Thr Val Asp Lys Ser Arg Trp Gln Gln Gly Asn Val Phe Ser Cys Ser
            515                 520                 525

Val Met His Glu Ala Leu His Asn His Tyr Thr Gln Lys Ser Leu Ser
    530                 535                 540

Leu Ser Pro Gly Lys
545

<210> SEQ ID NO 14
<211> LENGTH: 451
<212> TYPE: PRT
<213> ORGANISM: Artificial Sequence
<220> FEATURE:
<223> OTHER INFORMATION: HA2-hFc fusion protein

<400> SEQUENCE: 14

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
                20                  25                  30

Gly Tyr Ala Ala Asp Lys Glu Ser Thr Gln Lys Ala Ile Asp Gly Val
            35                  40                  45

Thr Asn Lys Val Asn Ser Ile Ile Asp Lys Met Asn Thr Gln Phe Glu
        50                  55                  60

Ala Val Gly Arg Glu Phe Asn Asn Leu Glu Arg Arg Ile Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
                100                 105                 110

Ser Asn Val Lys Asn Leu Tyr Asp Lys Val Arg Leu Gln Leu Arg Asp
            115                 120                 125

Asn Ala Lys Glu Leu Gly Asn Gly Cys Phe Glu Phe Tyr His Lys Cys
130                 135                 140

Asp Asn Glu Cys Met Glu Ser Val Arg Asn Gly Thr Tyr Asp Tyr Pro
145                 150                 155                 160

Gln Tyr Ser Glu Glu Ala Arg Leu Lys Arg Glu Glu Ile Ser Gly Val
                165                 170                 175

Lys Leu Glu Ser Ile Gly Thr Tyr Gln Ile Leu Ser Ile Tyr Ser Thr
            180                 185                 190
```

-continued

```
Val Ala Ser Ser Leu Ala Leu Ala Ile Met Val Ala Gly Leu Ser Leu
        195                 200                 205

Trp Met Cys Ser Asn Gly Ser Leu Gln Cys Arg Ile Cys Ile Arg Ser
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 15
<211> LENGTH: 384
<212> TYPE: PRT
<213> ORGANISM: Artificial Sequence
<220> FEATURE:
<223> OTHER INFORMATION: HA-RBD-hFc fusion protein

<400> SEQUENCE: 15

Leu Ser Arg Ile Asn His Phe Glu Lys Ile Gln Ile Ile Pro Lys Ser
1               5                   10                  15

Ser Trp Ser Asp His Glu Ala Ser Ser Gly Val Ser Ser Ala Cys Pro
            20                  25                  30

Tyr Gln Gly Thr Pro Ser Phe Phe Arg Asn Val Val Trp Leu Ile Lys
        35                  40                  45

Lys Asn Asn Thr Tyr Pro Thr Ile Lys Arg Ser Tyr Asn Asn Thr Asn
    50                  55                  60

Gln Glu Asp Leu Leu Ile Leu Trp Gly Ile His His Ser Asn Asp Ala
65                  70                  75                  80

Ala Glu Gln Thr Lys Leu Tyr Gln Asn Pro Thr Thr Tyr Ile Ser Val
                85                  90                  95
```

Gly Thr Ser Thr Leu Asn Gln Arg Leu Val Pro Lys Ile Ala Thr Arg
            100                 105                 110

Ser Lys Val Asn Gly Gln Asn Gly Arg Met Asp Phe Phe Trp Thr Ile
            115                 120                 125

Leu Lys Pro Asn Asp Ala Ile Asn Phe Glu Ser Asn Gly Asn Phe Ile
            130                 135                 140

Ala Pro Glu Tyr Ala Tyr Lys Ile Val Lys Lys Arg Ser Asp Lys Thr
145                 150                 155                 160

His Thr Cys Pro Pro Cys Pro Ala Pro Glu Leu Leu Gly Gly Pro Ser
                165                 170                 175

Val Phe Leu Phe Pro Pro Lys Pro Lys Asp Thr Leu Met Ile Ser Arg
                180                 185                 190

Thr Pro Glu Val Thr Cys Val Val Val Asp Val Ser His Glu Asp Pro
            195                 200                 205

Glu Val Lys Phe Asn Trp Tyr Val Asp Gly Val Glu Val His Asn Ala
210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Glu Glu Met Thr Lys Asn Gln Val Ser Leu Thr Cys
290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
    370                 375                 380

<210> SEQ ID NO 16
<211> LENGTH: 823
<212> TYPE: PRT
<213> ORGANISM: Artificial Sequence
<220> FEATURE:
<223> OTHER INFORMATION: HA-Fd-hFc fusion protein

<400> SEQUENCE: 16

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

```
Pro Met Cys Asp Glu Phe Ile Asn Val Pro Glu Trp Ser Tyr Ile Val
             85                  90                  95
Glu Lys Ala Asn Pro Ala Asn Asp Leu Cys Tyr Pro Gly Asn Phe Asn
                 100                 105                 110
Asp Tyr Glu Glu Leu Lys His Leu Leu Ser Arg Ile Asn His Phe Glu
             115                 120                 125
Lys Ile Gln Ile Ile Pro Lys Ser Ser Trp Ser Asp His Glu Ala Ser
     130                 135                 140
Ser Gly Val Ser Ser Ala Cys Pro Tyr Gln Gly Thr Pro Ser Phe Phe
145                 150                 155                 160
Arg Asn Val Val Trp Leu Ile Lys Lys Asn Asn Thr Tyr Pro Thr Ile
                 165                 170                 175
Lys Arg Ser Tyr Asn Asn Thr Asn Gln Glu Asp Leu Leu Ile Leu Trp
             180                 185                 190
Gly Ile His His Ser Asn Asp Ala Ala Glu Gln Thr Lys Leu Tyr Gln
             195                 200                 205
Asn Pro Thr Thr Tyr Ile Ser Val Gly Thr Ser Thr Leu Asn Gln Arg
     210                 215                 220
Leu Val Pro Lys Ile Ala Thr Arg Ser Lys Val Asn Gly Gln Asn Gly
225                 230                 235                 240
Arg Met Asp Phe Phe Trp Thr Ile Leu Lys Pro Asn Asp Ala Ile Asn
                 245                 250                 255
Phe Glu Ser Asn Gly Asn Phe Ile Ala Pro Glu Tyr Ala Tyr Lys Ile
             260                 265                 270
Val Lys Lys Gly Asp Ser Ala Ile Val Lys Ser Glu Val Glu Tyr Gly
             275                 280                 285
Asn Cys Asn Thr Lys Cys Gln Thr Pro Ile Gly Ala Ile Asn Ser Ser
     290                 295                 300
Met Pro Phe His Asn Ile His Pro Leu Thr Ile Gly Glu Cys Pro Lys
305                 310                 315                 320
Tyr Val Lys Ser Asn Lys Leu Val Leu Ala Thr Gly Leu Arg Asn Ser
                 325                 330                 335
Pro Leu Arg Glu Arg Arg Arg Lys Arg Gly Leu Phe Gly Ala Ile Ala
             340                 345                 350
Gly Phe Ile Glu Gly Gly Trp Gln Gly Met Val Asp Gly Trp Tyr Gly
             355                 360                 365
Tyr His His Ser Asn Glu Gln Gly Ser Gly Tyr Ala Ala Asp Lys Glu
     370                 375                 380
Ser Thr Gln Lys Ala Ile Asp Gly Val Thr Asn Lys Val Asn Ser Ile
385                 390                 395                 400
Ile Asp Lys Met Asn Thr Gln Phe Glu Ala Val Gly Arg Glu Phe Asn
                 405                 410                 415
Asn Leu Glu Arg Arg Ile Glu Asn Leu Asn Lys Lys Met Glu Asp Gly
             420                 425                 430
Phe Leu Asp Val Trp Thr Tyr Asn Ala Glu Leu Leu Val Leu Met Glu
             435                 440                 445
Asn Glu Arg Thr Leu Asp Phe His Asp Ser Asn Val Lys Asn Leu Tyr
     450                 455                 460
Asp Lys Val Arg Leu Gln Leu Arg Asp Asn Ala Lys Glu Leu Gly Asn
465                 470                 475                 480
Gly Cys Phe Glu Phe Tyr His Lys Cys Asp Asn Glu Cys Met Glu Ser
                 485                 490                 495
```

```
Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
        515                 520                 525

Tyr Gln Ile Leu Ser Ile Tyr Ser Thr Val Ala Ser Ser Leu Ala Leu
    530                 535                 540

Ala Ile Met Val Ala Gly Leu Ser Leu Trp Met Cys Ser Asn Gly Ser
545                 550                 555                 560

Leu Gln Cys Arg Ile Cys Ile Gly Tyr Ile Pro Glu Ala Pro Arg Asp
                565                 570                 575

Gly Gln Ala Tyr Val Arg Lys Asp Gly Glu Trp Val Leu Leu Ser Thr
                580                 585                 590

Phe Leu Arg Ser Asp Lys Thr His Thr Cys Pro Pro Cys Pro Ala Pro
                595                 600                 605

Glu Leu Leu Gly Gly Pro Ser Val Phe Leu Phe Pro Pro Lys Pro Lys
            610                 615                 620

Asp Thr Leu Met Ile Ser Arg Thr Pro Glu Val Thr Cys Val Val Val
625                 630                 635                 640

Asp Val Ser His Glu Asp Pro Glu Val Lys Phe Asn Trp Tyr Val Asp
                645                 650                 655

Gly Val Glu Val His Asn Ala Lys Thr Lys Pro Arg Glu Glu Gln Tyr
                660                 665                 670

Asn Ser Thr Tyr Arg Val Val Ser Val Leu Thr Val Leu His Gln Asp
                675                 680                 685

Trp Leu Asn Gly Lys Glu Tyr Lys Cys Lys Val Ser Asn Lys Ala Leu
690                 695                 700

Pro Ala Pro Ile Glu Lys Thr Ile Ser Lys Ala Lys Gly Gln Pro Arg
705                 710                 715                 720

Glu Pro Gln Val Tyr Thr Leu Pro Pro Ser Arg Glu Glu Met Thr Lys
                725                 730                 735

Asn Gln Val Ser Leu Thr Cys Leu Val Lys Gly Phe Tyr Pro Ser Asp
                740                 745                 750

Ile Ala Val Glu Trp Glu Ser Asn Gly Gln Pro Glu Asn Asn Tyr Lys
            755                 760                 765

Thr Thr Pro Pro Val Leu Asp Ser Asp Gly Ser Phe Phe Leu Tyr Ser
770                 775                 780

Lys Leu Thr Val Asp Lys Ser Arg Trp Gln Gln Gly Asn Val Phe Ser
785                 790                 795                 800

Cys Ser Val Met His Glu Ala Leu His Asn His Tyr Thr Gln Lys Ser
                805                 810                 815

Leu Ser Leu Ser Pro Gly Lys
            820

<210> SEQ ID NO 17
<211> LENGTH: 576
<212> TYPE: PRT
<213> ORGANISM: Artificial Sequence
<220> FEATURE:
<223> OTHER INFORMATION: HA1-Fd-hFc fusion protein

<400> SEQUENCE: 17

Ile Cys Ile Gly Tyr His Ala Asn Asn Ser Thr Glu Gln Val Asp Thr
1               5                   10                  15

Ile Met Glu Lys Asn Val Thr Val Thr His Ala Gln Asp Ile Leu Glu
            20                  25                  30
```

-continued

```
Lys Thr His Asn Gly Lys Leu Cys Asp Leu Asp Gly Val Lys Pro Leu
             35                  40                  45
Ile Leu Arg Asp Cys Ser Val Ala Gly Trp Leu Leu Gly Asn Pro Met
 50                  55                  60
Cys Asp Glu Phe Ile Asn Val Pro Glu Trp Ser Tyr Ile Val Glu Lys
 65                  70                  75                  80
Ala Asn Pro Ala Asn Asp Leu Cys Tyr Pro Gly Asn Phe Asn Asp Tyr
                 85                  90                  95
Glu Glu Leu Lys His Leu Leu Ser Arg Ile Asn His Phe Glu Lys Ile
            100                 105                 110
Gln Ile Ile Pro Lys Ser Ser Trp Ser Asp His Glu Ala Ser Ser Gly
            115                 120                 125
Val Ser Ser Ala Cys Pro Tyr Gln Gly Thr Pro Ser Phe Phe Arg Asn
130                 135                 140
Val Val Trp Leu Ile Lys Lys Asn Asn Thr Tyr Pro Thr Ile Lys Arg
145                 150                 155                 160
Ser Tyr Asn Asn Thr Asn Gln Glu Asp Leu Leu Ile Leu Trp Gly Ile
                165                 170                 175
His His Ser Asn Asp Ala Ala Glu Gln Thr Lys Leu Tyr Gln Asn Pro
            180                 185                 190
Thr Thr Tyr Ile Ser Val Gly Thr Ser Thr Leu Asn Gln Arg Leu Val
            195                 200                 205
Pro Lys Ile Ala Thr Arg Ser Lys Val Asn Gly Gln Asn Gly Arg Met
            210                 215                 220
Asp Phe Phe Trp Thr Ile Leu Lys Pro Asn Asp Ala Ile Asn Phe Glu
225                 230                 235                 240
Ser Asn Gly Asn Phe Ile Ala Pro Glu Tyr Ala Tyr Lys Ile Val Lys
                245                 250                 255
Lys Gly Asp Ser Ala Ile Val Lys Ser Glu Val Glu Tyr Gly Asn Cys
            260                 265                 270
Asn Thr Lys Cys Gln Thr Pro Ile Gly Ala Ile Asn Ser Ser Met Pro
            275                 280                 285
Phe His Asn Ile His Pro Leu Thr Ile Gly Glu Cys Pro Lys Tyr Val
            290                 295                 300
Lys Ser Asn Lys Leu Val Leu Ala Thr Gly Leu Arg Asn Ser Pro Leu
305                 310                 315                 320
Gly Tyr Ile Pro Glu Ala Pro Arg Asp Gly Gln Ala Tyr Val Arg Lys
                325                 330                 335
Asp Gly Glu Trp Val Leu Leu Ser Thr Phe Leu Arg Ser Asp Lys Thr
            340                 345                 350
His Thr Cys Pro Pro Cys Pro Ala Pro Glu Leu Leu Gly Gly Pro Ser
            355                 360                 365
Val Phe Leu Phe Pro Pro Lys Pro Lys Asp Thr Leu Met Ile Ser Arg
370                 375                 380
Thr Pro Glu Val Thr Cys Val Val Asp Val Ser His Glu Asp Pro
385                 390                 395                 400
Glu Val Lys Phe Asn Trp Tyr Val Asp Gly Val Glu Val His Asn Ala
                405                 410                 415
Lys Thr Lys Pro Arg Glu Glu Gln Tyr Asn Ser Thr Tyr Arg Val Val
            420                 425                 430
Ser Val Leu Thr Val Leu His Gln Asp Trp Leu Asn Gly Lys Glu Tyr
            435                 440                 445
Lys Cys Lys Val Ser Asn Lys Ala Leu Pro Ala Pro Ile Glu Lys Thr
```

```
                    450                 455                 460
Ile Ser Lys Ala Lys Gly Gln Pro Arg Glu Pro Gln Val Tyr Thr Leu
465                 470                 475                 480

Pro Pro Ser Arg Glu Glu Met Thr Lys Asn Gln Val Ser Leu Thr Cys
                    485                 490                 495

Leu Val Lys Gly Phe Tyr Pro Ser Asp Ile Ala Val Glu Trp Glu Ser
                500                 505                 510

Asn Gly Gln Pro Glu Asn Asn Tyr Lys Thr Thr Pro Pro Val Leu Asp
                515                 520                 525

Ser Asp Gly Ser Phe Phe Leu Tyr Ser Lys Leu Thr Val Asp Lys Ser
530                 535                 540

Arg Trp Gln Gln Gly Asn Val Phe Ser Cys Ser Val Met His Glu Ala
545                 550                 555                 560

Leu His Asn His Tyr Thr Gln Lys Ser Leu Ser Leu Ser Pro Gly Lys
                565                 570                 575

<210> SEQ ID NO 18
<211> LENGTH: 478
<212> TYPE: PRT
<213> ORGANISM: Artificial Sequence
<220> FEATURE:
<223> OTHER INFORMATION: HA2-Fd-hFc fusion protein

<400> SEQUENCE: 18

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
                20                  25                  30

Gly Tyr Ala Ala Asp Lys Glu Ser Thr Gln Lys Ala Ile Asp Gly Val
            35                  40                  45

Thr Asn Lys Val Asn Ser Ile Ile Asp Lys Met Asn Thr Gln Phe Glu
        50                  55                  60

Ala Val Gly Arg Glu Phe Asn Asn Leu Glu Arg Arg Ile Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
                100                 105                 110

Ser Asn Val Lys Asn Leu Tyr Asp Lys Val Arg Leu Gln Leu Arg Asp
            115                 120                 125

Asn Ala Lys Glu Leu Gly Asn Gly Cys Phe Glu Phe Tyr His Lys Cys
        130                 135                 140

Asp Asn Glu Cys Met Glu Ser Val Arg Asn Gly Thr Tyr Asp Tyr Pro
145                 150                 155                 160

Gln Tyr Ser Glu Glu Ala Arg Leu Lys Arg Glu Glu Ile Ser Gly Val
                165                 170                 175

Lys Leu Glu Ser Ile Gly Thr Tyr Gln Ile Leu Ser Ile Tyr Ser Thr
            180                 185                 190

Val Ala Ser Ser Leu Ala Leu Ala Ile Met Val Ala Gly Leu Ser Leu
        195                 200                 205

Trp Met Cys Ser Asn Gly Ser Leu Gln Cys Arg Ile Cys Ile Gly Tyr
        210                 215                 220

Ile Pro Glu Ala Pro Arg Asp Gly Gln Ala Tyr Val Arg Lys Asp Gly
225                 230                 235                 240

Glu Trp Val Leu Leu Ser Thr Phe Leu Arg Ser Asp Lys Thr His Thr
```

```
                    245                 250                 255
Cys Pro Pro Cys Pro Ala Pro Glu Leu Leu Gly Gly Pro Ser Val Phe
                260                 265                 270

Leu Phe Pro Pro Lys Pro Lys Asp Thr Leu Met Ile Ser Arg Thr Pro
            275                 280                 285

Glu Val Thr Cys Val Val Val Asp Val Ser His Glu Asp Pro Glu Val
        290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Arg Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 19
<211> LENGTH: 411
<212> TYPE: PRT
<213> ORGANISM: Artificial Sequence
<220> FEATURE:
<223> OTHER INFORMATION: HA-RBD-hFc fusion protein

<400> SEQUENCE: 19

Leu Ser Arg Ile Asn His Phe Glu Lys Ile Gln Ile Ile Pro Lys Ser
1               5                   10                  15

Ser Trp Ser Asp His Glu Ala Ser Ser Gly Val Ser Ser Ala Cys Pro
            20                  25                  30

Tyr Gln Gly Thr Pro Ser Phe Phe Arg Asn Val Val Trp Leu Ile Lys
        35                  40                  45

Lys Asn Asn Thr Tyr Pro Thr Ile Lys Arg Ser Tyr Asn Asn Thr Asn
    50                  55                  60

Gln Glu Asp Leu Leu Ile Leu Trp Gly Ile His His Ser Asn Asp Ala
65                  70                  75                  80

Ala Glu Gln Thr Lys Leu Tyr Gln Asn Pro Thr Thr Tyr Ile Ser Val
                85                  90                  95

Gly Thr Ser Thr Leu Asn Gln Arg Leu Val Pro Lys Ile Ala Thr Arg
            100                 105                 110

Ser Lys Val Asn Gly Gln Asn Gly Arg Met Asp Phe Phe Trp Thr Ile
        115                 120                 125

Leu Lys Pro Asn Asp Ala Ile Asn Phe Glu Ser Asn Gly Asn Phe Ile
```

```
            130                 135                 140
Ala Pro Glu Tyr Ala Tyr Lys Ile Val Lys Lys Gly Tyr Ile Pro Glu
145                 150                 155                 160

Ala Pro Arg Asp Gly Gln Ala Tyr Val Arg Lys Asp Gly Glu Trp Val
                165                 170                 175

Leu Leu Ser Thr Phe Leu Arg Ser Asp Lys Thr His Thr Cys Pro Pro
            180                 185                 190

Cys Pro Ala Pro Glu Leu Leu Gly Gly Pro Ser Val Phe Leu Phe Pro
        195                 200                 205

Pro Lys Pro Lys Asp Thr Leu Met Ile Ser Arg Thr Pro Glu Val Thr
210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Asn Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
290                 295                 300

Gly Gln Pro Arg Glu Pro Gln Val Tyr Thr Leu Pro Pro Ser Arg Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Lys Leu Thr Val Asp Lys Ser Arg Trp Gln Gln Gly
370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410

<210> SEQ ID NO 20
<211> LENGTH: 234
<212> TYPE: PRT
<213> ORGANISM: Mus musculus

<400> SEQUENCE: 20

Arg Ser Pro Arg Gly Pro Thr Ile Lys Pro Cys Pro Pro Cys Lys Cys
1               5                   10                  15

Pro Ala Pro Asn Leu Leu Gly Gly Pro Ser Val Phe Ile Phe Pro Pro
                20                  25                  30

Lys Ile Lys Asp Val Leu Met Ile Ser Leu Ser Pro Ile Val Thr Cys
            35                  40                  45

Val Val Val Asp Val Ser Glu Asp Asp Pro Asp Val Gln Ile Ser Trp
        50                  55                  60

Phe Val Asn Asn Val Glu Val His Thr Ala Gln Thr Gln Thr His Arg
65                  70                  75                  80

Glu Asp Tyr Asn Ser Thr Leu Arg Val Val Ser Ala Leu Pro Ile Gln
                85                  90                  95
```

His Gln Asp Trp Met Ser Gly Lys Glu Phe Lys Cys Lys Val Asn Asn
            100                 105                 110

Lys Asp Leu Pro Ala Pro Ile Glu Arg Thr Ile Ser Lys Pro Lys Gly
        115                 120                 125

Ser Val Arg Ala Pro Gln Val Tyr Val Leu Pro Pro Glu Glu Glu
    130                 135                 140

Met Thr Lys Lys Gln Val Thr Leu Thr Cys Met Val Thr Asp Phe Met
145                 150                 155                 160

Pro Glu Asp Ile Tyr Val Glu Trp Thr Asn Asn Gly Lys Thr Glu Leu
                165                 170                 175

Asn Tyr Lys Asn Thr Glu Pro Val Leu Asp Ser Asp Gly Ser Tyr Phe
            180                 185                 190

Met Tyr Ser Lys Leu Arg Val Glu Lys Lys Asn Trp Val Glu Arg Asn
        195                 200                 205

Ser Tyr Ser Cys Ser Val Val His Glu Gly Leu His Asn His His Thr
    210                 215                 220

Thr Lys Ser Phe Ser Arg Thr Pro Gly Lys
225                 230

<210> SEQ ID NO 21
<211> LENGTH: 828
<212> TYPE: PRT
<213> ORGANISM: Artificial Sequence
<220> FEATURE:
<223> OTHER INFORMATION: HA-Fd-mFc fusion protein

<400> SEQUENCE: 21

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

```
Leu Val Pro Lys Ile Ala Thr Arg Ser Lys Val Asn Gly Gln Asn Gly
225                 230                 235                 240

Arg Met Asp Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
        260                 265                 270

Val Lys Lys Gly Asp Ser Ala Ile Val Lys Ser Glu Val Glu Tyr Gly
    275                 280                 285

Asn Cys Asn Thr Lys Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Arg Arg Lys Arg Gly Leu Phe Gly Ala Ile Ala
            340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
        515                 520                 525

Tyr Gln Ile Leu Ser Ile Tyr Ser Thr Val Ala Ser Ser Leu Ala Leu
    530                 535                 540

Ala Ile Met Val Ala Gly Leu Ser Leu Trp Met Cys Ser Asn Gly Ser
545                 550                 555                 560

Leu Gln Cys Arg Ile Cys Ile Gly Tyr Ile Pro Glu Ala Pro Arg Asp
                565                 570                 575

Gly Gln Ala Tyr Val Arg Lys Asp Gly Glu Trp Val Leu Leu Ser Thr
            580                 585                 590

Phe Leu Arg Ser Pro Arg Gly Pro Thr Ile Lys Pro Cys Pro Pro Cys
        595                 600                 605

Lys Cys Pro Ala Pro Asn Leu Leu Gly Gly Pro Ser Val Phe Ile Phe
    610                 615                 620

Pro Pro Lys Ile Lys Asp Val Leu Met Ile Ser Leu Ser Pro Ile Val
625                 630                 635                 640

Thr Cys Val Val Val Asp Val Ser Glu Asp Asp Pro Asp Val Gln Ile
```

```
                        645                 650                 655
Ser Trp Phe Val Asn Asn Val Glu Val His Thr Ala Gln Thr Gln Thr
                660                 665                 670

His Arg Glu Asp Tyr Asn Ser Thr Leu Arg Val Val Ser Ala Leu Pro
            675                 680                 685

Ile Gln His Gln Asp Trp Met Ser Gly Lys Glu Phe Lys Cys Lys Val
        690                 695                 700

Asn Asn Lys Asp Leu Pro Ala Pro Ile Glu Arg Thr Ile Ser Lys Pro
705                 710                 715                 720

Lys Gly Ser Val Arg Ala Pro Gln Val Tyr Val Leu Pro Pro Pro Glu
                725                 730                 735

Glu Glu Met Thr Lys Lys Gln Val Thr Leu Thr Cys Met Val Thr Asp
            740                 745                 750

Phe Met Pro Glu Asp Ile Tyr Val Glu Trp Thr Asn Asn Gly Lys Thr
        755                 760                 765

Glu Leu Asn Tyr Lys Asn Thr Glu Pro Val Leu Asp Ser Asp Gly Ser
    770                 775                 780

Tyr Phe Met Tyr Ser Lys Leu Arg Val Glu Lys Lys Asn Trp Val Glu
785                 790                 795                 800

Arg Asn Ser Tyr Ser Cys Ser Val Val His Glu Gly Leu His Asn His
                805                 810                 815

His Thr Thr Lys Ser Phe Ser Arg Thr Pro Gly Lys
            820                 825

<210> SEQ ID NO 22
<211> LENGTH: 581
<212> TYPE: PRT
<213> ORGANISM: Artificial Sequence
<220> FEATURE:
<223> OTHER INFORMATION: HA1-Fd-mFc fusion protein

<400> SEQUENCE: 22

Ile Cys Ile Gly Tyr His Ala Asn Asn Ser Thr Glu Gln Val Asp Thr
1               5                   10                  15

Ile Met Glu Lys Asn Val Thr Val Thr His Ala Gln Asp Ile Leu Glu
                20                  25                  30

Lys Thr His Asn Gly Lys Leu Cys Asp Leu Asp Gly Val Lys Pro Leu
            35                  40                  45

Ile Leu Arg Asp Cys Ser Val Ala Gly Trp Leu Leu Gly Asn Pro Met
        50                  55                  60

Cys Asp Glu Phe Ile Asn Val Pro Glu Trp Ser Tyr Ile Val Glu Lys
65                  70                  75                  80

Ala Asn Pro Ala Asn Asp Leu Cys Tyr Pro Gly Asn Phe Asn Asp Tyr
                85                  90                  95

Glu Glu Leu Lys His Leu Leu Ser Arg Ile Asn His Phe Glu Lys Ile
            100                 105                 110

Gln Ile Ile Pro Lys Ser Ser Trp Ser Asp His Glu Ala Ser Ser Gly
        115                 120                 125

Val Ser Ser Ala Cys Pro Tyr Gln Gly Thr Pro Ser Phe Phe Arg Asn
    130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
```

```
            180             185             190
Thr Thr Tyr Ile Ser Val Gly Thr Ser Thr Leu Asn Gln Arg Leu Val
        195                 200                 205
Pro Lys Ile Ala Thr Arg Ser Lys Val Asn Gly Gln Asn Gly Arg Met
        210                 215                 220
Asp Phe Phe Trp Thr Ile Leu Lys Pro Asn Asp Ala Ile Asn Phe Glu
225                 230                 235                 240
Ser Asn Gly Asn Phe Ile Ala Pro Glu Tyr Ala Tyr Lys Ile Val Lys
                245                 250                 255
Lys Gly Asp Ser Ala Ile Val Lys Ser Glu Val Glu Tyr Gly Asn Cys
                260                 265                 270
Asn Thr Lys Cys Gln Thr Pro Ile Gly Ala Ile Asn Ser Ser Met Pro
        275                 280                 285
Phe His Asn Ile His Pro Leu Thr Ile Gly Glu Cys Pro Lys Tyr Val
        290                 295                 300
Lys Ser Asn Lys Leu Val Leu Ala Thr Gly Leu Arg Asn Ser Pro Leu
305                 310                 315                 320
Gly Tyr Ile Pro Glu Ala Pro Arg Asp Gly Gln Ala Tyr Val Arg Lys
                325                 330                 335
Asp Gly Glu Trp Val Leu Leu Ser Thr Phe Leu Arg Ser Pro Arg Gly
                340                 345                 350
Pro Thr Ile Lys Pro Cys Pro Cys Lys Cys Pro Ala Pro Asn Leu
        355                 360                 365
Leu Gly Gly Pro Ser Val Phe Ile Phe Pro Pro Lys Ile Lys Asp Val
        370                 375                 380
Leu Met Ile Ser Leu Ser Pro Ile Val Thr Cys Val Val Val Asp Val
385                 390                 395                 400
Ser Glu Asp Asp Pro Asp Val Gln Ile Ser Trp Phe Val Asn Asn Val
                405                 410                 415
Glu Val His Thr Ala Gln Thr Gln Thr His Arg Glu Asp Tyr Asn Ser
                420                 425                 430
Thr Leu Arg Val Val Ser Ala Leu Pro Ile Gln His Gln Asp Trp Met
        435                 440                 445
Ser Gly Lys Glu Phe Lys Cys Lys Val Asn Asn Lys Asp Leu Pro Ala
        450                 455                 460
Pro Ile Glu Arg Thr Ile Ser Lys Pro Lys Gly Ser Val Arg Ala Pro
465                 470                 475                 480
Gln Val Tyr Val Leu Pro Pro Glu Glu Glu Met Thr Lys Lys Gln
                485                 490                 495
Val Thr Leu Thr Cys Met Val Thr Asp Phe Met Pro Glu Asp Ile Tyr
        500                 505                 510
Val Glu Trp Thr Asn Asn Gly Lys Thr Glu Leu Asn Tyr Lys Asn Thr
        515                 520                 525
Glu Pro Val Leu Asp Ser Asp Gly Ser Tyr Phe Met Tyr Ser Lys Leu
        530                 535                 540
Arg Val Glu Lys Lys Asn Trp Val Glu Arg Asn Ser Tyr Ser Cys Ser
545                 550                 555                 560
Val Val His Glu Gly Leu His Asn His His Thr Thr Lys Ser Phe Ser
                565                 570                 575
Arg Thr Pro Gly Lys
                580

<210> SEQ ID NO 23
```

<211> LENGTH: 483
<212> TYPE: PRT
<213> ORGANISM: Artificial Sequence
<220> FEATURE:
<223> OTHER INFORMATION: HA2-Fd-mFc fusion protein

<400> SEQUENCE: 23

```
Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
            20                  25                  30

Gly Tyr Ala Ala Asp Lys Glu Ser Thr Gln Lys Ala Ile Asp Gly Val
        35                  40                  45

Thr Asn Lys Val Asn Ser Ile Ile Asp Lys Met Asn Thr Gln Phe Glu
    50                  55                  60

Ala Val Gly Arg Glu Phe Asn Asn Leu Glu Arg Arg Ile Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Tyr Asp Lys Val Arg Leu Gln Leu Arg Asp
        115                 120                 125

Asn Ala Lys Glu Leu Gly Asn Gly Cys Phe Glu Phe Tyr His Lys Cys
    130                 135                 140

Asp Asn Glu Cys Met Glu Ser Val Arg Asn Gly Thr Tyr Asp Tyr Pro
145                 150                 155                 160

Gln Tyr Ser Glu Glu Ala Arg Leu Lys Arg Glu Glu Ile Ser Gly Val
                165                 170                 175

Lys Leu Glu Ser Ile Gly Thr Tyr Gln Ile Leu Ser Ile Tyr Ser Thr
            180                 185                 190

Val Ala Ser Ser Leu Ala Leu Ala Ile Met Val Ala Gly Leu Ser Leu
        195                 200                 205

Trp Met Cys Ser Asn Gly Ser Leu Gln Cys Arg Ile Cys Ile Gly Tyr
    210                 215                 220

Ile Pro Glu Ala Pro Arg Asp Gly Gln Ala Tyr Val Arg Lys Asp Gly
225                 230                 235                 240

Glu Trp Val Leu Leu Ser Thr Phe Leu Arg Ser Pro Arg Gly Pro Thr
                245                 250                 255

Ile Lys Pro Cys Pro Pro Cys Lys Cys Pro Ala Pro Asn Leu Leu Gly
            260                 265                 270

Gly Pro Ser Val Phe Ile Phe Pro Pro Lys Ile Lys Asp Val Leu Met
        275                 280                 285

Ile Ser Leu Ser Pro Ile Val Thr Cys Val Val Val Asp Val Ser Glu
    290                 295                 300

Asp Asp Pro Asp Val Gln Ile Ser Trp Phe Val Asn Asn Val Glu Val
305                 310                 315                 320

His Thr Ala Gln Thr Gln Thr His Arg Glu Asp Tyr Asn Ser Thr Leu
                325                 330                 335

Arg Val Val Ser Ala Leu Pro Ile Gln His Gln Asp Trp Met Ser Gly
            340                 345                 350

Lys Glu Phe Lys Cys Lys Val Asn Asn Lys Asp Leu Pro Ala Pro Ile
        355                 360                 365

Glu Arg Thr Ile Ser Lys Pro Lys Gly Ser Val Arg Ala Pro Gln Val
    370                 375                 380
```

```
Tyr Val Leu Pro Pro Glu Glu Glu Met Thr Lys Lys Gln Val Thr
385                 390                 395                 400

Leu Thr Cys Met Val Thr Asp Phe Met Pro Glu Asp Ile Tyr Val Glu
                405                 410                 415

Trp Thr Asn Asn Gly Lys Thr Glu Leu Asn Tyr Lys Asn Thr Glu Pro
            420                 425                 430

Val Leu Asp Ser Asp Gly Ser Tyr Phe Met Tyr Ser Lys Leu Arg Val
        435                 440                 445

Glu Lys Lys Asn Trp Val Glu Arg Asn Ser Tyr Ser Cys Ser Val Val
    450                 455                 460

His Glu Gly Leu His Asn His Thr Thr Lys Ser Phe Ser Arg Thr
465                 470                 475                 480

Pro Gly Lys

<210> SEQ ID NO 24
<211> LENGTH: 416
<212> TYPE: PRT
<213> ORGANISM: Artificial Sequence
<220> FEATURE:
<223> OTHER INFORMATION: HA-RBD-Fd-mFc fusion protein

<400> SEQUENCE: 24

Leu Ser Arg Ile Asn His Phe Glu Lys Ile Gln Ile Ile Pro Lys Ser
1               5                   10                  15

Ser Trp Ser Asp His Glu Ala Ser Ser Gly Val Ser Ser Ala Cys Pro
            20                  25                  30

Tyr Gln Gly Thr Pro Ser Phe Phe Arg Asn Val Val Trp Leu Ile Lys
        35                  40                  45

Lys Asn Asn Thr Tyr Pro Thr Ile Lys Arg Ser Tyr Asn Asn Thr Asn
50                  55                  60

Gln Glu Asp Leu Leu Ile Leu Trp Gly Ile His His Ser Asn Asp Ala
65                  70                  75                  80

Ala Glu Gln Thr Lys Leu Tyr Gln Asn Pro Thr Thr Tyr Ile Ser Val
                85                  90                  95

Gly Thr Ser Thr Leu Asn Gln Arg Leu Val Pro Lys Ile Ala Thr Arg
            100                 105                 110

Ser Lys Val Asn Gly Gln Asn Gly Arg Met Asp Phe Phe Trp Thr Ile
        115                 120                 125

Leu Lys Pro Asn Asp Ala Ile Asn Phe Glu Ser Asn Gly Asn Phe Ile
130                 135                 140

Ala Pro Glu Tyr Ala Tyr Lys Ile Val Lys Lys Gly Tyr Ile Pro Glu
145                 150                 155                 160

Ala Pro Arg Asp Gly Gln Ala Tyr Val Arg Lys Asp Gly Glu Trp Val
                165                 170                 175

Leu Leu Ser Thr Phe Leu Arg Ser Pro Arg Gly Pro Thr Ile Lys Pro
            180                 185                 190

Cys Pro Pro Cys Lys Cys Pro Ala Pro Asn Leu Leu Gly Gly Pro Ser
        195                 200                 205

Val Phe Ile Phe Pro Pro Lys Ile Lys Asp Val Leu Met Ile Ser Leu
    210                 215                 220

Ser Pro Ile Val Thr Cys Val Val Asp Val Ser Glu Asp Asp Pro
225                 230                 235                 240

Asp Val Gln Ile Ser Trp Phe Val Asn Asn Val Glu Val His Thr Ala
                245                 250                 255
```

```
Gln Thr Gln Thr His Arg Glu Asp Tyr Asn Ser Thr Leu Arg Val Val
                260                 265                 270

Ser Ala Leu Pro Ile Gln His Gln Asp Trp Met Ser Gly Lys Glu Phe
            275                 280                 285

Lys Cys Lys Val Asn Asn Lys Asp Leu Pro Ala Pro Ile Glu Arg Thr
        290                 295                 300

Ile Ser Lys Pro Lys Gly Ser Val Arg Ala Pro Gln Val Tyr Val Leu
305                 310                 315                 320

Pro Pro Pro Glu Glu Met Thr Lys Lys Gln Val Thr Leu Thr Cys
                325                 330                 335

Met Val Thr Asp Phe Met Pro Glu Asp Ile Tyr Val Glu Trp Thr Asn
            340                 345                 350

Asn Gly Lys Thr Glu Leu Asn Tyr Lys Asn Thr Glu Pro Val Leu Asp
        355                 360                 365

Ser Asp Gly Ser Tyr Phe Met Tyr Ser Lys Leu Arg Val Glu Lys Lys
    370                 375                 380

Asn Trp Val Glu Arg Asn Ser Tyr Ser Cys Ser Val Val His Glu Gly
385                 390                 395                 400

Leu His Asn His His Thr Thr Lys Ser Phe Ser Arg Thr Pro Gly Lys
                405                 410                 415

<210> SEQ ID NO 25
<211> LENGTH: 225
<212> TYPE: PRT
<213> ORGANISM: Oryctolagus cuniculus

<400> SEQUENCE: 25

Arg Ser Ser Lys Pro Thr Cys Pro Pro Pro Glu Leu Leu Gly Gly Pro
1               5                   10                  15

Ser Val Phe Ile Phe Pro Pro Lys Pro Lys Asp Thr Leu Met Ile Ser
            20                  25                  30

Arg Thr Pro Glu Val Thr Cys Val Val Val Asp Val Ser Gln Asp Asp
        35                  40                  45

Pro Glu Val Gln Phe Thr Trp Tyr Ile Asn Asn Glu Gln Val Arg Thr
    50                  55                  60

Ala Arg Pro Pro Leu Arg Glu Gln Gln Phe Asn Ser Thr Ile Arg Val
65                  70                  75                  80

Val Ser Thr Leu Pro Ile Ala His Gln Asp Trp Leu Arg Gly Lys Glu
                85                  90                  95

Phe Lys Cys Lys Val His Asn Lys Ala Leu Pro Ala Pro Ile Glu Lys
            100                 105                 110

Thr Ile Ser Lys Ala Arg Gly Gln Pro Leu Glu Pro Lys Val Tyr Thr
        115                 120                 125

Met Gly Pro Pro Arg Glu Glu Leu Ser Ser Arg Ser Val Ser Leu Thr
    130                 135                 140

Cys Met Ile Asn Gly Phe Tyr Pro Ser Asp Ile Ser Val Glu Trp Glu
145                 150                 155                 160

Lys Asn Gly Lys Ala Glu Asp Asn Tyr Lys Thr Thr Pro Ala Val Leu
                165                 170                 175

Asp Ser Asp Gly Ser Tyr Phe Leu Tyr Ser Lys Leu Ser Val Pro Thr
            180                 185                 190

Ser Glu Trp Gln Arg Gly Asp Val Phe Thr Cys Ser Val Met His Glu
        195                 200                 205

Ala Leu His Asn His Tyr Thr Gln Lys Ser Ile Ser Arg Ser Pro Gly
    210                 215                 220
```

Lys
225

<210> SEQ ID NO 26
<211> LENGTH: 819
<212> TYPE: PRT
<213> ORGANISM: Artificial Sequence
<220> FEATURE:
<223> OTHER INFORMATION: HA-Fd-rFc fusion protein

<400> SEQUENCE: 26

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Asn Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Val Lys Ser Glu Val Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Arg Arg Lys Arg Gly Leu Phe Gly Ala Ile Ala
            340                 345                 350

-continued

Gly Phe Ile Glu Gly Gly Trp Gln Gly Met Val Asp Gly Trp Tyr Gly
            355                 360                 365

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
        515                 520                 525

Tyr Gln Ile Leu Ser Ile Tyr Ser Thr Val Ala Ser Ser Leu Ala Leu
    530                 535                 540

Ala Ile Met Val Ala Gly Leu Ser Leu Trp Met Cys Ser Asn Gly Ser
545                 550                 555                 560

Leu Gln Cys Arg Ile Cys Ile Gly Tyr Ile Pro Glu Ala Pro Arg Asp
                565                 570                 575

Gly Gln Ala Tyr Val Arg Lys Asp Gly Glu Trp Val Leu Leu Ser Thr
            580                 585                 590

Phe Leu Arg Ser Ser Lys Pro Thr Cys Pro Pro Glu Leu Leu Gly
        595                 600                 605

Gly Pro Ser Val Phe Ile Phe Pro Pro Lys Pro Lys Asp Thr Leu Met
    610                 615                 620

Ile Ser Arg Thr Pro Glu Val Thr Cys Val Val Val Asp Val Ser Gln
625                 630                 635                 640

Asp Asp Pro Glu Val Gln Phe Thr Trp Tyr Ile Asn Asn Glu Gln Val
                645                 650                 655

Arg Thr Ala Arg Pro Pro Leu Arg Glu Gln Gln Phe Asn Ser Thr Ile
            660                 665                 670

Arg Val Val Ser Thr Leu Pro Ile Ala His Gln Asp Trp Leu Arg Gly
        675                 680                 685

Lys Glu Phe Lys Cys Lys Val His Asn Lys Ala Leu Pro Ala Pro Ile
    690                 695                 700

Glu Lys Thr Ile Ser Lys Ala Arg Gly Gln Pro Leu Glu Pro Lys Val
705                 710                 715                 720

Tyr Thr Met Gly Pro Pro Arg Glu Glu Leu Ser Ser Arg Ser Val Ser
                725                 730                 735

Leu Thr Cys Met Ile Asn Gly Phe Tyr Pro Ser Asp Ile Ser Val Glu
            740                 745                 750

Trp Glu Lys Asn Gly Lys Ala Glu Asp Asn Tyr Lys Thr Thr Pro Ala
        755                 760                 765

-continued

```
Val Leu Asp Ser Asp Gly Ser Tyr Phe Leu Tyr Ser Lys Leu Ser Val
    770             775                 780
Pro Thr Ser Glu Trp Gln Arg Gly Asp Val Phe Thr Cys Ser Val Met
785             790                 795                 800
His Glu Ala Leu His Asn His Tyr Thr Gln Lys Ser Ile Ser Arg Ser
                805                 810                 815
Pro Gly Lys

<210> SEQ ID NO 27
<211> LENGTH: 572
<212> TYPE: PRT
<213> ORGANISM: Artificial Sequence
<220> FEATURE:
<223> OTHER INFORMATION: HA1-Fd-rFc fusion protein

<400> SEQUENCE: 27

Ile Cys Ile Gly Tyr His Ala Asn Asn Ser Thr Glu Gln Val Asp Thr
1               5                   10                  15
Ile Met Glu Lys Asn Val Thr Val Thr His Ala Gln Asp Ile Leu Glu
            20                  25                  30
Lys Thr His Asn Gly Lys Leu Cys Asp Leu Asp Gly Val Lys Pro Leu
        35                  40                  45
Ile Leu Arg Asp Cys Ser Val Ala Gly Trp Leu Leu Gly Asn Pro Met
    50                  55                  60
Cys Asp Glu Phe Ile Asn Val Pro Glu Trp Ser Tyr Ile Val Glu Lys
65                  70                  75                  80
Ala Asn Pro Ala Asn Asp Leu Cys Tyr Pro Gly Asn Phe Asn Asp Tyr
                85                  90                  95
Glu Glu Leu Lys His Leu Leu Ser Arg Ile Asn His Phe Glu Lys Ile
            100                 105                 110
Gln Ile Ile Pro Lys Ser Ser Trp Ser Asp His Glu Ala Ser Ser Gly
        115                 120                 125
Val Ser Ser Ala Cys Pro Tyr Gln Gly Thr Pro Ser Phe Phe Arg Asn
    130                 135                 140
Val Val Trp Leu Ile Lys Lys Asn Asn Thr Tyr Pro Thr Ile Lys Arg
145                 150                 155                 160
Ser Tyr Asn Asn Thr Asn Gln Glu Asp Leu Leu Ile Leu Trp Gly Ile
                165                 170                 175
His His Ser Asn Asp Ala Ala Glu Gln Thr Lys Leu Tyr Gln Asn Pro
            180                 185                 190
Thr Thr Tyr Ile Ser Val Gly Thr Ser Thr Leu Asn Gln Arg Leu Val
        195                 200                 205
Pro Lys Ile Ala Thr Arg Ser Lys Val Asn Gly Gln Asn Gly Arg Met
    210                 215                 220
Asp Phe Phe Trp Thr Ile Leu Lys Pro Asn Asp Ala Ile Asn Phe Glu
225                 230                 235                 240
Ser Asn Gly Asn Phe Ile Ala Pro Glu Tyr Ala Tyr Lys Ile Val Lys
                245                 250                 255
Lys Gly Asp Ser Ala Ile Val Lys Ser Glu Val Glu Tyr Gly Asn Cys
            260                 265                 270
Asn Thr Lys Cys Gln Thr Pro Ile Gly Ala Ile Asn Ser Ser Met Pro
        275                 280                 285
Phe His Asn Ile His Pro Leu Thr Ile Gly Glu Cys Pro Lys Tyr Val
    290                 295                 300
Lys Ser Asn Lys Leu Val Leu Ala Thr Gly Leu Arg Asn Ser Pro Leu
```

```
                305                 310                 315                 320
Gly Tyr Ile Pro Glu Ala Pro Arg Asp Gly Gln Ala Tyr Val Arg Lys
                    325                 330                 335

Asp Gly Glu Trp Val Leu Leu Ser Thr Phe Leu Arg Ser Ser Lys Pro
                340                 345                 350

Thr Cys Pro Pro Pro Glu Leu Leu Gly Gly Pro Ser Val Phe Ile Phe
            355                 360                 365

Pro Pro Lys Pro Lys Asp Thr Leu Met Ile Ser Arg Thr Pro Glu Val
    370                 375                 380

Thr Cys Val Val Val Asp Val Ser Gln Asp Asp Pro Glu Val Gln Phe
385                 390                 395                 400

Thr Trp Tyr Ile Asn Asn Glu Gln Val Arg Thr Ala Arg Pro Pro Leu
                405                 410                 415

Arg Glu Gln Gln Phe Asn Ser Thr Ile Arg Val Val Ser Thr Leu Pro
                420                 425                 430

Ile Ala His Gln Asp Trp Leu Arg Gly Lys Glu Phe Lys Cys Lys Val
                435                 440                 445

His Asn Lys Ala Leu Pro Ala Pro Ile Glu Lys Thr Ile Ser Lys Ala
            450                 455                 460

Arg Gly Gln Pro Leu Glu Pro Lys Val Tyr Thr Met Gly Pro Pro Arg
465                 470                 475                 480

Glu Glu Leu Ser Ser Arg Ser Val Ser Leu Thr Cys Met Ile Asn Gly
                485                 490                 495

Phe Tyr Pro Ser Asp Ile Ser Val Glu Trp Glu Lys Asn Gly Lys Ala
                500                 505                 510

Glu Asp Asn Tyr Lys Thr Thr Pro Ala Val Leu Asp Ser Asp Gly Ser
            515                 520                 525

Tyr Phe Leu Tyr Ser Lys Leu Ser Val Pro Thr Ser Glu Trp Gln Arg
    530                 535                 540

Gly Asp Val Phe Thr Cys Ser Val Met His Glu Ala Leu His Asn His
545                 550                 555                 560

Tyr Thr Gln Lys Ser Ile Ser Arg Ser Pro Gly Lys
                565                 570

<210> SEQ ID NO 28
<211> LENGTH: 474
<212> TYPE: PRT
<213> ORGANISM: Artificial Sequence
<220> FEATURE:
<223> OTHER INFORMATION: HA2-Fd-rFc fusion protein

<400> SEQUENCE: 28

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
                20                  25                  30

Gly Tyr Ala Ala Asp Lys Glu Ser Thr Gln Lys Ala Ile Asp Gly Val
            35                  40                  45

Thr Asn Lys Val Asn Ser Ile Ile Asp Lys Met Asn Thr Gln Phe Glu
    50                  55                  60

Ala Val Gly Arg Glu Phe Asn Asn Leu Glu Arg Arg Ile Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
```

```
            100                 105                 110
Ser Asn Val Lys Asn Leu Tyr Asp Lys Val Arg Leu Gln Leu Arg Asp
            115                 120                 125

Asn Ala Lys Glu Leu Gly Asn Gly Cys Phe Glu Phe Tyr His Lys Cys
            130                 135             140

Asp Asn Glu Cys Met Glu Ser Val Arg Asn Gly Thr Tyr Asp Tyr Pro
145                 150                 155                 160

Gln Tyr Ser Glu Glu Ala Arg Leu Lys Arg Glu Glu Ile Ser Gly Val
                165                 170                 175

Lys Leu Glu Ser Ile Gly Thr Tyr Gln Ile Leu Ser Ile Tyr Ser Thr
                180                 185                 190

Val Ala Ser Ser Leu Ala Leu Ala Ile Met Val Ala Gly Leu Ser Leu
                195                 200                 205

Trp Met Cys Ser Asn Gly Ser Leu Gln Cys Arg Ile Cys Ile Gly Tyr
            210                 215                 220

Ile Pro Glu Ala Pro Arg Asp Gly Gln Ala Tyr Val Arg Lys Asp Gly
225                 230                 235                 240

Glu Trp Val Leu Leu Ser Thr Phe Leu Arg Ser Ser Lys Pro Thr Cys
                245                 250                 255

Pro Pro Pro Glu Leu Leu Gly Gly Pro Ser Val Phe Ile Phe Pro Pro
                260                 265                 270

Lys Pro Lys Asp Thr Leu Met Ile Ser Arg Thr Pro Glu Val Thr Cys
                275                 280                 285

Val Val Val Asp Val Ser Gln Asp Asp Pro Glu Val Gln Phe Thr Trp
            290                 295                 300

Tyr Ile Asn Asn Glu Gln Val Arg Thr Ala Arg Pro Pro Leu Arg Glu
305                 310                 315                 320

Gln Gln Phe Asn Ser Thr Ile Arg Val Val Ser Thr Leu Pro Ile Ala
                325                 330                 335

His Gln Asp Trp Leu Arg Gly Lys Glu Phe Lys Cys Lys Val His Asn
                340                 345                 350

Lys Ala Leu Pro Ala Pro Ile Glu Lys Thr Ile Ser Lys Ala Arg Gly
                355                 360                 365

Gln Pro Leu Glu Pro Lys Val Tyr Thr Met Gly Pro Pro Arg Glu Glu
                370                 375                 380

Leu Ser Ser Arg Ser Val Ser Leu Thr Cys Met Ile Asn Gly Phe Tyr
385                 390                 395                 400

Pro Ser Asp Ile Ser Val Glu Trp Lys Asn Gly Lys Ala Glu Asp
                405                 410                 415

Asn Tyr Lys Thr Thr Pro Ala Val Leu Asp Ser Asp Gly Ser Tyr Phe
                420                 425                 430

Leu Tyr Ser Lys Leu Ser Val Pro Thr Ser Glu Trp Gln Arg Gly Asp
                435                 440                 445

Val Phe Thr Cys Ser Val Met His Glu Ala Leu His Asn His Tyr Thr
            450                 455                 460

Gln Lys Ser Ile Ser Arg Ser Pro Gly Lys
465                 470

<210> SEQ ID NO 29
<211> LENGTH: 407
<212> TYPE: PRT
<213> ORGANISM: Artificial Sequence
<220> FEATURE:
<223> OTHER INFORMATION: HA-RBD-Fd-rFc fusion protein
```

<400> SEQUENCE: 29

```
Leu Ser Arg Ile Asn His Phe Glu Lys Ile Gln Ile Ile Pro Lys Ser
1               5                   10                  15
Ser Trp Ser Asp His Glu Ala Ser Ser Gly Val Ser Ser Ala Cys Pro
            20                  25                  30
Tyr Gln Gly Thr Pro Ser Phe Phe Arg Asn Val Val Trp Leu Ile Lys
        35                  40                  45
Lys Asn Asn Thr Tyr Pro Thr Ile Lys Arg Ser Tyr Asn Asn Thr Asn
    50                  55                  60
Gln Glu Asp Leu Leu Ile Leu Trp Gly Ile His His Ser Asn Asp Ala
65                  70                  75                  80
Ala Glu Gln Thr Lys Leu Tyr Gln Asn Pro Thr Thr Tyr Ile Ser Val
                85                  90                  95
Gly Thr Ser Thr Leu Asn Gln Arg Leu Val Pro Lys Ile Ala Thr Arg
            100                 105                 110
Ser Lys Val Asn Gly Gln Asn Gly Arg Met Asp Phe Phe Trp Thr Ile
        115                 120                 125
Leu Lys Pro Asn Asp Ala Ile Asn Phe Glu Ser Asn Gly Asn Phe Ile
    130                 135                 140
Ala Pro Glu Tyr Ala Tyr Lys Ile Val Lys Lys Gly Tyr Ile Pro Glu
145                 150                 155                 160
Ala Pro Arg Asp Gly Gln Ala Tyr Val Arg Lys Asp Gly Glu Trp Val
                165                 170                 175
Leu Leu Ser Thr Phe Leu Arg Ser Ser Lys Pro Thr Cys Pro Pro Pro
            180                 185                 190
Glu Leu Leu Gly Gly Pro Ser Val Phe Ile Phe Pro Pro Lys Pro Lys
        195                 200                 205
Asp Thr Leu Met Ile Ser Arg Thr Pro Glu Val Thr Cys Val Val Val
    210                 215                 220
Asp Val Ser Gln Asp Asp Pro Glu Val Gln Phe Thr Trp Tyr Ile Asn
225                 230                 235                 240
Asn Glu Gln Val Arg Thr Ala Arg Pro Pro Leu Arg Glu Gln Gln Phe
                245                 250                 255
Asn Ser Thr Ile Arg Val Val Ser Thr Leu Pro Ile Ala His Gln Asp
            260                 265                 270
Trp Leu Arg Gly Lys Glu Phe Lys Cys Lys Val His Asn Lys Ala Leu
        275                 280                 285
Pro Ala Pro Ile Glu Lys Thr Ile Ser Lys Ala Arg Gly Gln Pro Leu
    290                 295                 300
Glu Pro Lys Val Tyr Thr Met Gly Pro Pro Arg Glu Glu Leu Ser Ser
305                 310                 315                 320
Arg Ser Val Ser Leu Thr Cys Met Ile Asn Gly Phe Tyr Pro Ser Asp
                325                 330                 335
Ile Ser Val Glu Trp Glu Lys Asn Gly Lys Ala Glu Asp Asn Tyr Lys
            340                 345                 350
Thr Thr Pro Ala Val Leu Asp Ser Asp Gly Ser Tyr Phe Leu Tyr Ser
        355                 360                 365
Lys Leu Ser Val Pro Thr Ser Glu Trp Gln Arg Gly Asp Val Phe Thr
    370                 375                 380
Cys Ser Val Met His Glu Ala Leu His Asn His Tyr Thr Gln Lys Ser
385                 390                 395                 400
Ile Ser Arg Ser Pro Gly Lys
                405
```

<210> SEQ ID NO 30
<211> LENGTH: 257
<212> TYPE: PRT
<213> ORGANISM: Influenza virus

<400> SEQUENCE: 30

Ile Cys Ile Gly Tyr His Ala Asn Asn Ser Thr Glu Gln Val Asp Thr
1               5                   10                  15

Ile Met Glu Lys Asn Val Thr Val Thr His Ala Gln Asp Ile Leu Glu
            20                  25                  30

Lys Thr His Asn Gly Lys Leu Cys Asp Leu Asp Gly Val Lys Pro Leu
        35                  40                  45

Ile Leu Arg Asp Cys Ser Val Ala Gly Trp Leu Leu Gly Asn Pro Met
    50                  55                  60

Cys Asp Glu Phe Ile Asn Val Pro Glu Trp Ser Tyr Ile Val Glu Lys
65                  70                  75                  80

Ala Asn Pro Ala Asn Asp Leu Cys Tyr Pro Gly Asn Phe Asn Asp Tyr
                85                  90                  95

Glu Glu Leu Lys His Leu Leu Ser Arg Ile Asn His Phe Glu Lys Ile
            100                 105                 110

Gln Ile Ile Pro Lys Ser Ser Trp Ser Asp His Glu Ala Ser Ser Gly
        115                 120                 125

Val Ser Ser Ala Cys Pro Tyr Gln Gly Thr Pro Ser Phe Phe Arg Asn
    130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
            180                 185                 190

Thr Thr Tyr Ile Ser Val Gly Thr Ser Thr Leu Asn Gln Arg Leu Val
        195                 200                 205

Pro Lys Ile Ala Thr Arg Ser Lys Val Asn Gly Gln Asn Gly Arg Met
    210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys

<210> SEQ ID NO 31
<211> LENGTH: 284
<212> TYPE: PRT
<213> ORGANISM: Artificial Sequence
<220> FEATURE:
<223> OTHER INFORMATION: HA1(+3-259)-Fd fusion protein

<400> SEQUENCE: 31

Ile Cys Ile Gly Tyr His Ala Asn Asn Ser Thr Glu Gln Val Asp Thr
1               5                   10                  15

Ile Met Glu Lys Asn Val Thr Val Thr His Ala Gln Asp Ile Leu Glu
            20                  25                  30

Lys Thr His Asn Gly Lys Leu Cys Asp Leu Asp Gly Val Lys Pro Leu
        35                  40                  45

Ile Leu Arg Asp Cys Ser Val Ala Gly Trp Leu Leu Gly Asn Pro Met

```
            50                  55                  60
Cys Asp Glu Phe Ile Asn Val Pro Glu Trp Ser Tyr Ile Val Glu Lys
 65                  70                  75                  80

Ala Asn Pro Ala Asn Asp Leu Cys Tyr Pro Gly Asn Phe Asn Asp Tyr
                 85                  90                  95

Glu Glu Leu Lys His Leu Leu Ser Arg Ile Asn His Phe Glu Lys Ile
            100                 105                 110

Gln Ile Ile Pro Lys Ser Ser Trp Ser Asp His Glu Ala Ser Ser Gly
            115                 120                 125

Val Ser Ser Ala Cys Pro Tyr Gln Gly Thr Pro Ser Phe Phe Arg Asn
            130                 135                 140

Val Val Trp Leu Ile Lys Lys Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
            180                 185                 190

Thr Thr Tyr Ile Ser Val Gly Thr Ser Thr Leu Asn Gln Arg Leu Val
            195                 200                 205

Pro Lys Ile Ala Thr Arg Ser Lys Val Asn Gly Gln Asn Gly Arg Met
210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys Gly Tyr Ile Pro Glu Ala Pro Arg Asp Gly Gln Ala Tyr Val Arg
            260                 265                 270

Lys Asp Gly Glu Trp Val Leu Leu Ser Thr Phe Leu
            275                 280

<210> SEQ ID NO 32
<211> LENGTH: 486
<212> TYPE: PRT
<213> ORGANISM: Artificial Sequence
<220> FEATURE:
<223> OTHER INFORMATION: HA1(+3-259)-hFc fusion protein

<400> SEQUENCE: 32

Ile Cys Ile Gly Tyr His Ala Asn Asn Ser Thr Glu Gln Val Asp Thr
  1               5                  10                  15

Ile Met Glu Lys Asn Val Thr Val Thr His Ala Gln Asp Ile Leu Glu
                 20                  25                  30

Lys Thr His Asn Gly Lys Leu Cys Asp Leu Asp Gly Val Lys Pro Leu
             35                  40                  45

Ile Leu Arg Asp Cys Ser Val Ala Gly Trp Leu Leu Gly Asn Pro Met
 50                  55                  60

Cys Asp Glu Phe Ile Asn Val Pro Glu Trp Ser Tyr Ile Val Glu Lys
 65                  70                  75                  80

Ala Asn Pro Ala Asn Asp Leu Cys Tyr Pro Gly Asn Phe Asn Asp Tyr
                 85                  90                  95

Glu Glu Leu Lys His Leu Leu Ser Arg Ile Asn His Phe Glu Lys Ile
            100                 105                 110

Gln Ile Ile Pro Lys Ser Ser Trp Ser Asp His Glu Ala Ser Ser Gly
            115                 120                 125

Val Ser Ser Ala Cys Pro Tyr Gln Gly Thr Pro Ser Phe Phe Arg Asn
```

-continued

```
                130                 135                 140
Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
                180                 185                 190

Thr Thr Tyr Ile Ser Val Gly Thr Ser Thr Leu Asn Gln Arg Leu Val
                195                 200                 205

Pro Lys Ile Ala Thr Arg Ser Lys Val Asn Gly Gln Asn Gly Arg Met
210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys Arg Ser Asp Lys Thr His Thr Cys Pro Pro Cys Pro Ala Pro Glu
                260                 265                 270

Leu Leu Gly Gly Pro Ser Val Phe Leu Phe Pro Pro Lys Pro Lys Asp
                275                 280                 285

Thr Leu Met Ile Ser Arg Thr Pro Glu Val Thr Cys Val Val Val Asp
                290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
                340                 345                 350

Leu Asn Gly Lys Glu Tyr Lys Cys Lys Val Ser Asn Lys Ala Leu Pro
                355                 360                 365

Ala Pro Ile Glu Lys Thr Ile Ser Lys Ala Lys Gly Gln Pro Arg Glu
370                 375                 380

Pro Gln Val Tyr Thr Leu Pro Pro Ser Arg Glu Glu Met Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
                420                 425                 430

Thr Pro Pro Val Leu Asp Ser Asp Gly Ser Phe Phe Leu Tyr Ser Lys
                435                 440                 445

Leu Thr Val Asp Lys Ser Arg Trp Gln Gln Gly Asn Val Phe Ser Cys
450                 455                 460

Ser Val Met His Glu Ala Leu His Asn His Tyr Thr Gln Lys Ser Leu
465                 470                 475                 480

Ser Leu Ser Pro Gly Lys
                485
```

<210> SEQ ID NO 33
<211> LENGTH: 513
<212> TYPE: PRT
<213> ORGANISM: Artificial Sequence
<220> FEATURE:
<223> OTHER INFORMATION: HA1(+3-259)-Fd-hFc fusion protein

<400> SEQUENCE: 33

Ile Cys Ile Gly Tyr His Ala Asn Asn Ser Thr Glu Gln Val Asp Thr

-continued

```
1               5                   10                  15
Ile Met Glu Lys Asn Val Thr Val Thr His Ala Gln Asp Ile Leu Glu
                20                  25                  30
Lys Thr His Asn Gly Lys Leu Cys Asp Leu Asp Gly Val Lys Pro Leu
                35                  40                  45
Ile Leu Arg Asp Cys Ser Val Ala Gly Trp Leu Leu Gly Asn Pro Met
    50                  55                  60
Cys Asp Glu Phe Ile Asn Val Pro Glu Trp Ser Tyr Ile Val Glu Lys
65                  70                  75                  80
Ala Asn Pro Ala Asn Asp Leu Cys Tyr Pro Gly Asn Phe Asn Asp Tyr
                85                  90                  95
Glu Glu Leu Lys His Leu Leu Ser Arg Ile Asn His Phe Glu Lys Ile
                100                 105                 110
Gln Ile Ile Pro Lys Ser Ser Trp Ser Asp His Glu Ala Ser Ser Gly
                115                 120                 125
Val Ser Ser Ala Cys Pro Tyr Gln Gly Thr Pro Ser Phe Phe Arg Asn
                130                 135                 140
Val Val Trp Leu Ile Lys Lys Asn Asn Thr Tyr Pro Thr Ile Lys Arg
145                 150                 155                 160
Ser Tyr Asn Asn Thr Asn Gln Glu Asp Leu Leu Ile Leu Trp Gly Ile
                165                 170                 175
His His Ser Asn Asp Ala Ala Glu Gln Thr Lys Leu Tyr Gln Asn Pro
                180                 185                 190
Thr Thr Tyr Ile Ser Val Gly Thr Ser Thr Leu Asn Gln Arg Leu Val
                195                 200                 205
Pro Lys Ile Ala Thr Arg Ser Lys Val Asn Gly Gln Asn Gly Arg Met
                210                 215                 220
Asp Phe Phe Trp Thr Ile Leu Lys Pro Asn Asp Ala Ile Asn Phe Glu
225                 230                 235                 240
Ser Asn Gly Asn Phe Ile Ala Pro Glu Tyr Ala Tyr Lys Ile Val Lys
                245                 250                 255
Lys Gly Tyr Ile Pro Glu Ala Pro Arg Asp Gly Gln Ala Tyr Val Arg
                260                 265                 270
Lys Asp Gly Glu Trp Val Leu Leu Ser Thr Phe Leu Arg Ser Asp Lys
                275                 280                 285
Thr His Thr Cys Pro Pro Cys Pro Ala Pro Glu Leu Leu Gly Gly Pro
                290                 295                 300
Ser Val Phe Leu Phe Pro Pro Lys Pro Lys Asp Thr Leu Met Ile Ser
305                 310                 315                 320
Arg Thr Pro Glu Val Thr Cys Val Val Val Asp Val Ser His Glu Asp
                325                 330                 335
Pro Glu Val Lys Phe Asn Trp Tyr Val Asp Gly Val Glu Val His Asn
                340                 345                 350
Ala Lys Thr Lys Pro Arg Glu Glu Gln Tyr Asn Ser Thr Tyr Arg Val
                355                 360                 365
Val Ser Val Leu Thr Val Leu His Gln Asp Trp Leu Asn Gly Lys Glu
                370                 375                 380
Tyr Lys Cys Lys Val Ser Asn Lys Ala Leu Pro Ala Pro Ile Glu Lys
385                 390                 395                 400
Thr Ile Ser Lys Ala Lys Gly Gln Pro Arg Glu Pro Gln Val Tyr Thr
                405                 410                 415
Leu Pro Pro Ser Arg Glu Glu Met Thr Lys Asn Gln Val Ser Leu Thr
                420                 425                 430
```

```
Cys Leu Val Lys Gly Phe Tyr Pro Ser Asp Ile Ala Val Glu Trp Glu
        435                 440                 445

Ser Asn Gly Gln Pro Glu Asn Asn Tyr Lys Thr Thr Pro Pro Val Leu
450                 455                 460

Asp Ser Asp Gly Ser Phe Phe Leu Tyr Ser Lys Leu Thr Val Asp Lys
465                 470                 475                 480

Ser Arg Trp Gln Gln Gly Asn Val Phe Ser Cys Ser Val Met His Glu
        485                 490                 495

Ala Leu His Asn His Tyr Thr Gln Lys Ser Leu Ser Leu Ser Pro Gly
        500                 505                 510

Lys

<210> SEQ ID NO 34
<211> LENGTH: 518
<212> TYPE: PRT
<213> ORGANISM: Artificial Sequence
<220> FEATURE:
<223> OTHER INFORMATION: HA1(+3-259)-Fd-mFc fusion protein

<400> SEQUENCE: 34

Ile Cys Ile Gly Tyr His Ala Asn Asn Ser Thr Glu Gln Val Asp Thr
1               5                   10                  15

Ile Met Glu Lys Asn Val Thr Val Thr His Ala Gln Asp Ile Leu Glu
                20                  25                  30

Lys Thr His Asn Gly Lys Leu Cys Asp Leu Asp Gly Val Lys Pro Leu
            35                  40                  45

Ile Leu Arg Asp Cys Ser Val Ala Gly Trp Leu Leu Gly Asn Pro Met
50                  55                  60

Cys Asp Glu Phe Ile Asn Val Pro Glu Trp Ser Tyr Ile Val Glu Lys
65                  70                  75                  80

Ala Asn Pro Ala Asn Asp Leu Cys Tyr Pro Gly Asn Phe Asn Asp Tyr
                85                  90                  95

Glu Glu Leu Lys His Leu Leu Ser Arg Ile Asn His Phe Glu Lys Ile
            100                 105                 110

Gln Ile Ile Pro Lys Ser Ser Trp Ser Asp His Glu Ala Ser Ser Gly
        115                 120                 125

Val Ser Ser Ala Cys Pro Tyr Gln Gly Thr Pro Ser Phe Phe Arg Asn
130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
            180                 185                 190

Thr Thr Tyr Ile Ser Val Gly Thr Ser Thr Leu Asn Gln Arg Leu Val
        195                 200                 205

Pro Lys Ile Ala Thr Arg Ser Lys Val Asn Gly Gln Asn Gly Arg Met
210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys Gly Tyr Ile Pro Glu Ala Pro Arg Asp Gly Gln Ala Tyr Val Arg
            260                 265                 270
```

```
Lys Asp Gly Glu Trp Val Leu Leu Ser Thr Phe Leu Arg Ser Pro Arg
                275                 280                 285

Gly Pro Thr Ile Lys Pro Cys Pro Pro Cys Lys Cys Pro Ala Pro Asn
            290                 295                 300

Leu Leu Gly Gly Pro Ser Val Phe Ile Phe Pro Pro Lys Ile Lys Asp
305                 310                 315                 320

Val Leu Met Ile Ser Leu Ser Pro Ile Val Thr Cys Val Val Val Asp
                325                 330                 335

Val Ser Glu Asp Asp Pro Asp Val Gln Ile Ser Trp Phe Val Asn Asn
            340                 345                 350

Val Glu Val His Thr Ala Gln Thr Gln Thr His Arg Glu Asp Tyr Asn
            355                 360                 365

Ser Thr Leu Arg Val Val Ser Ala Leu Pro Ile Gln His Gln Asp Trp
            370                 375                 380

Met Ser Gly Lys Glu Phe Lys Cys Lys Val Asn Asn Lys Asp Leu Pro
385                 390                 395                 400

Ala Pro Ile Glu Arg Thr Ile Ser Lys Pro Lys Gly Ser Val Arg Ala
                405                 410                 415

Pro Gln Val Tyr Val Leu Pro Pro Glu Glu Glu Met Thr Lys Lys
            420                 425                 430

Gln Val Thr Leu Thr Cys Met Val Thr Asp Phe Met Pro Glu Asp Ile
            435                 440                 445

Tyr Val Glu Trp Thr Asn Asn Gly Lys Thr Glu Leu Asn Tyr Lys Asn
            450                 455                 460

Thr Glu Pro Val Leu Asp Ser Asp Gly Ser Tyr Phe Met Tyr Ser Lys
465                 470                 475                 480

Leu Arg Val Glu Lys Lys Asn Trp Val Glu Arg Asn Ser Tyr Ser Cys
                485                 490                 495

Ser Val Val His Glu Gly Leu His Asn His His Thr Thr Lys Ser Phe
            500                 505                 510

Ser Arg Thr Pro Gly Lys
            515

<210> SEQ ID NO 35
<211> LENGTH: 509
<212> TYPE: PRT
<213> ORGANISM: Artificial Sequence
<220> FEATURE:
<223> OTHER INFORMATION: HA1(+3-259)-Fd-rFc fusion protein

<400> S

```
Gln Ile Ile Pro Lys Ser Ser Trp Ser Asp His Glu Ala Ser Ser Gly
            115                 120                 125

Val Ser Ser Ala Cys Pro Tyr Gln Gly Thr Pro Ser Phe Phe Arg Asn
130                 135                 140

Val Val Trp Leu Ile Lys Lys Asn Asn Thr Tyr Pro Thr Ile Lys Arg
145                 150                 155                 160

Ser Tyr Asn Asn Thr Asn Gln Glu Asp Leu Leu Ile Leu Trp Gly Ile
                165                 170                 175

His His Ser Asn Asp Ala Ala Glu Gln Thr Lys Leu Tyr Gln Asn Pro
            180                 185                 190

Thr Thr Tyr Ile Ser Val Gly Thr Ser Thr Leu Asn Gln Arg Leu Val
        195                 200                 205

Pro Lys Ile Ala Thr Arg Ser Lys Val Asn Gly Gln Asn Gly Arg Met
    210                 215                 220

Asp Phe Phe Trp Thr Ile Leu Lys Pro Asn Asp Ala Ile Asn Phe Glu
225                 230                 235                 240

Ser Asn Gly Asn Phe Ile Ala Pro Glu Tyr Ala Tyr Lys Ile Val Lys
                245                 250                 255

Lys Gly Tyr Ile Pro Glu Ala Pro Arg Asp Gly Gln Ala Tyr Val Arg
            260                 265                 270

Lys Asp Gly Glu Trp Val Leu Leu Ser Thr Phe Leu Arg Ser Ser Lys
        275                 280                 285

Pro Thr Cys Pro Pro Glu Leu Leu Gly Gly Pro Ser Val Phe Ile
    290                 295                 300

Phe Pro Pro Lys Pro Lys Asp Thr Leu Met Ile Ser Arg Thr Pro Glu
305                 310                 315                 320

Val Thr Cys Val Val Val Asp Val Ser Gln Asp Asp Pro Glu Val Gln
                325                 330                 335

Phe Thr Trp Tyr Ile Asn Asn Glu Gln Val Arg Thr Ala Arg Pro Pro
            340                 345                 350

Leu Arg Glu Gln Gln Phe Asn Ser Thr Ile Arg Val Val Ser Thr Leu
        355                 360                 365

Pro Ile Ala His Gln Asp Trp Leu Arg Gly Lys Glu Phe Lys Cys Lys
    370                 375                 380

Val His Asn Lys Ala Leu Pro Ala Pro Ile Glu Lys Thr Ile Ser Lys
385                 390                 395                 400

Ala Arg Gly Gln Pro Leu Glu Pro Lys Val Tyr Thr Met Gly Pro Pro
                405                 410                 415

Arg Glu Glu Leu Ser Ser Arg Ser Val Ser Leu Thr Cys Met Ile Asn
            420                 425                 430

Gly Phe Tyr Pro Ser Asp Ile Ser Val Glu Trp Glu Lys Asn Gly Lys
        435                 440                 445

Ala Glu Asp Asn Tyr Lys Thr Thr Pro Ala Val Leu Asp Ser Asp Gly
    450                 455                 460

Ser Tyr Phe Leu Tyr Ser Lys Leu Ser Val Pro Thr Ser Glu Trp Gln
465                 470                 475                 480

Arg Gly Asp Val Phe Thr Cys Ser Val Met His Glu Ala Leu His Asn
                485                 490                 495

His Tyr Thr Gln Lys Ser Ile Ser Arg Ser Pro Gly Lys
            500                 505

<210> SEQ ID NO 36
<211> LENGTH: 29
<212> TYPE: PRT
```

<213> ORGANISM: Bacteriophage T4

<400> SEQUENCE: 36

Gly Ser Gly Tyr Ile Pro Glu Ala Pro Arg Asp Gly Gln Ala Tyr Val
1               5                   10                  15
Arg Lys Asp Gly Glu Trp Val Leu Leu Ser Thr Phe Leu
            20                  25

<210> SEQ ID NO 37
<211> LENGTH: 32
<212> TYPE: PRT
<213> ORGANISM: Artificial Sequence
<220> FEATURE:
<223> OTHER INFORMATION: GCN4 stabilization sequence

<400> SEQUENCE: 37

Met Lys Gln Ile Glu Asp Lys Ile Glu Glu Ile Leu Ser Lys Ile Tyr
1               5                   10                  15
His Ile Glu Asn Glu Ile Ala Arg Ile Lys Lys Leu Ile Gly Glu Val
            20                  25                  30

<210> SEQ ID NO 38
<211> LENGTH: 28
<212> TYPE: PRT
<213> ORGANISM: Artificial Sequence
<220> FEATURE:
<223> OTHER INFORMATION: IQ stabilization sequence

<400> SEQUENCE: 38

Arg Met Lys Gln Ile Glu Asp Lys Ile Glu Glu Ile Glu Ser Lys Gln
1               5                   10                  15
Lys Lys Ile Glu Asn Glu Ile Ala Arg Ile Lys Lys
            20                  25

<210> SEQ ID NO 39
<211> LENGTH: 24
<212> TYPE: PRT
<213> ORGANISM: Artificial Sequence
<220> FEATURE:
<223> OTHER INFORMATION: IZ stabilization sequence

<400> SEQUENCE: 39

Ile Lys Lys Glu Ile Glu Ala Ile Lys Lys Glu Gln Glu Ala Ile Lys
1               5                   10                  15
Lys Lys Ile Glu Ala Ile Glu Lys
            20

<210> SEQ ID NO 40
<211> LENGTH: 81
<212> TYPE: DNA
<213> ORGANISM: Bacteriophage T4

<400> SEQUENCE: 40
ggctatattc cggaagcgcc gcgtgatggc caggcgtatg tgcgtaaaga tggcgaatgg      60
gtgctgctgt ctacctttct g                                               81

<210> SEQ ID NO 41
<211> LENGTH: 7
<212> TYPE: PRT
<213> ORGANISM: Artificial Sequence
<220> FEATURE:
<223> OTHER INFORMATION: protease cleavage site

<400> SEQUENCE: 41

Arg Glu Arg Arg Arg Lys Arg
1               5

<210> SEQ ID NO 42
<211> LENGTH: 9
<212> TYPE: DNA
<213> ORGANISM: Artificial Sequence
<220> FEATURE:
<223> OTHER INFORMATION: Primer

<400> SEQUENCE: 42 agcaaaagc                                                                 9

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
tgtcaagaaa ggagactcag c                                                  21

<210> SEQ ID NO 44
<211> LENGTH: 19
<212> TYPE: DNA
<213> ORGANISM: Artificial Sequence
<220> FEATURE:
<223> OTHER INFORMATION: Primer

<400> SEQUENCE: 44
accatctacc attccctgc                                                     19

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
atacaccctc tcaccatcgg                                                    20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
accatctacc attccctgcc                                                    20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
atacaccctc tcaccatcgg                                                    20

<210> SEQ ID NO 48
<211> LENGTH: 19

-continued

```
<212> TYPE: DNA
<213> ORGANISM: Artificial Sequence
<220> FEATURE:
<223> OTHER INFORMATION: Primer

<400> SEQUENCE: 48
accatctacc attccctgc                                                   19
```

IMMUNOPOTENTIATOR-LINKED OLIGOMERIC INFLUENZA IMMUNOGENIC COMPOSITIONS

CROSS-REFERENCE TO RELATED APPLICATIONS

This application is a division of U.S. patent application Ser. No. 12/897,997, filed Oct. 5, 2010, which claims the benefit under 35 U.S.C. § 119(e) to U.S. Provisional Patent Application No. 61/250,442 filed Oct. 9, 2009, the entire contents of all of which are incorporated by reference herein.

FIELD OF THE INVENTION

The present disclosure relates to the field of immunogenic compositions for the prevention of influenza infection.

BACKGROUND OF THE INVENTION

The Influenza A virus, which belongs to the Orthomyxoviridae family, can cause influenza in humans, birds or domesticated food animals. The virus can be classified into different subtypes based on their surface glycoproteins, hemagglutinin (HA) and neuraminidase (NA). Of the 16 known HAs and nine NAs, three HA subtypes (H1, H2, and H3) and two NA subtypes (N1 and N2) are most commonly found in humans. H1N1 and H3N2 are the major subtypes that cause human seasonal flu and global pandemics of influenza. The influenza pandemic in 2009 is caused by influenza A virus H1N1 of swine origin. This has led to a growing concern regarding the pandemic potential of the highly pathogenic avian influenza (HPAI) H5N1 viruses. Thus the development of an effective and safe vaccine against divergent influenza A virus strains is urgently needed for the prevention of future outbreaks of influenza.

SUMMARY OF THE INVENTION

Disclosed herein are immunogenic compositions for the prevention of infection with influenza viruses. The disclosed immunogenic compositions are trimeric proteins comprising: 1) an immunogen, such as an influenza hemagluttinin sequence; 2) a trimerization or stabilization sequence; and 3) an immunopotentiator sequence. The three sequences are contiguous and expressed as a single protein in a mammalian expression system or the immunogen and the immunogen and the immunopotentiator are chemically linked and stabilized.

In one embodiment, disclosed herein is an immunogenic composition for induction of an immune response against influenza virus, the immunogenic composition comprising a polypeptide comprising an immunogen and an immunopotentiator. In another embodiment, the polypeptide further comprises a stabilization sequence.

In other embodiments, the immunogen is a hemagglutinin sequence of an influenza virus, a neuraminidase sequence of an influenza virus or a membrane protein sequence of an influenza virus. In another embodiment, the immunogen is a fragment of said hemagglutinin sequence selected from the group consisting of HA1, HA2 and RBD. In another embodiment, the immunopotentiator is selected from the group consisting of the Fc fragment of human IgG, C3d, Onchocerca volvulus ASP-1, cholera toxin and muramyl peptides.

In another embodiment, the stabilization sequence is foldon or GCN4.

In yet another embodiment, the polypeptide is a fusion protein. In another embodiment, the polypeptide is produced in a mammalian expression system.

In another embodiment, the polypeptide is selected from the group consisting of HA1-hFc, HA-hFc, HA1+3-259-hFc, HA1-Fd-hFc, HA-Fd-hFc, HA2-Fd-hFc, HA-RBD-Fd-hFc, and HA1+3-259-Fd-hFc.

In another embodiment, the immunogen is linked to said stabilization sequence and wherein said stabilization sequence is linked to the immunopotentiator in a single polypeptide. In yet another embodiment, the immunogen and the immunopotentiator are chemically stabilized by 2,2-bipyridine-5-carboxylic acid (BPY).

In still another embodiment, the immunogenic composition further comprises an adjuvant.

Also disclosed herein is a method of inducing a protective immune response against an influenza virus, the method comprising administering the immunogenic composition of claim 1 to a host in need thereof and wherein the immunogenic composition induces a protective immune response against challenge with an infectious agent in the host. In another embodiment, the immunogenic composition further comprises an adjuvant.

BRIEF DESCRIPTION OF THE DRAWINGS

FIG. 16 depicts the neutralizing Ab titers ($NT_{50}$)) against HA of heterologous (HK-HA, 1194-HA, QH-HA and XJ-HA) and homologous (AH-HA) strains of H5N1 pseudovirus, detected in sera of mice at 10 days post last vaccination with HA1-hFc, and HA1-Fd-hFc.

FIG. 17 depicts the neutralizing Ab titers ($NT_{50}$)) against HA of heterologous (HK-HA, 1194-HA) and homologous (AH-HA) strains of H5N1 pseudovirus, detected in sera of mice at 10 days post last vaccination with HA-3-259-Fd-hFc protein.

DEFINITION OF TERMS

Figure 1:
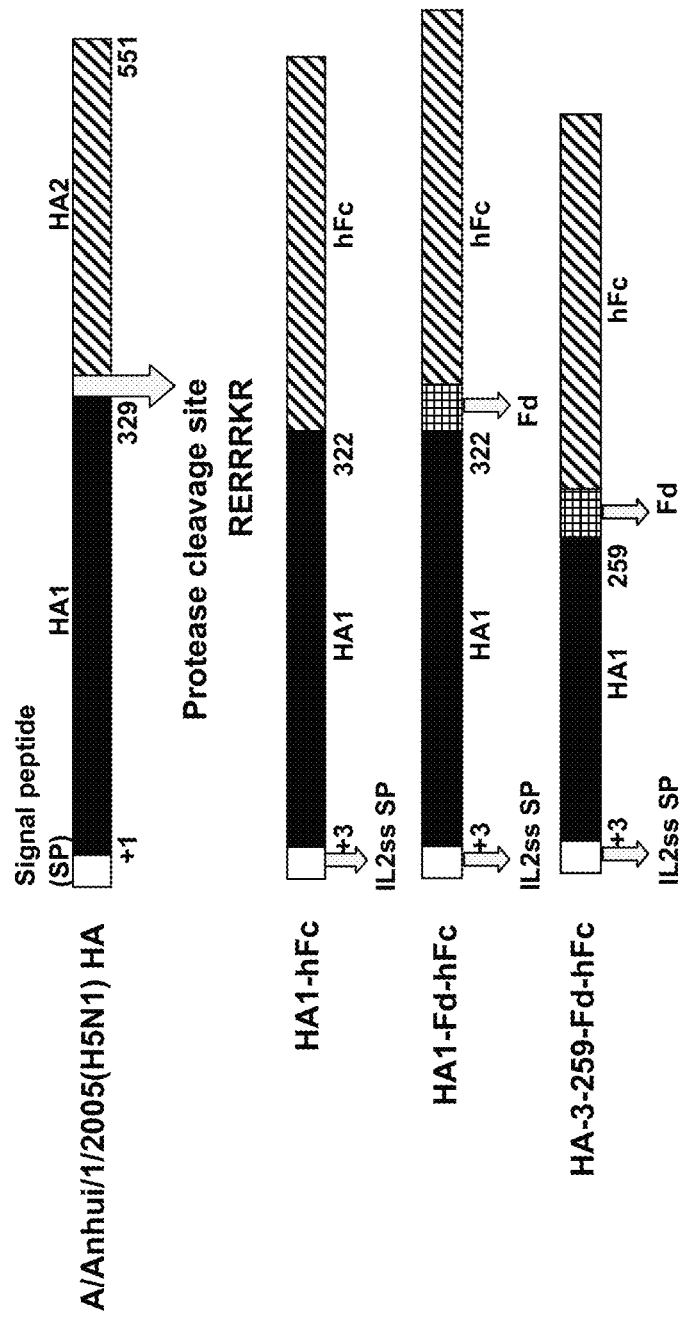
FIG. 1 depicts the structure of the hemagluttinin (HA) protein of an influenza A H5N1 virus [A/Anhui/1/2005 (H5N1)] and the construction of the recombinant HA1-hFc and HA1-Fd-hFc proteins containing the HA1 fragment (amino acids [aa] +3-322), and the recombinant HA-3-259-Fd-hFc protein including HA1 fragment of aa+3-259 of H5N1 virus HA fused to human IgG Fc (hFc), with or without the Fd sequence. The protease cleavage site RERRRKR between HA1 and HA2 is set forth as SEQ ID NO:41.

To facilitate an understanding of the following Detailed Description, Examples and appended claims it may be useful to refer to the following definitions. These definitions are non-limiting in nature and are supplied merely as a convenience to the reader.

Gene: A "gene" as used herein refers to at least a portion of a genetic construct having a promoter and/or other regulatory sequences required for, or that modify the expression of, the genetic construct.

Host: As used herein "host" refers to the recipient of the present immunogenic compositions. Exemplary hosts are mammals including, but not limited to, primates, rodents, cows, horses, dogs, cats, sheep, goats, pigs and elephants. In one embodiment of the present invention the host is a human. For the purposes of this disclosure host is synonymous with "vaccinee."

Immunogen: As used herein the term "immunogen" refers to any substrate that elicits an immune response in a host. Immunogens of the present disclosure include, but are not limited to hemaglutinins of influenza viruses.

Immunogenic Composition: As used herein an "immunogenic composition" refers to an expressed protein or a recombinant vector, with or without an adjuvant, which expresses and/or secretes an immunogen in vivo and wherein the immunogen elicits an immune response in the host. The immunogenic compositions disclosed herein may or may not be immunoprotective or therapeutic. When the immunogenic compositions may prevent, ameliorate, palliate or eliminate disease from the host then the immunogenic composition may optionally be referred to as a vaccine. However, the term immunogenic composition is not intended to be limited to vaccines.

DETAILED DESCRIPTION OF THE INVENTION

Development of an effective and safe vaccine against divergent influenza A viruses is urgently needed for the prevention of future outbreak of influenza, especially the pandemic potential of the divergent strains of highly pathogenic avian influenza (HPAI) H5N1 viruses. The present disclosure describes the development of a subunit influenza vaccine based on the surface hemagglutinin (HA) proteins of an influenza A virus. This candidate vaccine uses mammalian cell-expressed recombinant proteins encoding the HA1 fragment of HA. It induced strong immune responses, potent neutralizing antibodies and extensive cross-protective immunity in vaccinated animals. The elicited neutralizing antibodies were proven to be effective against at least five strains of pseudotyped influenza A virus isolates representing clades 0, 1, 2.2, and 2.3, and neutralize and cross-protect against at least three strains of live H5N1 influenza viruses covering clade 0, 1 and 2.3.4.

In one embodiment disclosed herein, provided is a subunit influenza vaccine (immunogenic composition) comprising a hemagglutinin (HA) of an influenza virus, a stabilization sequence and an immunopotentiator. In another embodiment, the immunogenic composition is expressed in a mammalian expression system.

A universal influenza vaccine that could provide heterosubtypic immunity would be a tremendous advance for public health. Disclosed herein is a candidate influenza vaccine, using mammalian 293T cell-expressed fusion proteins encoding the HA1 fragment (residues +3-322, SEQ ID NO. 2, and residues +3-259, SEQ ID NO. 30, respectively) of an influenza A H5N1 virus [A/Anhui/1/2005(H5N1)]. The expressed recombinant protein was fused with a foldon (Fd) sequence (SEQ ID NO. 6) and the Fc fragment (SEQ ID NO. 7) of human IgG1 (hFc), with the purpose to maintain the trimerization structure of native HA proteins and to increase the stability and immunogenicity. Foldon is a trimerization or oligomerization motif from the T4 bacteriophage fibritin. HA is a homotrimeric integral membrane glycoprotein. It is shaped like a cylinder, and is approximately 13.5 nanometers long. The three identical monomers that constitute HA are constructed into a central a helix coil; three spherical heads contain the sialic acid binding sites. HA monomers are synthesized as precursors that are then glycosylated and cleaved into two smaller polypeptides: the HA1 and HA2 subunits. Each HA monomer consists of a long, helical chain anchored in the membrane by HA2 and topped by a large HA1 globule.

In one embodiment, the immunopotentiator is an immunoglobulin Fc fragment. The immunoglobulin molecule consists of two light (L) chains and two heavy (H) chains held together by disulfide bonds such that the chains form a Y shape. The base of the Y (carboxyl terminus of the heavy chain) plays a role in modulating immune cell activity. This region is called the Fc (fragment, crystallizable) region, and is composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects including opsonization, cell lysis, and degranulation of mast cells, basophils and eosinophils.

The disclosed immunogenic compositions have high efficacy in inducing potent immune responses in tested animals. They are able to elicit highly potent neutralizing antibodies that could neutralize not only homologous A/Anhui/1/2005 (AH, clade 2.3) strains but also heterologous A/Hong Kong/156/97 (HK, clade 0), A/VietNam/1194/2004 (1194, clade 1), A/Xinjiang/1/2006 (XJ, clade 2.2), and A/Qinghai/59/05 (QH, clade 2.2) strains of H5N1 viruses expressing HA proteins in a cell culture-based pseudovirus neutralizing assay. In addition, the disclosed immunogenic compositions highly neutralize and completely cross-protect against at least three divergent strains of H5N1 live viruses, including clade 0: A/Hong Kong/156/97 (HK/156), clade 1: A/VietNam/1194/2004 (VN/1194) and clade 2.3.4: A/Shenzhen/406H/06 (SZ/406H). The above features demonstrate that the expressed fusion proteins have a high potential to be developed into a universal influenza vaccine for the prevention of future flu outbreaks.

Previously designed influenza HA-based vaccines could not induce highly potent and broad neutralizing responses in the hosts, most likely because these vaccines could not properly maintain the stable and soluble trimeric conformation, or they lack efficient immunogenicity to induce high levels of neutralizing antibodies. The presently described immunogenic compositions have solved these problems by: 1) addition of Fd, a trimerization motif, to HA1 allows the HA1 to properly maintain the stable and soluble trimeric conformation; and 2) fusion of Fc fragment of IgG to HA1-Fd which results in enhanced immunogenicity of HA1-trimer to induce high levels of neutralizing antibodies and cross-protection against a broad spectrum of influenza viruses. In addition, the Fc fragment has tendency to form a non-covalent dimer through its disulfide bond, which may allow the fusion protein to form a dimmer, hexamer or other form of oligomer, resulting in a more immunogenic molecule.

The ability to induce antibodies against divergent strains of a particular virus would solve the one strain-one vaccine problem that has been a significant hurdle for all manufacturers of flu vaccines. Furthermore, the described formulation does not utilize chicken eggs to grow the virus—a major advantage that not only significantly reduces manufacturing time and cost but also allows pregnant women and persons allergic to chicken egg proteins to receive the vaccine.

TABLE 1

Components that can be used for design of immunopotentiator-linked oligomeric Influenza vaccines

| Proteins of influenza viruses* | Stabilization molecule or method to form trimer or oligomer | Immunopotentiators or modulators |
|---|---|---|
| Hemagglutinin (HA) | GCN4 | cholera toxin |
| HA1 | Foldon | immunomodulators (such as cytokines) |
| HA2 | 2,2-bipyridine-5-carboxylic acid (BPY) | bacterial LPS |
| Peptides from HA1 | Disulfide bonds | Synthetic LPS mimetic RC529 |
| Peptides from HA2 | Facile ligation | muramyl peptides |
| Neuraminidase (NA) | | Monophosphoryl lipid A (MPL) |
| Peptides from NA | | dsRNA complexes |
| Membrane protein (M) | | CpG ODN, CTA1-DD |
| Peptides from M | | IgG Fc |
| HA receptor binding domain (RBD) | | C3d |
| | | ASP-1 |
| | | TGF-β or Th2 cytokines |

*including different subtypes.

In one embodiment, the influenza virus component of the instant immunogenic composition can comprise a sequence selected from the group consisting of the HA sequence of influenza virus H5N1; the HA sequence of influenza virus H1N1; the HA sequence of influenza virus H3N2; the HA1 sequence of influenza virus H5N1; the HA1 sequence of influenza virus H1N1; the HA1 sequence of influenza virus H3N2; the HA2 sequence of influenza virus H5N1; the HA2 sequence of influenza virus H1N1; the HA2 sequence of influenza virus H3N2; the NA sequence of influenza virus H5N1; the NA sequence of influenza virus H1N1; the NA sequence of influenza virus H3N2; the M1/M2 sequence of influenza virus H5N1; the M1/M2 sequence of influenza virus H1N1; the M1/M2 sequence of influenza virus H3N2; the HA-NA sequence of influenza virus H5N1; the HA-NA sequence of influenza virus H1N1; the HA-NA sequence of influenza virus H3N2; the HA-M1/M2 sequence of influenza virus H5N1; the HA-M1/M2 sequence of influenza virus H1N1; the HA-M1/M2 sequence of influenza virus H3N2; the HA-NA-M1/M2 sequence of influenza virus H5N1; the HA-NA-M1/M2 sequence of influenza virus H1N1; and the HA-NA-M1/M2 sequence of influenza virus H3N2. Amino acid and nucleic acid sequences for each of the above domains can be found in the Influenza Research Database.

TABLE 2

Amino acid and DNA sequences of immunopotentiator-linked oligomeric influenza immunogenic compositions (Note: SEQ ID NO. 40 and 42-48 are DNA sequences, while others are amino acid sequences)

SEQ ID NO. 1 [A/Anhui/1/2005(H5N1) HA]:
MEKIVLLLAIVSLVKSDQICIGYHANNSTEQVDTIMEKNVTVTHAQDILEKTHNGKLCDLDGVKPL
ILRDCSVAGWLLGNPMCDEFINVPEWSYIVEKANPANDLCYPGNFNDYEELKHLLSRINHFEKI
QIIPKSSWSDHEASSGVSSACPYQGTPSFFRNVVWLIKKNNTYPTIKRSYNNTNQEDLLILWGIH
HSNDAAEQTKLYQNPTTYISVGTSTLNQRLVPKIATRSKVNGQNGRMDFFWTILKPNDAINFES
NGNFIAPEYAYKIVKKGDSAIVKSEVEYGNCNTKCQTPIGAINSSMPFHNIHPLTIGECPKYVKSN
KLVLATGLRNSPLRERRRKRGLFGAIAGFIEGGWQGMVDGWYGYHHSNEQGSGYAADKEST
QKAIDGVTNKVNSIIDKMNTQFEAVGREFNNLERRIENLNKKMEDGFLDVWTYNAELLVLMENE
RTLDFHDSNVKNLYDKVRLQLRDNAKELGNGCFEFYHKCDNECMESVRNGTYDYPQYSEEAR
LKREEISGVKLESIGTYQILSIYSTVASSLALAIMVAGLSLWMCSNGSLQCRICI SEQ ID NO. 2 [A/Anhui/1/2005(H5N1) HA1 +3-322]:
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSGV
SSACPYQGTPSFFRNVVWLIKKNNTYPTIKRSYNNTNQEDLLILWGIHHSNDAAEQTKLYQNPT
TYISVGTSTLNQRLVPKIATRSKVNGQNGRMDFFWTILKPNDAINFESNGNFIAPEYAYKIVKKG
DSAIVKSEVEYGNCNTKCQTPIGAINSSMPFHNIHPLTIGECPKYVKSNKLVLATGLRNSPL SEQ ID NO. 3 [A/Anhui/1/2005(H5N1) HA2]:
GLFGAIAGFIEGGWQGMVDGWYGYHHSNEQGSGYAADKESTQKAIDGVTNKVNSIIDKMNTQ
FEAVGREFNNLERRIENLNKKMEDGFLDVWTYNAELLVLMENERTLDFHDSNVKNLYDKVRLQ
LRDNAKELGNGCFEFYHKCDNECMESVRNGTYDYPQYSEEARLKREEISGVKLESIGTYQILSI
YSTVASSLALAIMVAGLSLWMCSNGSLQCRICI SEQ ID NO. 4 [A/Anhui/1/2005(H5N1) HA-RBD]:
LSRINHFEKIQIIPKSSWSDHEASSGVSSACPYQGTPSFFRNVVWLIKKNNTYPTIKRSYNNTNQ
EDLLILWGIHHSNDAAEQTKLYQNPTTYISVGTSTLNQRLVPKIATRSKVNGQNGRMDFFWTILK
PNDAINFESNGNFIAPEYAYKIVKK SEQ ID NO. 5 [IL2ss signal peptide]:
MYRMQLLSCIALSLALVTNS SEQ ID NO. 6 [Foldon (Fd), also see SEQ ID NO. 36]:
GYIPEAPRDGQAYVRKDGEWVLLSTFL SEQ ID NO. 7 IgG Fc (hFc)1:
RSDKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTPPVLDSDGSFFLY
SKLTVDKSRWQQGNVFSCSVMHEALHNHYTQKSLSLSPGK SEQ ID NO. 8
MEKIVLLLAIVSLVKSDQICIGYHANNSTEQVDTIMEKNVTVTHAQDILEKTHNGKLCDLDGVKPL
ILRDCSVAGWLLGNPMCDEFINVPEWSYIVEKANPANDLCYPGNFNDYEELKHLLSRINHFEKI
QIIPKSSWSDHEASSGVSSACPYQGTPSFFRNVVWLIKKNNTYPTIKRSYNNTNQEDLLILWGIH
HSNDAAEQTKLYQNPTTYISVGTSTLNQRLVPKIATRSKVNGQNGRMDFFWTILKPNDAINFES
NGNFIAPEYAYKIVKKGDSAIVKSEVEYGNCNTKCQTPIGAINSSMPFHNIHPLTIGECPKYVKSN
KLVLATGLRNSPLRERRRKRGLFGAIAGFIEGGWQGMVDGWYGYHHSNEQGSGYAADKEST
QKAIDGVTNKVNSIIDKMNTQFEAVGREFNNLERRIENLNKKMEDGFLDVWTYNAELLVLMENE
RTLDFHDSNVKNLYDKVRLQLRDNAKELGNGCFEFYHKCDNECMESVRNGTYDYPQYSEEAR
LKREEISGVKLESIGTYQILSIYSTVASSLALAIMVAGLSLWMCSNGSLQCRICIGYIPEAPRDGQ
AYVRKDGEWVLLSTFL SEQ ID NO. 9
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSGV
SSACPYQGTPSFFRNVVWLIKKNNTYPTIKRSYNNTNQEDLLILWGIHHSNDAAEQTKLYQNPT
TYISVGTSTLNQRLVPKIATRSKVNGQNGRMDFFWTILKPNDAINFESNGNFIAPEYAYKIVKKG
DSAIVKSEVEYGNCNTKCQTPIGAINSSMPFHNIHPLTIGECPKYVKSNKLVLATGLRNSPL-GYI
PEAPRDGQAYVRKDGEWVLLSTFL SEQ ID NO. 10
GLFGAIAGFIEGGWQGMVDGWYGYHHSNEQGSGYAADKESTQKAIDGVTNKVNSIIDKMNTQ
FEAVGREFNNLERRIENLNKKMEDGFLDVWTYNAELLVLMENERTLDFHDSNVKNLYDKVRLQ
LRDNAKELGNGCFEFYHKCDNECMESVRNGTYDYPQYSEEARLKREEISGVKLESIGTYQILSI
YSTVASSLALAIMVAGLSLWMCSNGSLQCRICI-GYIPEAPRDGQAYVRKDGEWVLLSTFL SEQ ID NO. 11
LSRINHFEKIQIIPKSSWSDHEASSGVSSACPYQGTPSFFRNVVWLIKKNNTYPTIKRSYNNTNQ
EDLLILWGIHHSNDAAEQTKLYQNPTTYISVGTSTLNQRLVPKIATRSKVNGQNGRMDFFWTILK
PNDAINFESNGNFIAPEYAYKIVKK-GYIPEAPRDGQAYVRKDGEWVLLSTFL TABLE 2-continued Amino acid and DNA sequences of immunopotentiator-linked oligomeric influenza immunogenic compositions (Note: SEQ ID NO. 40 and 42-48 are DNA sequences, while others are amino acid sequences)

SEQ ID NO. 12 [HA-hFc]:
MEKIVLLLAIVSLVKSDQICIGYHANNSTEQVDTIMEKNVTVTHAQDILEKTHNGKLCDLDGVKPL
ILRDCSVAGWLLGNPMCDEFINVPEWSYIVEKANPANDLCYPGNFNDYEELKHLLSRINHFEKI
QIIPKSSWSDHEASSGVSSACPYQGTPSFFRNVVWLIKKNNTYPTIKRSYNNTNQEDLLILWGIH
HSNDAAEQTKLYQNPTTYISVGTSTLNQRLVPKIATRSKVNGQNGRMDFFWTILKPNDAINFES
NGNFIAPEYAYKIVKKGDSAIVKSEVEYGNCNTKCQTPIGAINSSMPFHNIHPLTIGECPKYVKSN
KLVLATGLRNSPLRERRRKRGLFGAIAGFIEGGWQGMVDGWYGYHHSNEQGSGYAADKEST
QKAIDGVTNKVNSIIDKMNTQFEAVGREFNNLERRIENLNKKMEDGFLDVWTYNAELLVLMENE
RTLDFHDSNVKNLYDKVRLQLRDNAKELGNGCFEFYHKCDNECMESVRNGTYDYPQYSEEAR
LKREEISGVKLESIGTYQILSIYSTVASSLALAIMVAGLSLWMCSNGSLQCRICI-RSDKTHTCPP
CPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRW
QQGNVFSCSVMHEALHNHYTQKSLSLSPGK

SEQ ID NO. 13
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSGV
SSACPYQGTPSFFRNVVWLIKKNNTYPTIKRSYNNTNQEDLLILWGIHHSNDAAEQTKLYQNPT
TYISVGTSTLNQRLVPKIATRSKVNGQNGRMDFFWTILKPNDAINFESNGNFIAPEYAYKIVKKG
DSAIVKSEVEYGNCNTKCQTPIGAINSSMPFHNIHPLTIGECPKYVKSNKLVLATGLRNSPL-RS
DKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

SEQ ID NO. 14
GLFGAIAGFIEGGWQGMVDGWYGYHHSNEQGSGYAADKESTQKAIDGVTNKVNSIIDKMNTQ
FEAVGREFNNLERRIENLNKKMEDGFLDVWTYNAELLVLMENERTLDFHDSNVKNLYDKVRLQ
LRDNAKELGNGCFEFYHKCDNECMESVRNGTYDYPQYSEEARLKREEISGVKLESIGTYQILSI
YSTVASSLALAIMVAGLSLVVMCSNGSLQCRICI-RSDKTHTCPPCPAPELLGGPSVFLFPPKPK
DTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKNQVSLTCLVKGFYP
SDIAVEWESNGQPENNYKTTPPVLDSDGSFFLYSKLTVDKSRWQQGNVFSCSVMHEALHNHY
TQKSLSLSPGK

SEQ ID NO. 15
LSRINHFEKIQIIPKSSWSDHEASSGVSSACPYQGTPSFFRNVVWLIKKNNTYPTIKRSYNNTNQ
EDLLILWGIHHSNDAAEQTKLYQNPTTYISVGTSTLNQRLVPKIATRSKVNGQNGRMDFFWTILK
PNDAINFESNGNFIAPEYAYKIVKK-RSDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSLSLSP
GK

SEQ ID NO. 16
MEKIVLLLAIVSLVKSDQICIGYHANNSTEQVDTIMEKNVTVTHAQDILEKTHNGKLCDLDGVKPL
ILRDCSVAGWLLGNPMCDEFINVPEWSYIVEKANPANDLCYPGNFNDYEELKHLLSRINHFEKI
QIIPKSSWSDHEASSGVSSACPYQGTPSFFRNVVWLIKKNNTYPTIKRSYNNTNQEDLLILWGIH
HSNDAAEQTKLYQNPTTYISVGTSTLNQRLVPKIATRSKVNGQNGRMDFFWTILKPNDAINFES
NGNFIAPEYAYKIVKKGDSAIVKSEVEYGNCNTKCQTPIGAINSSMPFHNIHPLTIGECPKYVKSN
KLVLATGLRNSPLRERRRKRGLFGAIAGFIEGGWQGMVDGWYGYHHSNEQGSGYAADKEST
QKAIDGVTNKVNSIIDKMNTQFEAVGREFNNLERRIENLNKKMEDGFLDVWTYNAELLVLMENE
RTLDFHDSNVKNLYDKVRLQLRDNAKELGNGCFEFYHKCDNECMESVRNGTYDYPQYSEEAR
LKREEISGVKLESIGTYQILSIYSTVASSLALAIMVAGLSLWMCSNGSLQCRICI-GYIPEAPRDGQ
AYVRKDGEWVLLSTFL-RSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK

SEQ ID NO. 17 [HA1-Fd-hFc]:
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSGV
SSACPYQGTPSFFRNVVWLIKKNNTYPTIKRSYNNTNQEDLLILWGIHHSNDAAEQTKLYQNPT
TYISVGTSTLNQRLVPKIATRSKVNGQNGRMDFFWTILKPNDAINFESNGNFIAPEYAYKIVKKG
DSAIVKSEVEYGNCNTKCQTPIGAINSSMPFHNIHPLTIGECPKYVKSNKLVLATGLRNSPL-GYI
PEAPRDGQAYVRKDGEWVLLSTFL-RSDKTHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLSLS
PGK

SEQ ID NO. 18 [HA2-Fd-hFc]:
GLFGAIAGFIEGGWQGMVDGWYGYHHSNEQGSGYAADKESTQKAIDGVTNKVNSIIDKMNTQ
FEAVGREFNNLERRIENLNKKMEDGFLDVWTYNAELLVLMENERTLDFHDSNVKNLYDKVRLQ
LRDNAKELGNGCFEFYHKCDNECMESVRNGTYDYPQYSEEARLKREEISGVKLESIGTYQILSI

TABLE 2-continued

Amino acid and DNA sequences of immunopotentiator-linked oligomeric influenza immunogenic compositions (Note: SEQ ID NO. 40 and 42-48 are DNA sequences, while others are amino acid sequences)

YSTVASSLALAIMVAGLSLWMCSNGSLQCRICI-GYIPEAPRDGQAYVRKDGEWVLLSTFL-RS
DKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

SEQ ID NO. 19
LSRINHFEKIQIIPKSSWSDHEASSGVSSACPYQGTPSFFRNVVWLIKKNNTYPTIKRSYNNTNQ
EDLLILWGIHHSNDAAEQTKLYQNPTTYISVGTSTLNQRLVPKIATRSKVNGQNGRMDFFWTILK
PNDAINFESNGNFIAPEYAYKIVKK-GYIPEAPRDGQAYVRKDGEWVLLSTFL-RSDKTHTCPP
CPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVDKSRW
QQGNVFSCSVMHEALHNHYTQKSLSLSPGK

SEQ ID NO. 20 [mouse IoG Fc (mFc)]:
RSPRGPTIKPCPPCKCPAPNLLGGPSVFIFPPKIKDVLMISLSPIVTCVVVDVSEDDPDVQISWFV
NNVEVHTAQTQTHREDYNSTLRVVSALPIQHQDWMSGKEFKCKVNNKDLPAPIERTISKPKGS
VRAPQVYVLPPPEEEMTKKQVTLTCMVTDFMPEDIYVEWTNNGKTELNYKNTEPVLDSDGSYF
MYSKLRVEKKNWVERNSYSCSVVHEGLHNHHTTKSFSRTPGK SEQ ID NO. 21
MEKIVLLLAIVSLVKSDQICIGYHANNSTEQVDTIMEKNVTVTHAQDILEKTHNGKLCDLDGVKPL
ILRDCSVAGWLLGNPMCDEFINVPEWSYIVEKANPANDLCYPGNFNDYEELKHLLSRINHFEKI
QIIPKSSWSDHEASSGVSSACPYQGTPSFFRNVVWLIKKNNTYPTIKRSYNNTNQEDLLILWGIH
HSNDAAEQTKLYQNPTTYISVGTSTLNQRLVPKIATRSKVNGQNGRMDFFWTILKPNDAINFES
NGNFIAPEYAYKIVKKGDSAIVKSEVEYGNCNTKCQTPIGAINSSMPFHNIHPLTIGECPKYVKSN
KLVLATGLRNSPLRERRRKRGLFGAIAGFIEGGWQGMVDGWYGYHHSNEQGSGYAADKEST
QKAIDGVTNKVNSIIDKMNTQFEAVGREFNNLERRIENLNKKMEDGFLDVWTYNAELLVLMENE
RTLDFHDSNVKNLYDKVRLQLRDNAKELGNGCFEFYHKCDNECMESVRNGTYDYPQYSEEAR
LKREEISGVKLESIGTYQILSIYSTVASSLALAIMVAGLSLWMCSNGSLQCRICI-GYIPEAPRDGQ
AYVRKDGEWVLLSTFL-RSPRGPTIKPCPPCKCPAPNLLGGPSVFIFPPKIKDVLMISLSPIVTCV
VVDVSEDDPDVQISWFVNNVEVHTAQTQTHREDYNSTLRVVSALPIQHQDWMSGKEFKCKVN
NKDLPAPIERTISKPKGSVRAPQVYVLPPPEEEMTKKQVTLTCMVTDFMPEDIYVEWTNNGKTE
LNYKNTEPVLDSDGSYFMYSKLRVEKKNWVERNSYSCSVVHEGLHNHHTTKSFSRTPGK SEQ ID NO. 22
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSGV
SSACPYQGTPSFFRNVVWLIKKNNTYPTIKRSYNNTNQEDLLILWGIHHSNDAAEQTKLYQNPT
TYISVGTSTLNQRLVPKIATRSKVNGQNGRMDFFWTILKPNDAINFESNGNFIAPEYAYKIVKKG
DSAIVKSEVEYGNCNTKCQTPIGAINSSMPFHNIHPLTIGECPKYVKSNKLVLATGLRNSPL-GYI
PEAPRDGQAYVRKDGEWVLLSTFL-RSPRGPTIKPCPPCKCPAPNLLGGPSVFIFPPKIKDVLMI
SLSPIVTCVVVDVSEDDPDVQISWFVNNVEVHTAQTQTHREDYNSTLRVVSALPIQHQDWMSG
KEFKCKVNNKDLPAPIERTISKPKGSVRAPQVYVLPPPEEEMTKKQVTLTCMVTDFMPEDIYVE
WTNNGKTELNYKNTEPVLDSDGSYFMYSKLRVEKKNWVERNSYSCSVVHEGLHNHHTTKSFS
RTPGK SEQ ID NO. 23
GLFGAIAGFIEGGWQGMVDGWYGYHHSNEQGSGYAADKESTQKAIDGVTNKVNSIIDKMNTQ
FEAVGREFNNLERRIENLNKKMEDGFLDVWTYNAELLVLMENERTLDFHDSNVKNLYDKVRLQ
LRDNAKELGNGCFEFYHKCDNECMESVRNGTYDYPQYSEEARLKREEISGVKLESIGTYQILSI
YSTVASSLALAIMVAGLSLWMCSNGSLQCRICI-GYIPEAPRDGQAYVRKDGEWVLLSTFL-RS
PRGPTIKPCPPCKCPAPNLLGGPSVFIFPPKIKDVLMISLSPIVTCVVVDVSEDDPDVQISWFVN
NVEVHTAQTQTHREDYNSTLRVVSALPIQHQDWMSGKEFKCKVNNKDLPAPIERTISKPKGSV
RAPQVYVLPPPEEEMTKKQVTLTCMVTDFMPEDIYVEWTNNGKTELNYKNTEPVLDSDGSYF
MYSKLRVEKKNWVERNSYSCSVVHEGLHNHHTTKSFSRTPGK SEQ ID NO. 24
LSRINHFEKIQIIPKSSWSDHEASSGVSSACPYQGTPSFFRNVVWLIKKNNTYPTIKRSYNNTNQ
EDLLILWGIHHSNDAAEQTKLYQNPTTYISVGTSTLNQRLVPKIATRSKVNGQNGRMDFFWTILK
PNDAINFESNGNFIAPEYAYKIVKK-GYIPEAPRDGQAYVRKDGEWVLLSTFL-RSPRGPTIKPC
PPCKCPAPNLLGGPSVFIFPPKIKDVLMISLSPIVTCVVVDVSEDDPDVQISWFVNNVEVHTAQT
QTHREDYNSTLRVVSALPIQHQDWMSGKEFKCKVNNKDLPAPIERTISKPKGSVRAPQVYVLP
PPEEEMTKKQVTLTCMVTDFMPEDIYVEWTNNGKTELNYKNTEPVLDSDGSYFMYSKLRVEKK
NWVERNSYSCSVVHEGLHNHHTTKSFSRTPGK SEQ ID NO. 25 [rabbit IgG Fc (rFc)]:
RSSKPTCPPPELLGGPSVFIFPPKPKDTLMISRTPEVTCVVVDVSQDDPEVQFTWYINNEQVRT
ARPPLREQQFNSTIRVVSTLPIAHQDWLRGKEFKCKVHNKALPAPIEKTISKARGQPLEPKVYT
MGPPREELSSRSVSLTCMINGFYPSDISVEWEKNGKAEDNYKTTPAVLDSDGSYFLYSKLSVP
TSEWQRGDVFTCSVMHEALHNHYTQKSISRSPGK SEQ ID NO. 26
MEKIVLLLAIVSLVKSDQICIGYHANNSTEQVDTIMEKNVTVTHAQDILEKTHNGKLCDLDGVKPL
ILRDCSVAGWLLGNPMCDEFINVPEWSYIVEKANPANDLCYPGNFNDYEELKHLLSRINHFEKI TABLE 2-continued Amino acid and DNA sequences of immunopotentiator-linked oligomeric influenza immunogenic compositions (Note: SEQ ID NO. 40 and 42-48 are DNA sequences, while others are amino acid sequences)

QIIPKSSWSDHEASSGVSSACPYQGTPSFFRNVVWLIKKNNTYPTIKRSYNNTNQEDLLILWGIH
HSNDAAEQTKLYQNPTTYISVGTSTLNQRLVPKIATRSKVNGQNGRMDFFWTILKPNDAINFES
NGNFIAPEYAYKIVKKGDSAIVKSEVEYGNCNTKCQTPIGAINSSMPFHNIHPLTIGECPKYVKSN
KLVLATGLRNSPLRERRRKRGLFGAIAGFIEGGWQGMVDGWYGYHHSNEQGSGYAADKEST
QKAIDGVTNKVNSIIDKMNTQFEAVGREFNNLERRIENLNKKMEDGFLDVWTYNAELLVLMENE
RTLDFHDSNVKNLYDKVRLQLRDNAKELGNGCFEFYHKCDNECMESVRNGTYDYPQYSEEAR
LKREEISGVKLESIGTYQILSIYSTVASSLALAIMVAGLSLWMCSNGSLQCRICI-GYIPEAPRDGQ
AYVRKDGEWVLLSTFL-RSSKPTCPPPELLGGPSVFIFPPKPKDTLMISRTPEVTCVVVDVSQD
DPEVQFTWYINNEQVRTARPPLREQQFNSTIRVVSTLPIAHQDWLRGKEFKCKVHNKALPAPIE
KTISKARGQPLEPKVYTMGPPREELSSRSVSLTCMINGFYPSDISVEWEKNGKAEDNYKTTPAV
LDSDGSYFLYSKLSVPTSEWQRGDVFTCSVMHEALHNHYTQKSISRSPGK

SEQ ID NO. 27
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSGV
SSACPYQGTPSFFRNVVWLIKKNNTYPTIKRSYNNTNQEDLLILWGIHHSNDAAEQTKLYQNPT
TYISVGTSTLNQRLVPKIATRSKVNGQNGRMDFFWTILKPNDAINFESNGNFIAPEYAYKIVKKG
DSAIVKSEVEYGNCNTKCQTPIGAINSSMPFHNIHPLTIGECPKYVKSNKLVLATGLRNSPL-GYI
PEAPRDGQAYVRKDGEWVLLSTFL-RSSKPTCPPPELLGGPSVFIFPPKPKDTLMISRTPEVTC
VVVDVSQDDPEVQFTWYINNEQVRTARPPLREQQFNSTIRVVSTLPIAHQDWLRGKEFKCKVH
NKALPAPIEKTISKARGQPLEPKVYTMGPPREELSSRSVSLTCMINGFYPSDISVEWEKNGKAE
DNYKTTPAVLDSDGSYFLYSKLSVPTSEWQRGDVFTCSVMHEALHNHYTQKSISRSPGK

SEQ ID NO. 28
GLFGAIAGFIEGGWQGMVDGWYGYHHSNEQGSGYAADKESTQKAIDGVTNKVNSIIDKMNTQ
FEAVGREFNNLERRIENLNKKMEDGFLDWVTYNAELLVLMENERTLDFHDSNVKNLYDKVRLQ
LRDNAKELGNGCFEFYHKCDNECMESVRNGTYDYPQYSEEARLKREEISGVKLESIGTYQILSI
YSTVASSLALAIMVAGLSLWMCSNGSLQCRICI-GYIPEAPRDGQAYVRKDGEWVLLSTFL-RS
SKPTCPPPELLGGPSVFIFPPKPKDTLMISRTPEVTCVVVDVSQDDPEVQFTWYINNEQVRTAR
PPLREQQFNSTIRVVSTLPIAHQDWLRGKEFKCKVHNKALPAPIEKTISKARGQPLEPKVYTMG
PPREELSSRSVSLTCMINGFYPSDISVEWEKNGKAEDNYKTTPAVLDSDGSYFLYSKLSVPTSE
WQRGDVFTCSVMHEALHNHYTQKSISRSPGK

SEQ ID NO. 29
LSRINHFEKIQIIPKSSWSDHEASSGVSSACPYQGTPSFFRNVVWLIKKNNTYPTIKRSYNNTNQ
EDLLILWGIHHSNDAAEQTKLYQNPTTYISVGTSTLNQRLVPKIATRSKVNGQNGRMDFFWTILK
PNDAINFESNGNFIAPEYAYKIVKK-GYIPEAPRDGQAYVRKDGEWVLLSTFL-RSSKPTCPPPE
LLGGPSVFIFPPKPKDTLMISRTPEVTCVVVDVSQDDPEVQFTWYINNEQVRTARPPLREQQFN
STIRVVSTLPIAHQDWLRGKEFKCKVHNKALPAPIEKTISKARGQPLEPKVYTMGPPREELSSRS
VSLTCMINGFYPSDISVEWEKNGKAEDNYKTTPAVLDSDGSYFLYSKLSVPTSEWQRGDVFTC
SVMHEALHNHYTQKSISRSPGK

SEQ ID NO. 30 [A/Anhui/1/2005(H5N1) HA1 +3-259]:
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSGV
SSACPYQGTPSFFRNVVWLIKKNNTYPTIKRSYNNTNQEDLLILWGIHHSNDAAEQTKLYQNPT
TYISVGTSTLNQRLVPKIATRSKVNGQNGRMDFFWTILKPNDAINFESNGNFIAPEYAYKIVKK SEQ ID NO. 31 [HA1 +3-259-Fd]:
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSGV
SSACPYQGTPSFFRNVVWLIKKNNTYPTIKRSYNNTNQEDLLILWGIHHSNDAAEQTKLYQNPT
TYISVGTSTLNQRLVPKIATRSKVNGQNGRMDFFWTILKPNDAINFESNGNFIAPEYAYKIVKK-
GYIPEAPRDGQAYVRKDGEWVLLSTFL SEQ ID NO. 32 [HA1 +3-259-hFc]:
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSGV
SSACPYQGTPSFFRNVVWLIKKNNTYPTIKRSYNNTNQEDLLILWGIHHSNDAAEQTKLYQNPT
TYISVGTSTLNQRLVPKIATRSKVNGQNGRMDFFWTILKPNDAINFESNGNFIAPEYAYKIVKK-
RSDKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTPPVLDSDGSFFLY
SKLTVDKSRWQQGNVFSCSVMHEALHNHYTQKSLSLSPGK SEQ ID NO. 33 [HA1 +3-259-Fd-hFc]:
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSGV
SSACPYQGTPSFFRNVVWLIKKNNTYPTIKRSYNNTNQEDLLILWGIHHSNDAAEQTKLYQNPT
TYISVGTSTLNQRLVPKIATRSKVNGQNGRMDFFWTILKPNDAINFESNGNFIAPEYAYKIVKK-
GYIPEAPRDGQAYVRKDGEWVLLSTFL-RSDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSL
SLSPGK TABLE 2-continued Amino acid and DNA sequences of immunopotentiator-linked oligomeric
influenza immunogenic compositions (Note: SEQ ID NO. 40 and 42-48
are DNA sequences, while others are amino acid sequences)

SEQ ID NO. 34 [HA1 +3-259-Fd-mFc]:
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSGV
SSACPYQGTPSFFRNVVWLIKKNNTYPTIKRSYNNTNQEDLLILWGIHHSNDAAEQTKLYQNPT
TYISVGTSTLNQRLVPKIATRSKVNGQNGRMDFFWTILKPNDAINFESNGNFIAPEYAYKIVKK-
GYIPEAPRDGQAYVRKDGEWVLLSTFL-RSPRGPTIKPCPPCKCPAPNLLGGPSVFIFPPKIKDV
LMISLSPIVTCVVVDVSEDDPDVQISWFVNNVEVHTAQTQTHREDYNSTLRVVSALPIQHQDW
MSGKEFKCKVNNKDLPAPIERTISKPKGSVRAPQVYVLPPPEEEMTKKQVTLTCMVTDFMPEDI
YVEWTNNGKTELNYKNTEPVLDSDGSYFMYSKLRVEKKNWVERNSYSCSVVHEGLHNHHTTK
SFSRTPGK

SEQ ID NO. 35 [HA1 +3-259-Fd-rFc]:
ICIGYHANNSTEQVDTIMEKNVTVTHAQDILEKTHNGKLCDLDGVKPLILRDCSVAGWLLGNPM
CDEFINVPEWSYIVEKANPANDLCYPGNFNDYEELKHLLSRINHFEKIQIIPKSSWSDHEASSGV
SSACPYQGTPSFFRNVVWLIKKNNTYPTIKRSYNNTNQEDLLILWGIHHSNDAAEQTKLYQNPT
TYISVGTSTLNQRLVPKIATRSKVNGQNGRMDFFWTILKPNDAINFESNGNFIAPEYAYKIVKK-
GYIPEAPRDGQAYVRKDGEWVLLSTFL-RSSKPTCPPPELLGGPSVFIFPPKPKDTLMISRTPE
VTCVVVDVSQDDPEVQFTWYINNEQVRTARPPLREQQFNSTIRVVSTLPIAHQDWLRGKEFKC
KVHNKALPAPIEKTISKARGQPLEPKVYTMGPPREELSSRSVSLTCMINGFYPSDISVEWEKNG
KAEDNYKTTPAVLDSDGSYFLYSKLSVPTSEWQRGDVFTCSVMHEALHNHYTQKSISRSPGK

In one embodiment, the stabilization sequence comprises a sequence that stabilizes the HA sequence in the trimer or oligomer configuration. As used herein, the terms stabilization sequence, trimeric motif and trimerization sequence are interchangeable and equivalent. Suitable stabilization sequences include, but are not limited to, foldon a 27 amino acid region of the C-terminal domain of T4 fibritin (GYIPEAPRDGQAYVRKDGEWVLLSTFL, SEQ ID NO:6 or GSGYIPEAPRDGQAYVRKDGEWVLLSTFL, SEQ ID NO:36), GCN4 (MKQIEDKIEEILSKIYHIENEIARIKKLIGEV; SEQ ID NO. 37), IQ (RMKQIEDKIEEIESKQKKIENEIARIKK; SEQ ID NO. 38) or IZ (IKKEIEAIKKEQEAIKKKIEAIEK; SEQ ID NO. 39). Other suitable stabilization methods include, but are not limited to, 2,2-bipyridine-5-carboxylic acid (BPY), disulfide bonds and facile ligation.

In another embodiment, the immunopotentiator comprises a sequence to enhance the immunogenicity of the immunogenic composition. Suitable immunopotentiators include, but are not limited to, the Fc fragment of human IgG, C3d (a complement fragment that promotes antibody formation binding to antigens enhancing their uptake by dendritic cells and B cells), ASP-1 (*Onchocerca volvulus* homologue of the activation associated secreted gene family) (see US 20060039921, which is incorporated by reference herein for all it discloses regarding ASP-1 adjuvants), cholera toxin, muramyl peptides and cytokines.

In one embodiment, the claimed fusion proteins can be constructed using overlapping primers. In another embodiment, the DNA sequence (GGCTATATTCCGGAAGCGCCGCGTGATGGCCAGGCGTATGTGCGTAAAGATGGCGAATGGGTGCTGCTGTCTACCTTTCTG; SEQ ID NO:40) encoding Fd is synthesized first. Separate PCR products of HA1 and HA-3-259 and Fd are generated and the HA1-Fd and HA-3-259-Fd fusion fragment is amplified by one-round PCR using an HA1 or HA-3-259 Forward primer and Fd Reverse primer with HA1 and Fd DNA (PCR products) as templates. The amplified HA1-Fd and HA-3-259-Fd PCR products are then inserted into the hFc vector, to produce HA1-Fd-hFc and HA-3-259-Fd-hFc recombinant plasmids encoding HA1-Fd-hFc and HA-3-259-Fd-hFc fusion proteins, respectively.

In one embodiment, pFUSE-hIgG1-Fc (human Fc, hFc), pFUSE-mIgG2a-Fc2 (murine Fc, mFc), or pFUSE-rIgG2-Fc2 (rabbit Fc, rFc) vectors are used for construction of the disclosed fusion proteins. In another embodiment, the fusion proteins can be expressed from other mammalian cell expression vectors, including, but not limited to, pcDNA3.1, pcDNA6-His, PEE13.1, PEE1.41, pCMV-NEO-BAM, pSV2, and pCMV1, 2, 3, 4, 5, 6. In another embodiment, the fusion proteins can be expressed from insect cell expression vectors including, but not limited to, pAcGP67, pFastBac Dual, and pMT/V5-His-TOPO. In yet another embodiment, the fusion proteins can be expressed from *E. coli* expression vectors including, but not limited to, pET, pET-SUMO, and pGEX vectors with GST.

The following expression systems are suitable for use in expressing the disclosed fusion proteins: mammalian cell expression systems such as, but not limited to, the pcDNA and GS Gene expression systems; insect cell expression systems such as, but not limited to, Bac-to-Bac, baculovirus and DES expression systems; and *E. coli* expression systems including, but not limited to, pET, pSUMO and GST expression systems.

Advantages of proteins expressed in mammalian cell expression systems include the follows. The mammalian cell expression system is a relatively mature eukaryotic system for expression of recombinant proteins. It is more likely to achieve correctly folded soluble proteins with proper glycosylation, making the expressed protein maintain its native conformation and keep sufficient bioactivity. This system can either transiently or stably express recombinant antigens, and promote signal synthesis. Recombinant proteins expressed in this way may keep good antigenicity and immunogenicity. However, both insect and bacterial expression systems provide inexpensive and efficient expression of proteins which may be appropriate under certain conditions.

The purification systems are dependent on whether a tag is linked or fused with the HA proteins. When the fusion proteins are fused with IgG Fc vectors, Protein A or Protein G affinity chromatography is used for the purification. If the fusion proteins are fused with GST proteins, the GST columns will be used for the purification. If the fusion proteins link with 6×His tag at the N- or C-terminal, the expressed proteins are be purified using His tag columns. If no tag is linked with recombinant proteins, the expressed proteins could be purified using Fast protein liquid chromatography (FPLC), High performance liquid chromatography (HPLC) or other chromatography.

In certain embodiments, the immunogenic compositions further comprise or are administered with an adjuvant. Adjuvants suitable for use in animals include, but are not limited to, Freund's complete or incomplete adjuvants, Sigma Adjuvant System (SAS), and Ribi adjuvants. Adjuvants suitable for use in humans include, but are not limited to, MF59 (an oil-in-water emulsion adjuvant), Montanide ISA 51 or 720 (a mineral oil-based or metabolizable oil-based adjuvant), aluminum hydroxide, -phosphate or -oxide, HAVLOGEN® (an acrylic acid polymer-based adjuvant, Intervet Inc., Millsboro, Del.), polyacrylic acids, oil-in-water or water-in-oil emulsion based on, for example a mineral oil, such as BAYOL™ or MARCOL™ (Esso Imperial Oil Limited, Canada), or a vegetable oil such as vitamin E acetate, saponins, and Onchocerca volvulus activation-associated protein-1 (ASP-1) (see US 20060039921, which is incorporated by reference herein for all it discloses regarding ASP-1 adjuvants). However, components with adjuvant activity are widely known and, generally, any adjuvant may be utilized that does not adversely interfere with the efficacy or safety of the vaccine and/or immunogenic composition.

Vaccine and immunogenic compositions according to the various embodiments disclosed herein can be prepared and/or marketed in the form of a liquid, frozen suspension or in a lyophilized form. Typically, vaccines and/or immunogenic compositions prepared according to the present disclosure contain a pharmaceutically acceptable carrier or diluent customarily used for such compositions. Carriers include, but are not limited to, stabilizers, preservatives and buffers. Suitable stabilizers are, for example SPGA, Tween compositions (such as are available from A.G. Scientific, Inc., San Diego, Calif.), carbohydrates (such as sorbitol, mannitol, starch, sucrose, dextran, glutamate or glucose), proteins (such as dried milk serum, albumin or casein) or degradation products thereof. Non-limiting examples of suitable buffers include alkali metal phosphates. Suitable preservatives are thimerosal, merthiolate and gentamicin. Diluents include water, aqueous buffer (such as buffered saline), alcohols and polyols (such as glycerol).

Also disclosed herein are methods for inducing an immune response to an influenza virus using the disclosed fusion proteins. Generally, the vaccine or immunogenic composition may be administered subcutaneously, intradermally, submucosally, or intramuscularly in an effective amount to prevent infection from the influenza virus of interest and/or treat an infection from the influenza virus. An effective amount is defined as an amount of immunizing fusion protein that will induce immunity in the vaccinated animals, against challenge by a virulent virus. Immunity is defined herein as the induction of a significant higher level of protection in a population of the animal after vaccination compared to an unvaccinated group.

Further, in various formulations of the vaccines and/or immunogenic compositions, suitable excipients, stabilizers and the like may be added.

EXAMPLES

Example 1

Construction and Expression of Recombinant HA Proteins of H5N1 Virus

Construction of recombinant plasmids encoding HA1-hFc, HA1-Fd-hFc and HA-3-259-Fd-hFc. The genes encoding the fragment containing 320 amino acid (aa) (+3-322) of the HA1 fragment (SEQ ID NO. 2) of the H5N1 HA protein were amplified by PCR with a plasmid containing codon-optimized full-length HA (SEQ ID NO. 1) of influenza A H5N1 virus [A/Anhui/1/2005(H5N1), GenBank accession number ABD28180.1)] as the template, and fused in frame into the pFUSE-hIgG1-Fc2 (human IgG Fc, hFc) expression vector (InvivoGen, San Diego, Calif.). The constructed recombinant plasmid was thus named pHA1-hFc. The Fd sequence were added at the 3' end by PCR using overlapping primers covering Fd, followed by insertion into the above hFc expression vector, which was named pHA1-Fd-hFc. The plasmid coding HA-3-259-Fd-hFc (SEQ ID NO:33) was constructed by insertion of genes encoding the fragment containing residues +3-259 of the above HA1 fragment (SEQ ID NO. 2) of H5N1 HA protein plus the above Fd sequence into the above hFc expression vector. The constructed recombinant plasmids were confirmed by sequencing analysis. The aa sequences of the H5N1 HA proteins, Fd and hFc fragments are listed in the Table 1.

The HA protein of A/Anhui/1/2005(H5N1) virus contains fragments of the signal peptide (SP), HA1 (+1-329 aa) and HA2 (+330-551 aa) spanned by a specific sequence of protease cleavage site RERRRKR (SEQ ID NO:41) between HA1 and HA2. In the construction of the recombinant HA1-hFc plasmid, the original signal peptide of the HA protein of H5N1 virus was replaced by the IL2ss signal sequence (SEQ ID NO:5), which was followed by HA1 fragment of H5N1 (+3-322 aa) fused into the above hFc vector. The Fd sequence was inserted between HA1 and hFc, becoming HA1-Fd-hFc (SEQ ID NO:17). HA-3-259-Fd-hFc contains +3-259 aa of the above HA1 fragment of H5N1 plus the Fd sequence, fusing into the above hFc vector.

Expression, purification and characterization of recombinant HA1-hFc, HA1-Fd-hFc and HA-3-259-Fd-hFc proteins. The recombinant HA1-hFc, HA1-Fd-hFc and HA-3-259-Fd-hFc proteins were expressed as previously described (Du L et al. Biochem Biophys Res Commun 384, 486-490, 2009). In brief, recombinant plasmids encoding HA1-hFc, HA1-Fd-hFc and HA-3-259-Fd-hFc proteins were transfected into mammalian 293T cells (ATCC, Manassas, Va.) seeded 24 hr prior to transfection using the calcium phosphate method. Culture medium was replaced by fresh OPTI-MEM I Reduced-Serum Medium (Invitrogen, Carlsbad, Calif.) 10 hr later, and supernatant was collected 72 hr post-translation. The recombinant HA1-hFc, HA1-Fd-hFc and HA-3-259-Fd-hFc proteins in the supernatant were purified by Protein A affinity chromatography (GE Healthcare, Piscataway, N.J.). Conformational and characteristic analyses of HA1-hFc, HA1-Fd-hFc and HA-3-259-Fd-hFc proteins were performed by FPLC using AKTApurifier Core Systems and Unicon 5.11 software according to manufacturer's protocols (GE Healthcare Life Sciences).

Detection of protein expression by SDS-PAGE and Western blot. The purified proteins were analyzed by SDS-PAGE and Western blot as our previously described protocols (Du L et al. Virology. 393, 144-150, 2009) using HA-specific monoclonal antibodies (mAbs). In brief, 10 µg of purified proteins was separated by 10-20% Tricine SDS-PAGE gels (Invitrogen) and transferred to nitrocellulose membranes (Bio-Rad Laboratories, Hercules, Calif.). After blocking overnight at 4° C., the blots were incubated with a HA-specific mAb at 1:1,000 dilution for 1 hr at room temperature. After three washes with PBS containing 0.1% Tween-20 (PBST), the blots were then incubated with horseradish peroxidase (HRP)-conjugated goat anti-mouse IgG (1:5,000, Zymed, Carlsbad, Calif.) for 1 hr at room temperature.

Signals were visualized with ECL Western blot substrate reagents and Amersham Hyperfilm (GE Healthcare).

Figure 2:
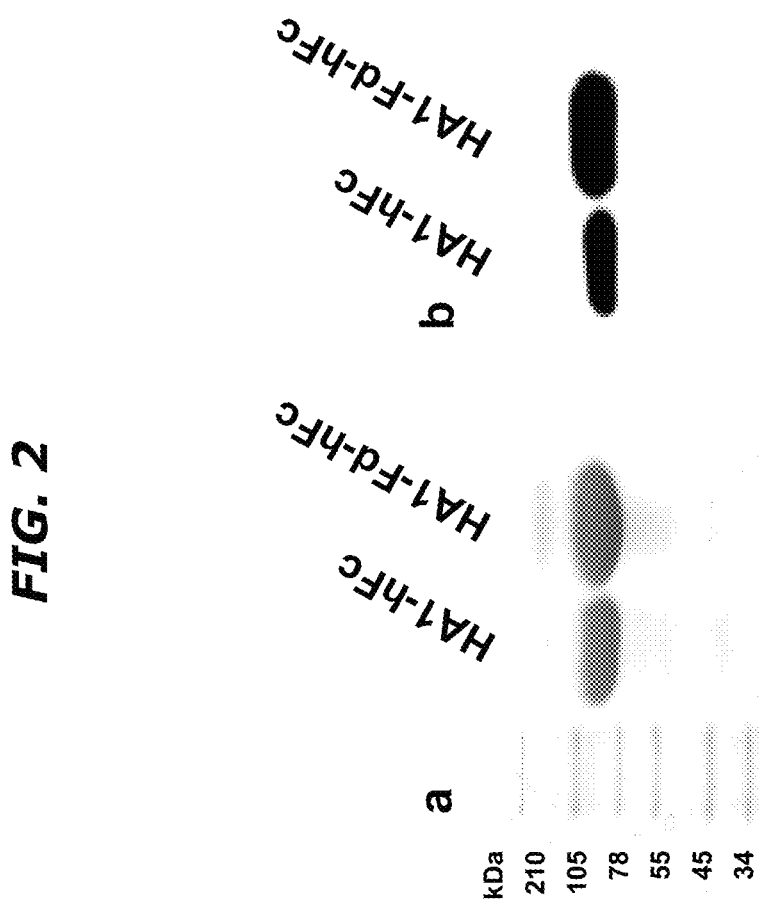
FIG. 2 depicts the sodium dodecyl sulfate polyacrylamide gel electrophoresis (SDS-PAGE) (FIG. 2a) and Western blot (FIG. 2b) analyses of the expressed HA1-hFc and HA1-Fd-hFc proteins.
Figure 3:
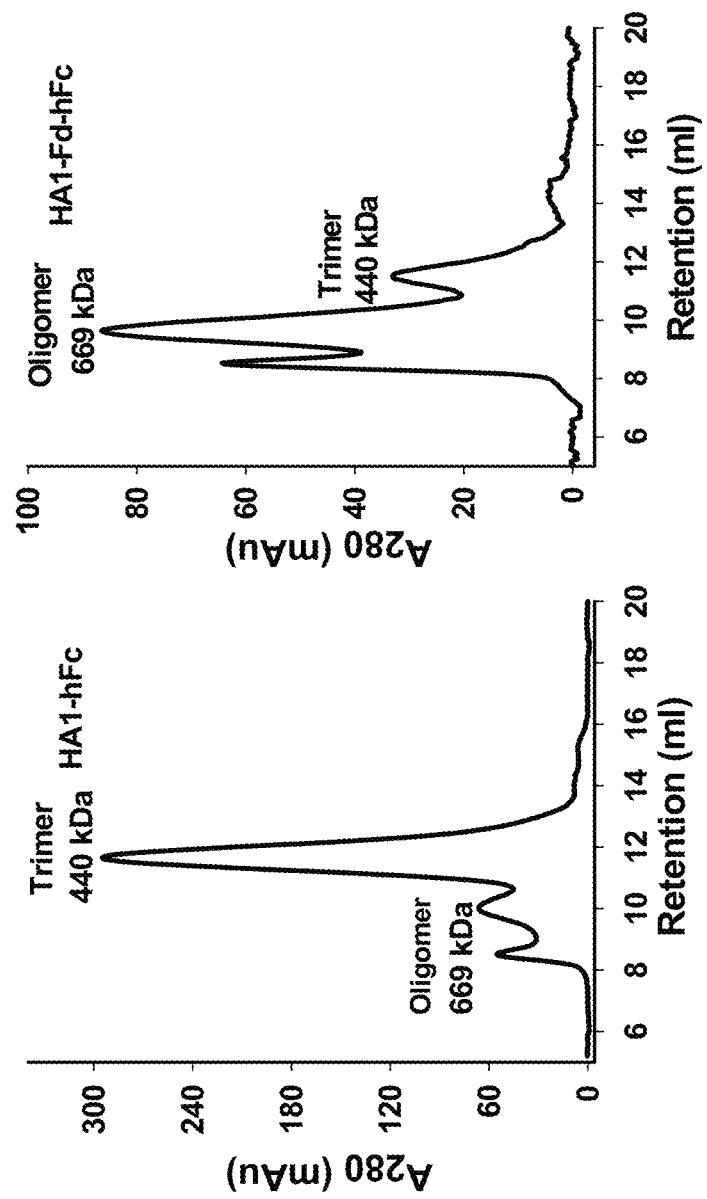
FIG. 3 depicts Fast Protein Liquid Chromatography (FPLC) analysis of the expressed HA1-hFc and HA1-Fd-hFc proteins. The molecular weight of the proteins was indicated on each peak, with the structure corresponding to calculated standard proteins.

As shown in FIG. 2, the recombinant HA1-hFc and HA1-Fd-hFc proteins could be expressed at a very high level in the secreted form in the culture supernatant of transfected 293T cells and were purified with high purity (FIG. 2a). They were recognized by the conformation-specific mAb against HA protein of H5N1 viruses as detected by Western blot (FIG. 2b), indicating that these proteins are specific to HA of influenza A H5N1 virus, suggesting that these fusion proteins maintained proper conformation and antigenicity of H5N1 viral protein HA. Further characterization of these proteins by FPLC analysis demonstrated that the majority of HA1 protein fused with Fc (HA1-hFc) mainly formed a trimer with a molecule size of ~440 kDa, while HA1 protein fused with Fd and Fc (HA1-Fd-hFc) mainly constituted an oligomeric structure with higher molecular weight at ~669 kDa (FIG. 3).

Example 2

Detection of Humoral Immune Responses Induced by Recombinant HA Fusion Proteins

Figure 4:
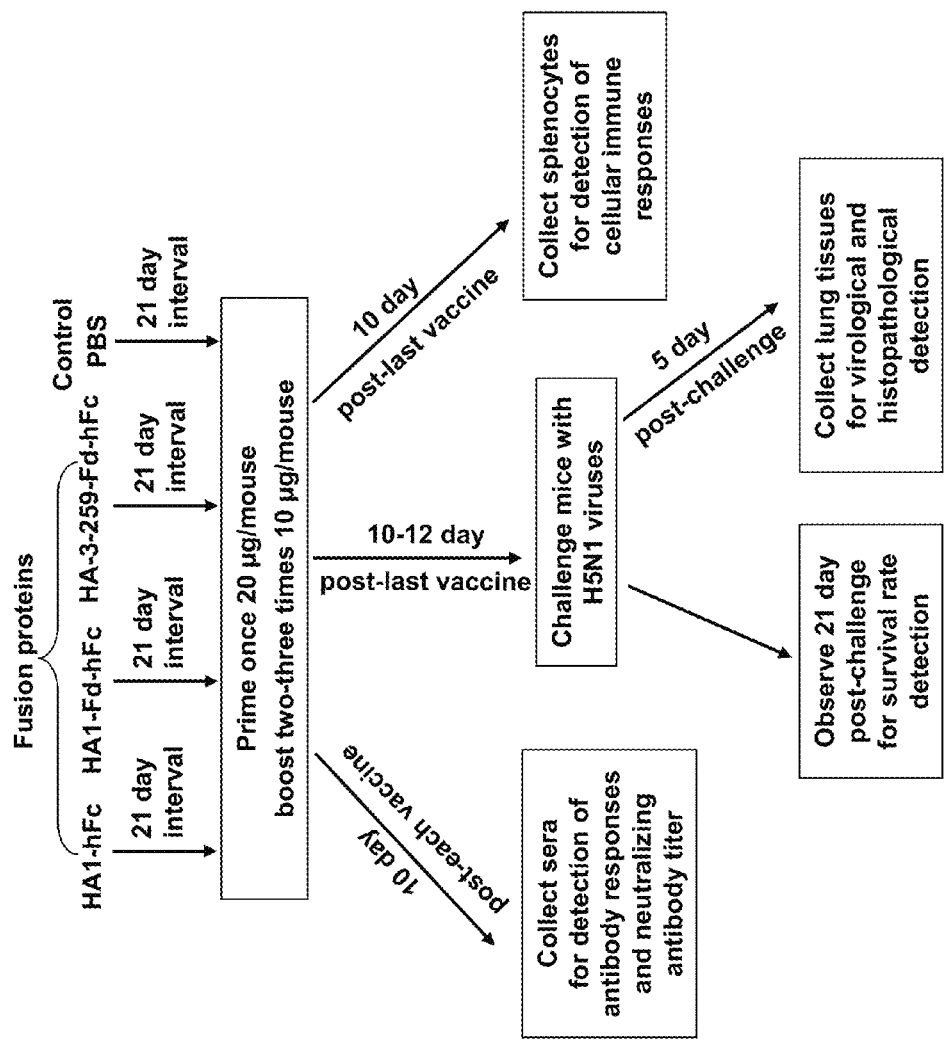
FIG. 4 depicts the immunization scheme of BALB/c mice with recombinant HA1-hFc, HA1-Fd-hFc and HA-3-259-Fd-hFc proteins, detection of induced antibodies and neutralizing activity, and challenge of the vaccinated mice with live H5N1 virus for cross-protection evaluation.

Groups of female BALB/c mice, age 4-6 weeks, were vaccinated subcutaneously (s.c.) with 20 μg/mouse of purified HA fusion proteins re-suspended in PBS in the presence of Sigma Adjuvant System (SAS, Sigma) and boosted three times with 10 μg/mouse of immunogen containing SAS at approximate 3-week intervals. PBS plus SAS was used as the negative control. Serum samples were collected before immunization and 10 days post-each vaccination to detect the generation of HA- and/or H5N1 virus-specific IgG antibodies and subtypes using ELISA. The immunization scheme is described in Table 2 and FIG. 4.

Enzyme-linked immunosorbent assays (ELISA) was used to evaluate IgG antibody responses and subtypes induced by HA proteins as previously described (Du L et al. Vaccine 25, 2832-2838, 2007; Du L et al. Virology 393:144-150, 2009). Briefly, 96-well microtiter plates were pre-coated respectively with the recombinant HA1-hFc, HA1-Fd-hFc and HA-3-259-Fd-hFc proteins, HA1 protein without Fd and hFc, and/or inactivated H5N1 virus A/VietNam/1194/2004 (VN/1194) overnight at 4° C. and blocked with 2% non-fat milk at 37° C. for 2 hr. Serially diluted mouse sera were added to the plates and incubated at 37° C. for 1 hr, followed by four washes with PBST. Bound antibodies were then reacted with HRP-conjugated goat anti-mouse IgG (Zymed), IgG1 (Invitrogen), and/or IgG2a (Bethyl Laboratories, Montgomery, Tex.) for 1 hr at 37° C. After four washes, the substrate 3,3',5,5'-tetramethylbenzidine (TMB) (Zymed) was added to the plates, and the reaction was stopped by adding 1 N $H_2SO_4$. The absorbance at 450 nm (A450) was measured by an ELISA plate reader (Tecan, San Jose, Calif.).

Figure 5:
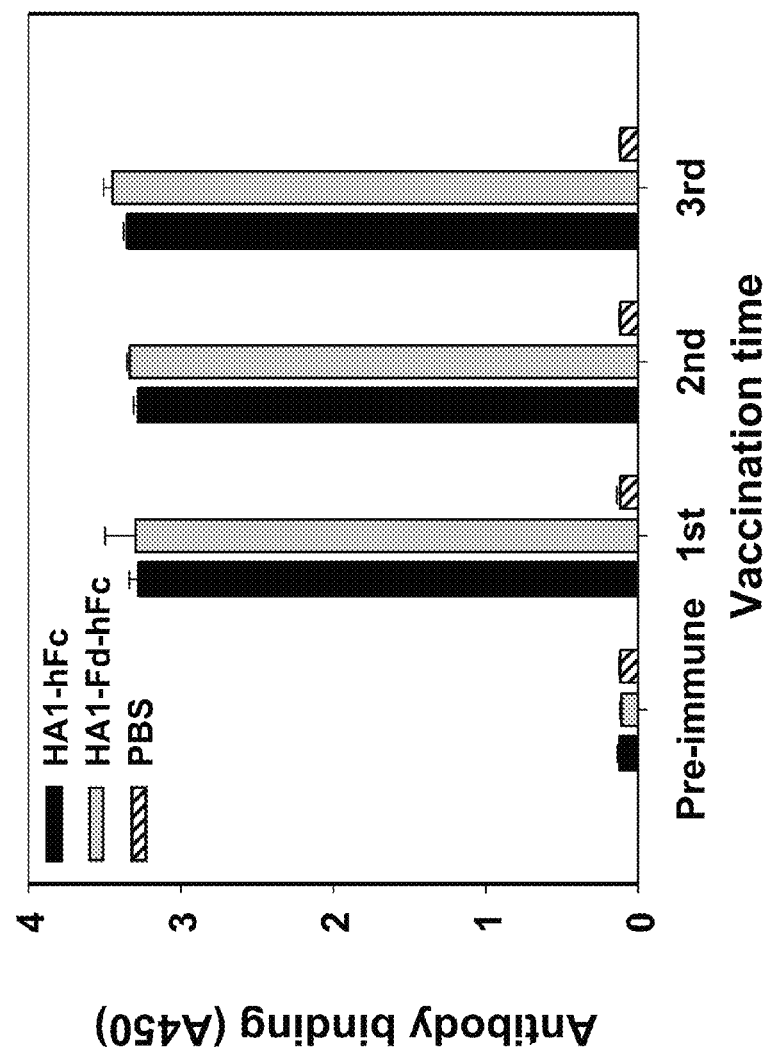
FIG. 5 depicts the binding reactivity of mouse sera (1:3,000 dilution) collected at day 0 (pre-immune) and 10 days post the $1^{st}$, $2^{nd}$ and $3^{rd}$ boosts with recombinant HA1-hFc and HA1-Fd-hFc proteins.
Figure 6:
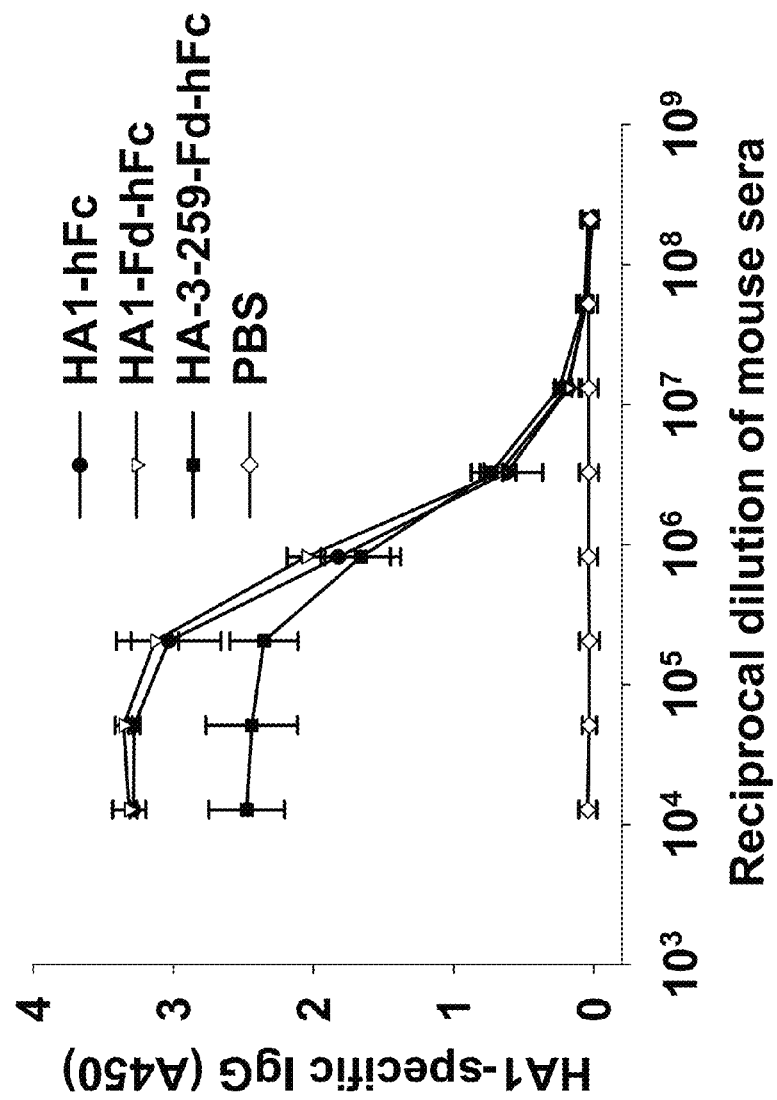
FIG. 6 depicts the ability of IgG antibody (Ab) to bind to HA1-hFc, HA1-Fd-hFc and HA-3-259-Fd-hFc fusion proteins detected in sera of mice collected 10 days post last vaccination with HA1-hFc, HA1-Fd-hFc and HA-3-259-Fd-hFc proteins.
Figure 7:
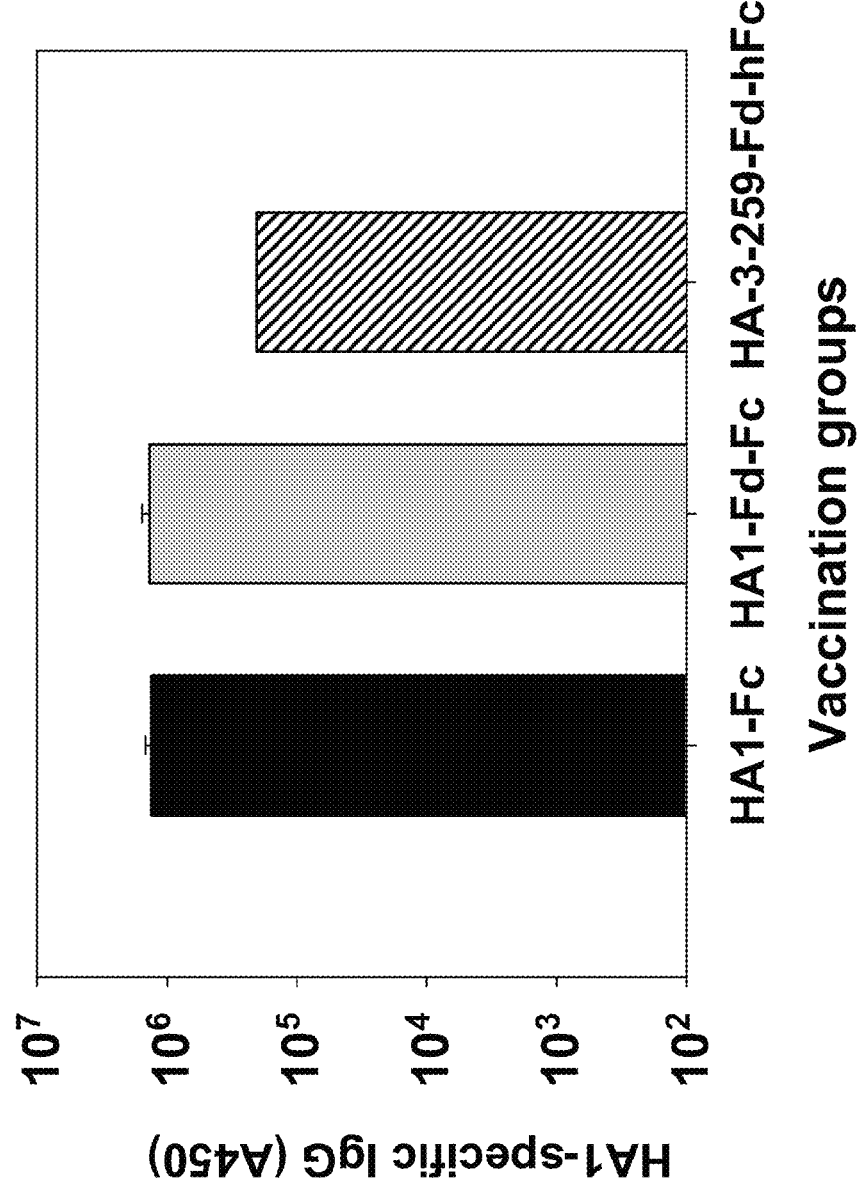
FIG. 7 depicts the mean anti-HA1-hFc, anti-HA1-Fd-hFc and anti-HA-3-259-Fd-hFc IgG Ab titer of mouse sera collected 10 days post last vaccination.

Antibody levels induced by HA1-hFc, HA1-Fd-hFc and HA-3-259-Fd-hFc proteins were detected by ELISA against HA fusion proteins. As shown in FIG. 5, both HA1-hFc and HA1-Fd-hFc proteins induced IgG antibody responses specific to the purified HA1-hFc and HA1-Fd-hFc proteins, quickly reaching a high level after the first boost vaccination, then slightly increasing antibody binding after each boost (sera were tested at a dilution of 1:3,000), while only background levels of antibody responses was detected in sera collected from prior immunization (pre-immune) and those from PBS control. An average end-point antibody titer of $1:2.1\times10^5$ was detected in mouse sera collected at 10 days post last boost (FIG. 6). The mean titer of the IgG antibodies in the sera, collected after the last boost, of the mice immunized with HA1-hFc, HA1-Fd-hFc and HA-3-259-Fd-hFc reached $1:3.9\times10^7\pm2.2\times10^7$, $1:1.5\times10^8\pm8.6\times10^7$, and $1:2.1\times10^5$, respectively (FIG. 7). The data in FIGS. 5-7 are expressed as Mean±Standard Deviation (SD).

Figure 8:
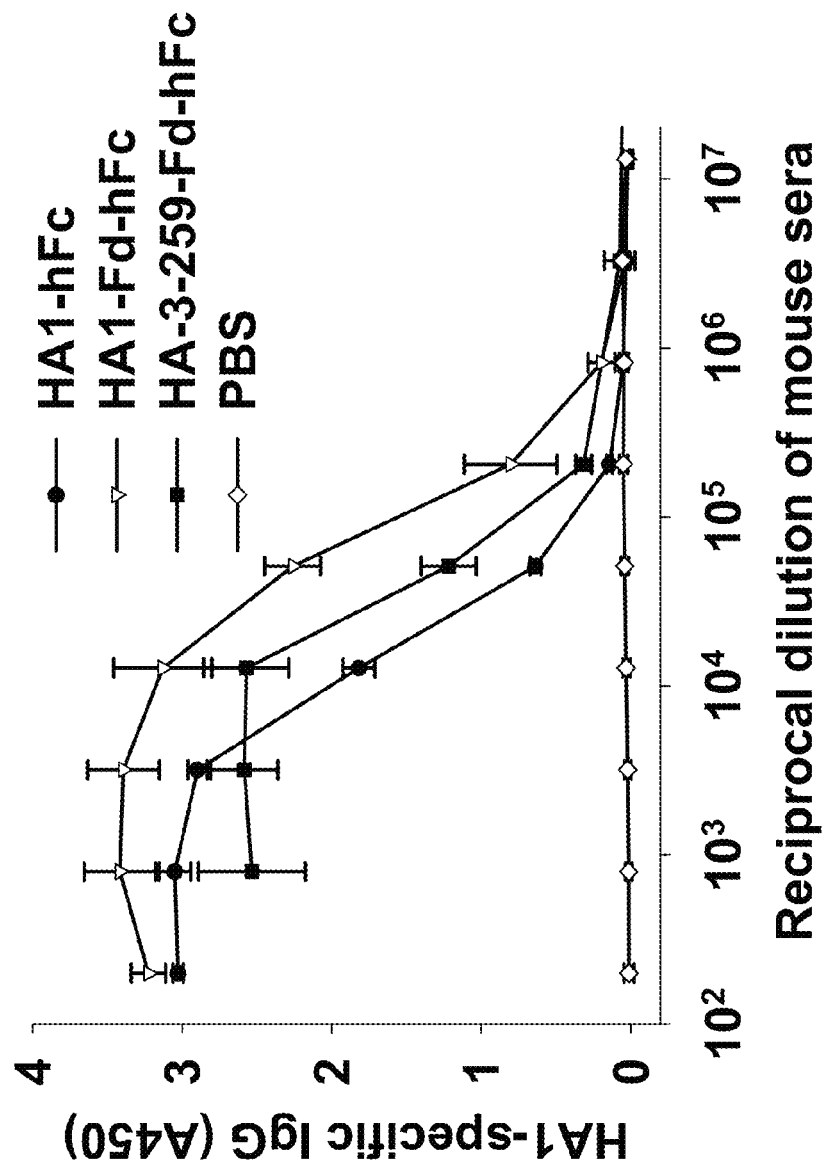
FIG. 8 depicts the ability of IgG Ab to bind to an HA1 protein without Fd and Fc, detected in serially diluted sera of mice collected 10 days post last vaccination with HA1-hFc, HA1-Fd-hFc and HA-3-259-Fd-hFc proteins.
Figure 9:
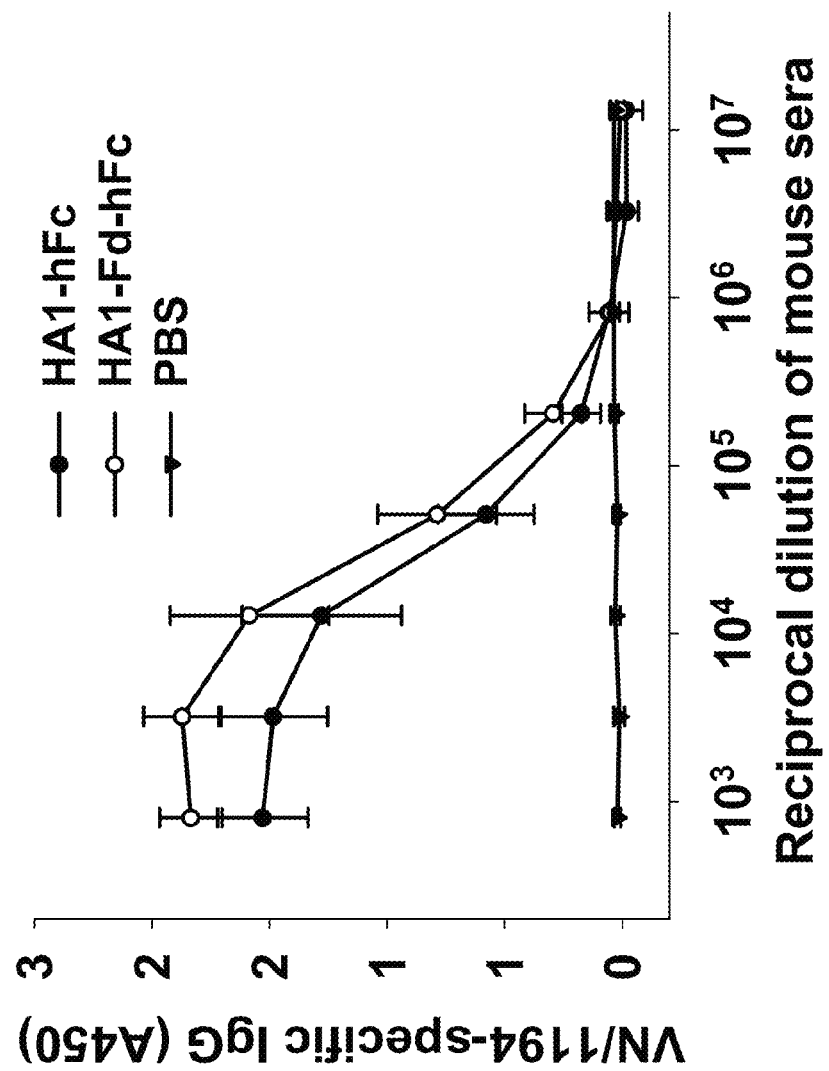
FIG. 9 depicts the ability of IgG Ab binds to A/VietNam/1194/2004 (VN/1194)-inactivated H5N1 virus, detected in serially diluted sera of mice collected 10 days post last vaccination with HA1-hFc, and HA1-Fd-hFc.

Antibody levels were further detected by ELISA against a HA1 protein without Fd and hFc to eliminate the antibody response potentially induced by the fusion tag Fd and/or hFc and, in addition against an inactivated heterologous H5N1 virus (VN/1194). As illustrated in FIG. 8, sera of mice vaccinated with these HA fusion proteins, particularly HA1-Fd-hFc, reacted strongly with HA1 proteins without Fd and/or Fc, reaching an end-point titer of $1:1.3\times10^7$, which suggests the high specificity of the antibody responses to the HA1 protein. It was further shown that the induced IgG antibodies could also react with an inactivated H5N1 virus (VN/1194), reaching a similar end-point titer of $1:1.3\times10^7$ (FIG. 9). However, no IgG antibody response was detectable in the sera of control mice injected with PBS (FIGS. 8 and 9).

Figure 10:
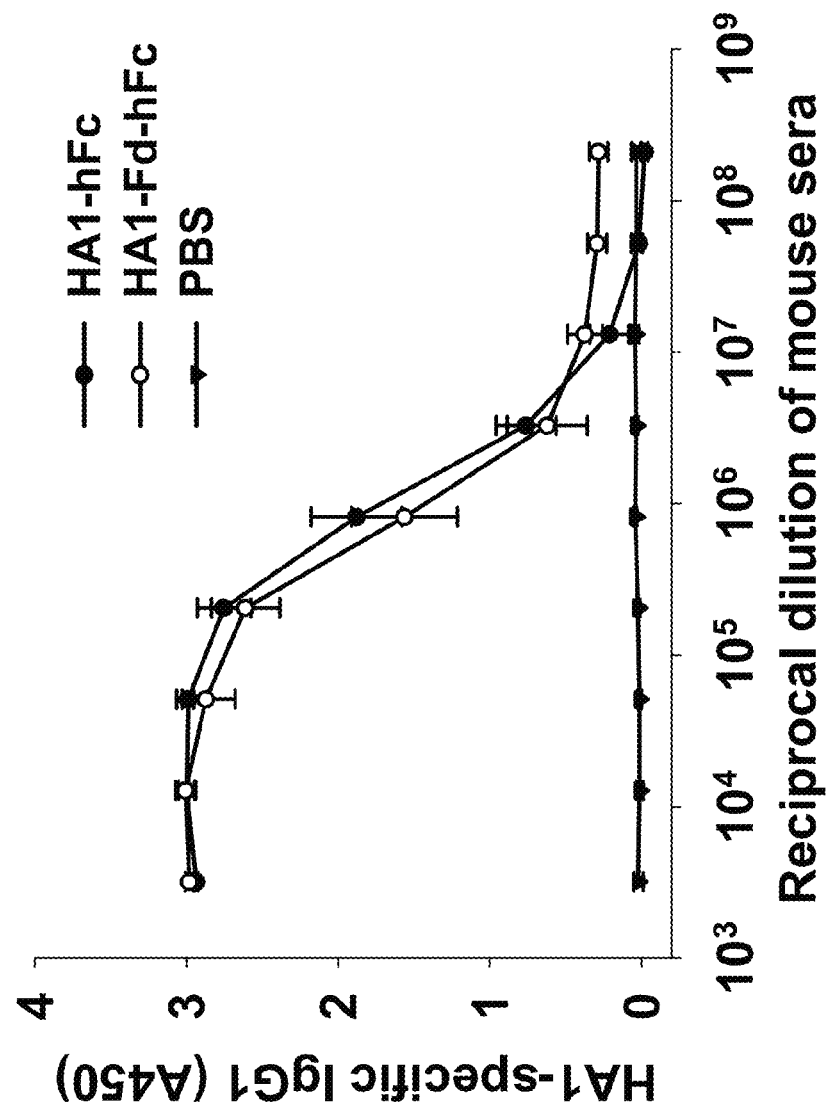
FIG. 10 depicts ability of IgG1 subtype Ab to bind to the HA1 protein, detected in serially diluted sera of mice collected 10 days post last vaccination with HA1-hFc, and HA1-Fd-hFc.
Figure 11:
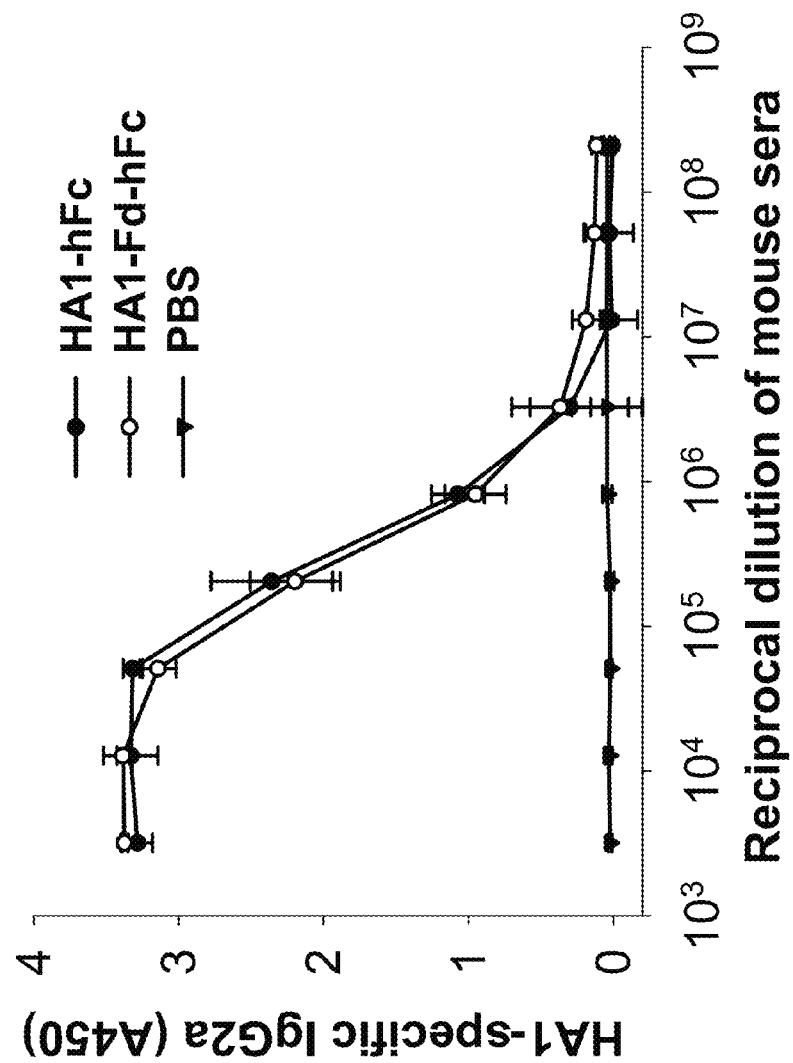
FIG. 11 depicts ability of IgG2a subtype Ab to bind to the HA1 protein, detected in serially diluted sera of mice collected 10 days post last vaccination with HA1-hFc, and HA1-Fd-hFc.
Figure 12:
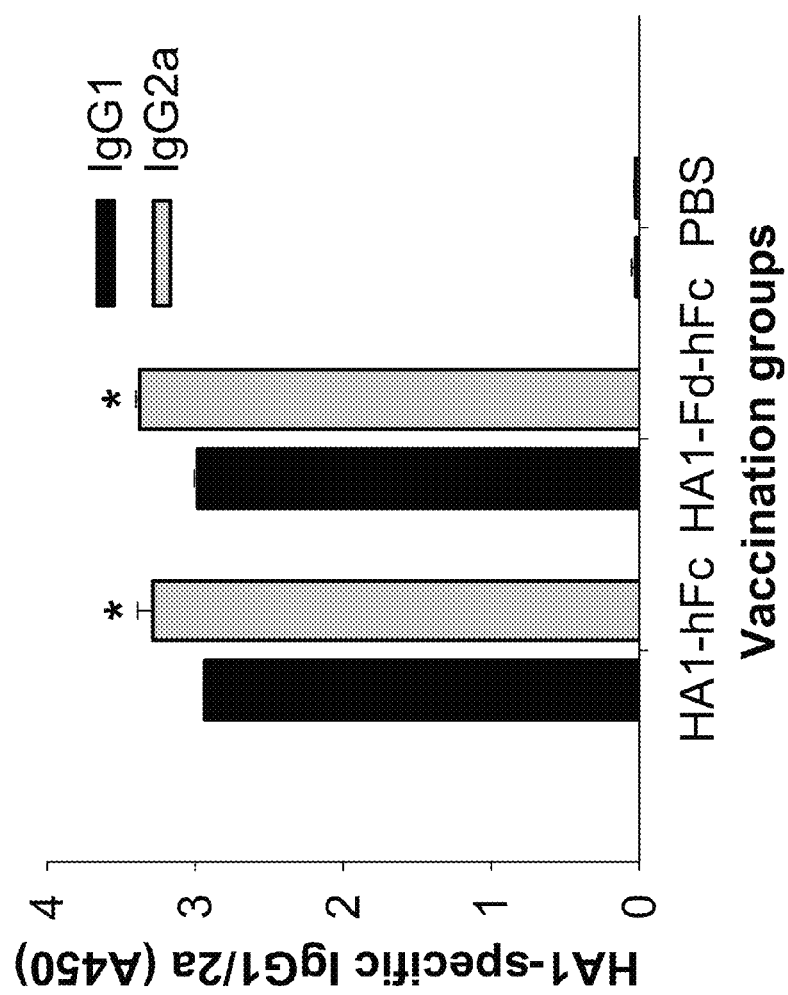
FIG. 12 depicts the comparison of IgG1 and IgG2a Ab responses in HA1-hFc- and HA1-Fd-hFc-vaccinated mice.

The evaluation of IgG subtypes induced by HA1-hFc and HA1-Fd-hFc proteins showed that IgG1 and IgG2a were detectable in the mouse sera collected at 10 days post last vaccination. Both HA1-hFc and HA1-Fd-hFc proteins elicited similar levels of IgG1 (Th2-associated, FIG. 10) and IgG2a (Th1-associated, FIG. 11) antibody responses specific to the HA1 proteins, reaching an end-point titer of $1:2.1\times10^8$. FIG. 12 further demonstrated that the IgG2a antibody titer was significantly higher than IgG1 ($P<0.05$), suggesting that both HA1-hFc and HA1-Fd-hFc fusion proteins have a tendency to stimulate Th1-associated antibody responses. However, no IgG1 or IgG2a antibody responses were found in sera of PBS control mice (FIGS. 10-12).

The above data suggest that expressed HA1-hFc, HA1-Fd-hFc and HA-3-259-Fd-hFc proteins are able to elicit high titers of antibody responses specific to the HA1 proteins of homogeneous and/or heterogeneous H5N1 viruses, implying their strong immunogenicity in stimulating highly potent humoral immune responses in the vaccinated mice. The data in FIGS. 8-12 are expressed as Mean±SD.

TABLE 2

Immunization scheme of recombinant HA fusion proteins for detection of antibody responses*

| Group | 1st immunization (Day 0) | Boost 1 (Day 21) | Boost 2 (Day 42) | Boost 3 (Day 63) |
|---|---|---|---|---|
| 12A (N = 3) 4 doses HA1-hFc | 20 μg protein in PBS + 100 μL SAS | 10 μg protein in PBS + 100 μL SAS | 10 μg protein in PBS + 100 μL SAS | 10 μg protein in PBS + 100 μL SAS |
| 12B (N = 5) | 20 μg protein in | 10 μg protein in | 10 μg protein in | 10 μg protein in |

TABLE 2-continued

Immunization scheme of recombinant HA fusion proteins for detection of antibody responses*

| Group | 1st immunization (Day 0) | Boost 1 (Day 21) | Boost 2 (Day 42) | Boost 3 (Day 63) |
|---|---|---|---|---|
| 4 doses HA1-Fd-hFc 12C (N = 5) | PBS + 100 μL SAS 20 μg protein in | PBS + 100 μL SAS 10 μg protein in | PBS + 100 μL SAS 10 μg protein in | PBS + 100 μL SAS 10 μg protein in |
| 4 doses HA336-89Fd-Fc 12D (N = 3) | PBS + 100 μL SAS 20 μg protein in | PBS + 100 μL SAS 10 μg protein in | PBS + 100 μL SAS 10 μg protein in | PBS + 100 μL SAS 10 μg protein in |
| 4 doses HA2-89Fc 12E (N = 4) | PBS + 100 μL SAS 20 μg protein in | PBS + 100 μL SAS 10 μg protein in | PBS + 100 μL SAS 10 μg protein in | PBS + 100 μL SAS 10 μg protein in |
| 4 doses HA2-89Fd-Fc 19C (N = 5) | PBS + 100 μL SAS 20 μg protein in | PBS + 100 μL SAS 10 μg protein in | PBS + 100 μL SAS 10 μg protein in | PBS + 100 μL SAS 10 μg protein in |
| 4 doses HA-3-259-Fd-hFc | PBS + 100 μL SAS | PBS + 100 μL SAS | PBS + 100 μL SAS | PBS + 100 μL SAS |

*All immunizations were in 200 μL total volume;
SAS = Sigma Adjuvant System (Sigma).
Blood samples were collected on day 0 (pre-immune) and 10 days after each boost for detection of antibody responses.

Example 3

Detection of Neutralizing Antibody Activity Induced by Recombinant HA Fusion Proteins Using H5N1 Pseudovirus Neutralization Assay The fusion proteins HA1-hFc and HA1-Fd-hFc were then evaluated for generation of neutralizing antibodies against highly pathogenic avian influenza (HPAI) H5N1 viruses based on a pseudotype neutralization assay. Sera were collected at pre-immunization and 10 days after each vaccination. Sera collected from Group12A (HA1-hFc), Group12B (HA1-Fd-hFc) and Group19C (HA-3-259-Fd-hFc) were tested for generation of neutralizing antibody activity against H5N1 pseudovirus expressing HAs of five isolates covering four clades, including the homologous strain A/Anhui/1/2005 (AH-HA, clade 2.3), and heterologous strains, such as A/Hong Kong/156/97 (HK-HA, clade 0), A/VietNam/1194/2004 (1194-HA, clade 1), A/Qinghai/59/05 (QH-HA, clade 2.2) and A/Xinjiang/1/2006 (XJ-HA, clade 2.2).

H5N1 Pseudovirus Production. The generation of H5N1 pseudovirus was done as previously described (Du L et al. Virology. 393:144-150, 2009; Du L et al. Biochem Biophys Res Commun 384:486-490, 2009; Du L et al. Biochem Biophys Res Commun 397:580-585, 2010) with some modifications. In brief, 293T cells were co-transfected with a plasmid encoding the HA of influenza A virus H5N1 isolates HK, 1194, QH, XJ, and AH, and a plasmid encoding the Env-defective, luciferase-expressing HIV-1 genome (pNL4-3.1uc.RE) using the calcium phosphate method. The medium, Dulbecco's Modified Eagle Medium (DMEM) containing 10% fetal bovine serum (FBS), was changed 10 hr later and neuraminidase (NA) (Sigma) was added to the culture medium 26 and 50 hr post-transfection at concentrations of 0.5-5 μg/ml. Supernatants were harvested 72 hr post-transfection and used for single-cycle infection of 293T cells.

Neutralizing antibody activity detected by H5N1 pseudovirus. In the detection of neutralizing activity of vaccinated mouse sera, all serum samples were heat-inactivated at 56° C. for 30 min and diluted in serial dilutions. An equal volume of samples and H5N1 pseudovirus were added to each well and incubated for 1 hr at 37° C. Then 100 μL of this mixture was added to each well of a 96-well tissue culture plate plated with 293T cells 6-8 hr previously. Twenty-four hours later, 80 μL/well of fresh DMEM containing 10% FBS was added to the wells and luciferase activity was detected 72 hr later. Cells were lysed using cell lysis buffer (Promega, Madison, Wis.). After addition of luciferase substrate (Promega), relative luciferase activity was determined in Ultra 384 luminometer (Tecan). The 50% neutralizing antibody titer ($NT_{50}$)) was calculated using Calcusyn program (Chou, T. C. Pharmacol Rev 58:621-681, 2006).

Figure 13:
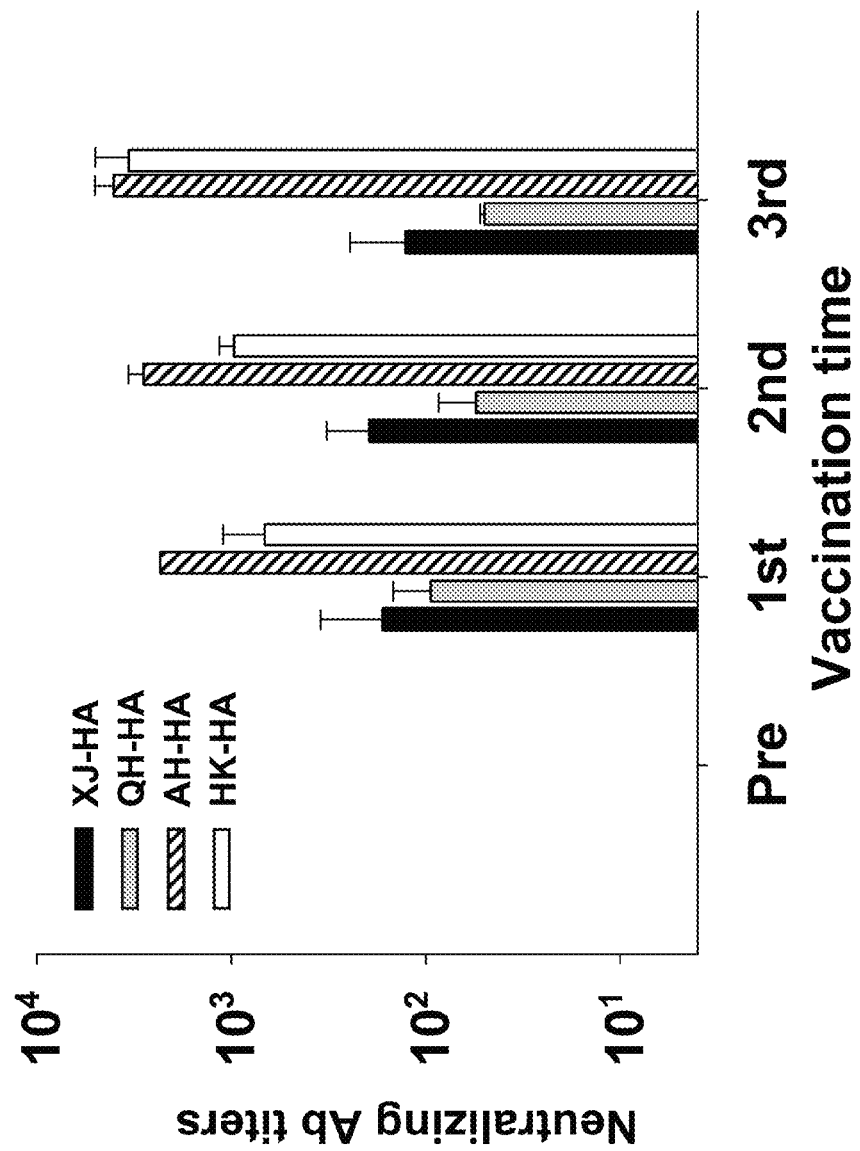
FIG. 13 depicts the neutralizing Ab titers ($NT_{50}$)) of sera from mice after each boost vaccination with HA1-hFc against H5N1 pseudovirus expressing XJ-HA, QH-HA, AH-HA and HK-HA as measured by pseudovirus neutralization assay.
Figure 14:
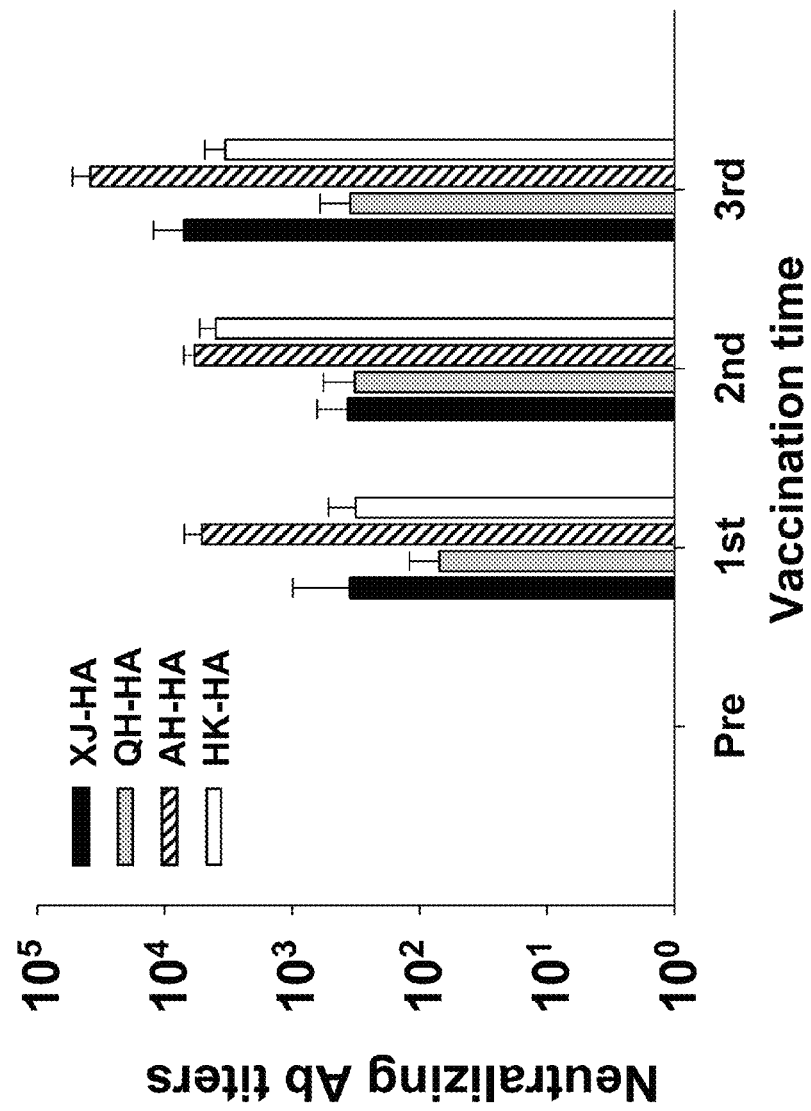
FIG. 14 depicts the neutralizing Ab titers ($NT_{50}$)) of sera from mice after each boost vaccination with HA1-Fd-hFc against H5N1 pseudovirus expressing XJ-HA, QH-HA, AH-HA and HK-HA as measured by pseudovirus neutralization assay.
Figure 15:
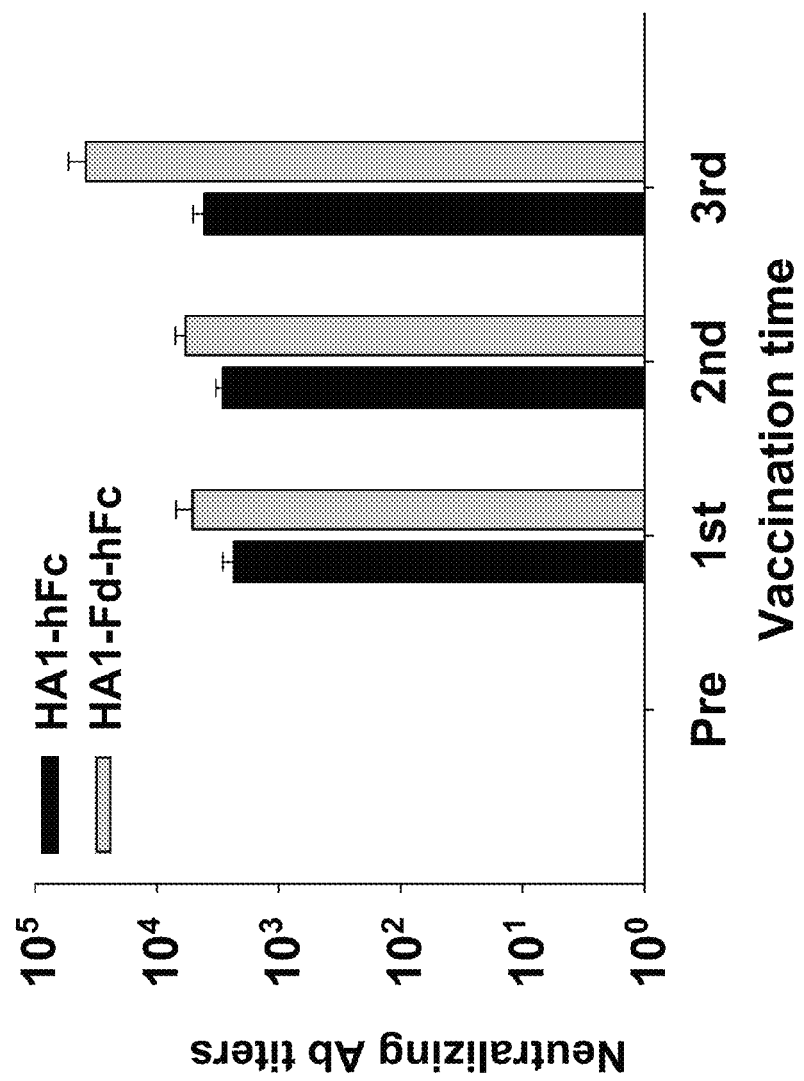
FIG. 15 depicts the neutralizing Ab titers ($NT_{50}$)) of sera from mice after each boost vaccination with HA1-hFc and HA1-Fd-hFc against H5N1 pseudovirus expressing homologous AH-HA as measured by pseudovirus neutralization assay.

The experimental results for the detection of neutralizing activity against H5N1 pseudovirus showed that these fusion proteins were able to induce highly potent specific IgG antibodies with neutralizing activity against H5N1 pseudovirus. Starting from 10 days post 1st boost vaccination, neutralizing antibodies were detected in mouse sera vaccinated with both HA1-hFc (FIG. 13) and HA1-Fd-hFc (FIG. 14). No, or low ($NT_{50}$) 1:50), levels of neutralizing antibodies were detected in pre-vaccinated mouse sera (FIGS. 13 and 14). Serum levels of these neutralizing antibodies increased rapidly at each time post-boost vaccination, reaching the highest level at 10 days post last vaccination (FIG. 15). The data in FIGS. 13-15 are expressed as Mean±SD.

Figure 17:
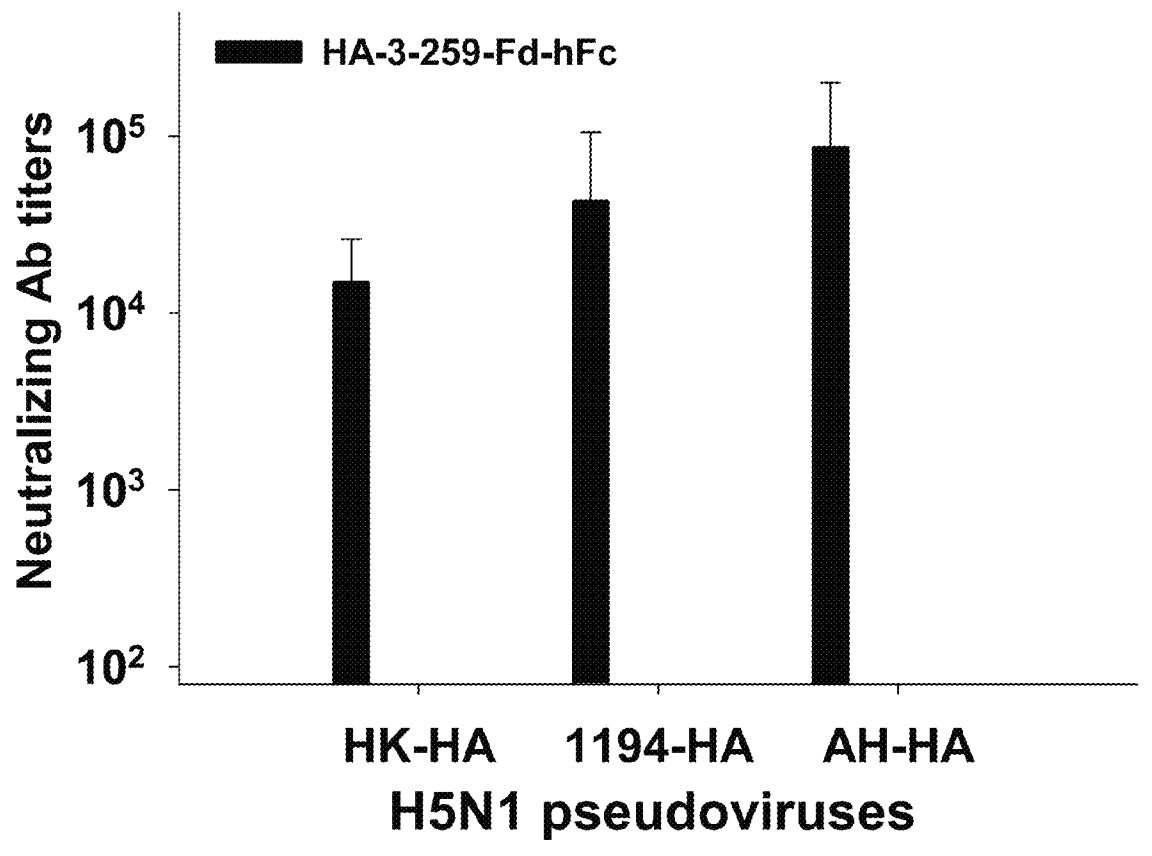

The above induced high titers of neutralizing antibodies could not only neutralize homologous strain of AH-HA (FIG. 15), but also neutralized heterologous HK-HA, 1194-HA, XJ-HA, and even QH-HA stains (FIGS. 13, 14, and 16), suggesting their potential ability in inducing cross-protection against divergent H5N1. In general, both proteins fused with Fc of hIgG1 (HA1-hFc and HA1-Fd-hFc) could induce potent neutralizing antibodies against H5N1 pseudovirus infection in 293T cells (FIGS. 14-16, Table 3), suggesting that IgG Fc may play a key role in the formation of oligomer structures of HA proteins and the enhancement of the immunogenicity of the fusion proteins. In addition, the HA1-Fd-hFc fusion protein with Fd sequences could induce higher titers of pseudovirus neutralizing antibodies than HA1-hFc protein without Fd, showing a significantly higher level of inhibition against infection by 1194-HA, QH-HA, XJ-HA and AH-HA H5N1 pseudoviruses (FIG. 16, P<0.05). The induction of high titers of neutralizing antibodies against infections of HK-HA, 1194-HA, and AH-HA H5N1 pseudoviruses were also detected in the sera of mice collected at 10 days post last vaccination of HA-3-259-Fd-hFc protein (FIG. 17), furthering confirming the importance of Fd sequences in the induction of highly potent neutralizing antibodies against divergent strains of H5N1 pseudoviruses. The Fd sequences may be helpful to form trimer structures of HA proteins, thus increasing neutralizing ability. The above results also suggest that in addition to the HA1 fragment containing residues +3-322, a shorter HA1 fragment of H5N1 covering residues +3-259 contains important neutralizing epitopes that induce highly potent neutralizing antibodies against multiple strains of H5N1 viruses. In contrast, the PBS control group only elicited a background level of neutralizing antibody titers against the tested H5N1 pseudoviruses (FIG. 16). The data in FIGS. 16 and 17 are expressed as Mean±SD.

TABLE 3

Pseudovirus neutralizing antibody titer ($NT_{50}$) in sera of mice vaccinated with HA fusion proteins*

| Influenza A virus H5N1 strain | $NT_{50}$ of sera of mice vaccinated with | |
|---|---|---|
| | HA1-hFc | HA1-Fd-hFc |
| HK-HA | 3,323 ± 1,677 | 3,353 ± 1,476 |
| 1194-HA | 443 ± 300 | 5,341 ± 1,475 |
| XJ-HA | 126 ± 119 | 6,963 ± 5,270 |
| QH-HA | 50 ± 3 | 350 ± 254 |
| AH-HA | 4,024 ± 996 | 38,177 ± 14,896 |

*Samples were from sera of mice collected at 10 days post last vaccination. The data are expressed as Mean ± SD of three to five mouse sera per group.

Example 4

Detection of Neutralizing Antibody Activity and Inhibition Induced by Recombinant HA Fusion Proteins Using H5N1 Live Virus Neutralization Assay and Hemagglutination Inhibition Assay The fusion proteins HA1-hFc and HA1-Fd-hFc were further evaluated for generation of neutralizing antibodies against highly pathogenic H5N1 viruses based on a live virus neutralization assay and hemagluttinin inhibition. Sera collected from Group12A (HA1-hFc) and Group12B (HA1-Fd-hFc) at 10 days post last vaccination were applied for detection of neutralizing antibody activity against H5N1 live viruses.

H5N1 virus neutralization assay. Titers of neutralizing antibodies of vaccinated mice were further detected by live neutralization assay. In brief, serial two-fold diluted mouse sera were mixed with 20 plaque forming units (PFU) of clade 0: A/Hong Kong/156/97 (HK/156), clade 1: A/Viet-Nam/1194/2004 (VN/1194) and clade 2.3.4: A/Shenzhen/406H/06 (SZ/406H) (H5N1) and incubated at 37° C. for 1 hr before adding to Madin-Darby canine kidney (MDCK) cells. Medium was replaced with fresh DMEM 1 hr later, and cell culture was continued for 72 hr at 37° C. The viral cytopathic effect (CPE) was observed daily and recorded on day 3 post-infection. The neutralizing antibody titer was determined based on the highest dilution of each serum, which completely suppressed CPE induced by the virus in >50% of the wells.

The hemagglutination inhibition (HI) assay. This assay was carried out as follows. In brief, serial dilutions of mouse sera at 10 days post last vaccination were incubated with equal volumes of HK/156, VN/1194 and/or SZ/406H H5N1 virus, for 1 hr at room temperature, followed by addition of equal volumes of 0.5% chicken red blood cells for 30 min at room temperature. The HI antibody titers were expressed as the highest serum dilution that completely inhibited hemagglutinating activity.

Figure 18:
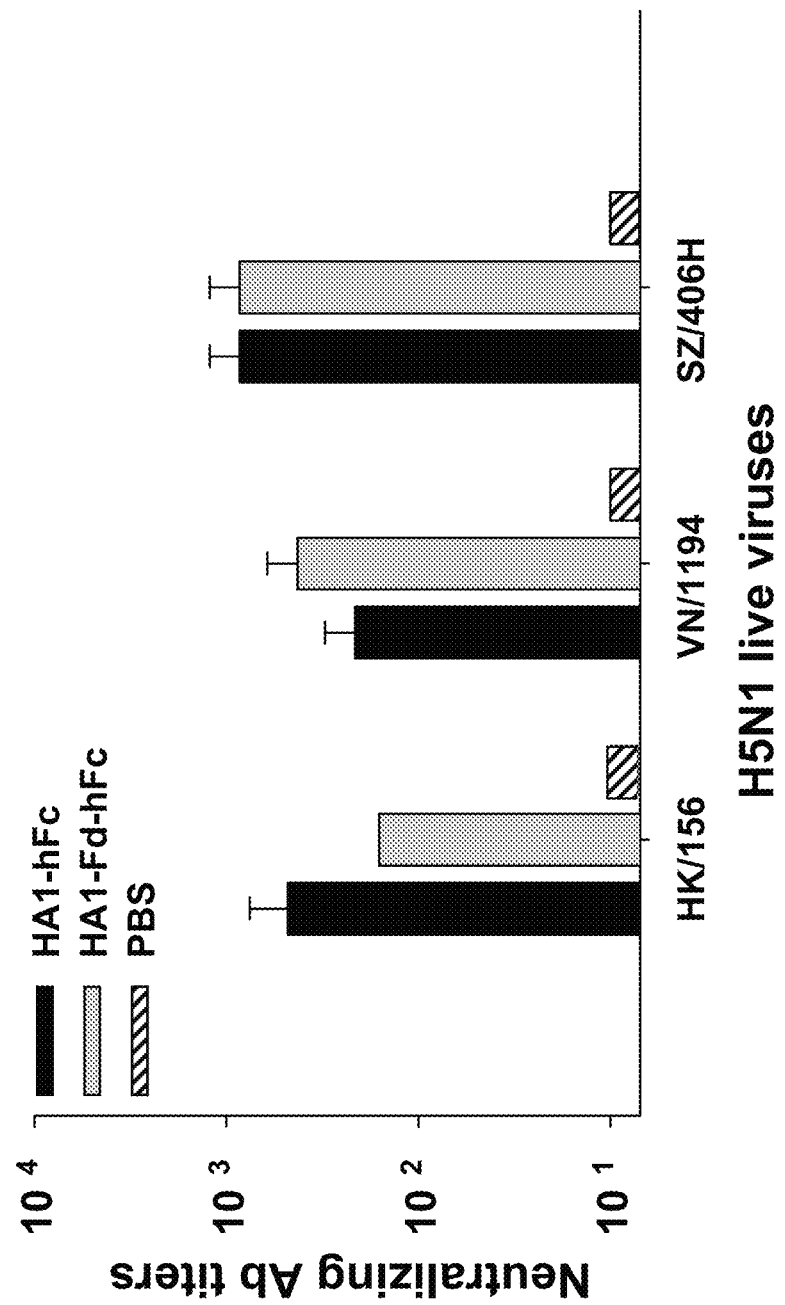
FIG. 18 depicts the neutralizing Ab titers ($NT_{50}$)) against heterologous strains A/Hong Kong/156/97 (HK/156), VN/1194 and A/Shenzhen/406H/06 (SZ/406H) of H5N1 live virus, detected in sera of mice at 10 days post last vaccination with HA1-hFc, and HA1-Fd-hFc.
Figure 19:
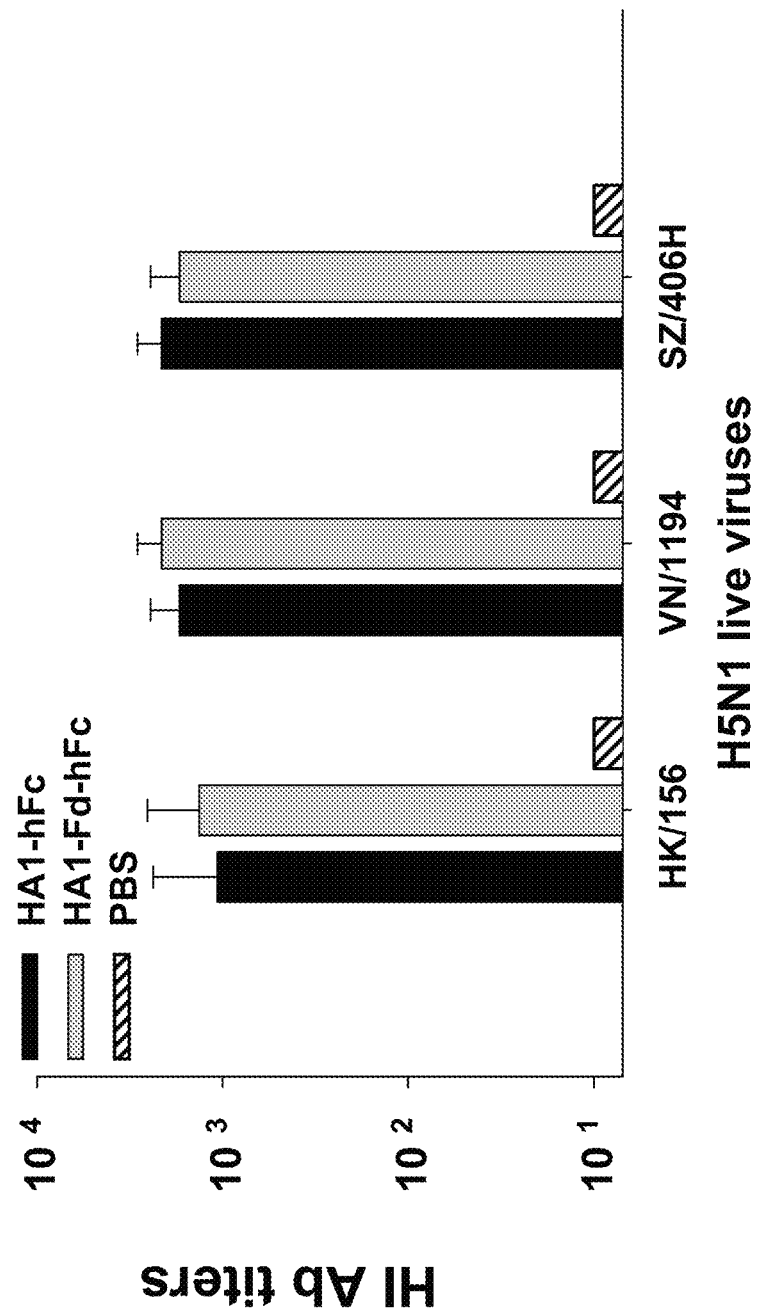
FIG. 19 depicts the hemagglutination inhibition (HI) antibody titers against heterologous strains (HK/156, VN/1194 and SZ/406H) of H5N1 live virus, detected in sera of mice at 10 days post last vaccination with HA1-hFc, and HA1-Fd-hFc.

The experimental results for the detection of neutralizing activity against H5N1 live virus showed that the induced antibodies could neutralize infections of at least three heterologous strains covering three clades of H5N1 live viruses, such as HK/156 (clade 0), VN/1194 (clade 1) and SZ/406H (clade 2.3.4) (FIG. 18). In addition, the antibodies were able to inhibit the hemagglutination of these three H5N1 live viruses, with the average HI titer $1:1.0\times10^3$ (FIG. 19). Notably, the neutralizing antibodies induced by HA1-Fd-hFc were generally greater than those induced by HA1-hFc. In contrast, the PBS control group only elicited a background level of neutralizing and HI antibody titers in the tested H5N1 live viruses (FIGS. 18 and 19). The data in FIGS. 18 and 19 are expressed as Mean±SD.

Example 5

H5N1 Virus Challenge and Cross-Protection Evaluation Induced by Recombinant HA Fusion Proteins Against Divergent Strains of H5N1 Virus The fusion proteins HA1-hFc and HA1-Fd-hFc were then evaluated for inducing cross-protective immunity against highly pathogenic H5N1 viruses by observation of the survival rate of animals after H5N1 virus challenge, and detection of the viral load and histopathological changes in lung tissues collected from the mice at day 5 post-virus challenge.

H5N1 live virus challenge and sample collection. BALB/c female mice, 6-8 weeks old, were kept in biosafety level-3 (BSL-3) housing and given access to standard pellet feed and water ad libitum. All experimental protocols followed the standard operating procedures of the approved BSL-3 animal facilities and were approved by the Animal Ethics Committee. Mice (45 mice/group) were subcutaneously (s.c.) primed-vaccinated with 20 µg/mouse of purified HA1-hFc or HA1-Fd-hFc resuspended in PBS in the presence of SAS and boosted twice with 10 µg/mouse of immunogen containing SAS at 3-week intervals. Control mice were s.c. injected with the same volume of PBS-SAS. Mice were challenged intranasally (i.n.) with 10 $LD_{50}$ (50% Lethal Dose) of one of three clades of H5N1 virus, i.e., clade 0: HK/156, clade 1: VN/1194, and clade 2.3.4: SZ/406H, respectively (15 mice/group), at 10-12 days after the last vaccination. Infected mice were observed daily for 21 days or until the death of the mice for the survival rate detection. Five mice/group were sacrificed on day 5 post-challenge, and lung samples were collected for virological and histopathological detection. The immunization and virus challenge scheme is described in Table 4 and FIG. 4.

TABLE 4

Immunization scheme of recombinant HA fusion proteins for detection of cross-protective immunity

| Group | Vaccine Dosage | Virus challenge 10-12 days post last vaccine | | | Lung tissues 5 days post-challenge | Observe two weeks post-challenge |
|---|---|---|---|---|---|---|
| 1A (N = 45) 3 doses HA1-hFc | Vaccine as Table 2 3 doses | A/Hong Kong/156/97 (15mice) | A/Vietnam/ 1194/04 (15mice) | A/Shenzhen/ 406H/06 (15mice) | 5 mice/group for viral load and histopathology analysis | 10 mice/group for survival rate |
| 1B (N = 45) 3 doses HA1-Fd-hFc | Vaccine as Table 2 3 doses | A/Hong Kong/156/97 (15mice) | A/Vietnam/ 1194/04 (15mice) | A/Shenzhen/ 406H/06 (15mice) | | 10 mice/group for survival rate |
| 1C (N = 45) 3 doses PBS | Vaccine as Table 2 3 doses | A/Hong Kong/156/97 (15mice) | A/Vietnam/ 1194/04 (15mice) | A/Shenzhen/ 406H/06 (15mice) | | 10 mice/group for survival rate |

Virological tests. Viral RNA in lung tissues was quantified by Q-RT-PCR as previously described (Zheng B J et al. Proc Natl Acad Sci USA 105:8091-8096. 2008). In brief, total RNA in lysed lung tissues was extracted by using RNeasy Mini kit (Qiagen, Valencia, Calif.) and reverse transcribed to cDNA by using applied SuperScript II Reverse Transcriptase (Invitrogen). Viral cDNA was synthesized by Superscript RT II (Invitrogen) using Uni12 primer (AGCAAAAGC; SEQ ID NO:42). Real-time PCR was performed on the LightCycler 480 system (Roche Applied Sciences) using SYBR Green I Master (Roche) with gene-specific primer pairs (for HK/156, forward primer: 5'-TGTCAAGAAAGGA-GACTCAGC-3' [SEQ ID NO:43], reverse primer: 5'-AC-CATCTACCATTCCCTGC-3' [SEQ ID NO:44]; for VN/1194, forward primer: 5'-ATACACCCTCTCAC-CATCGG-3' [SEQ ID NO:45], reverse primer: 5'-ACCATC-TACCATTCCCTGCC-3' [SEQ ID NO:46]; for SZ/406H, forward primer: 5'-ATACACCCTCTCACCATCGG-3' [SEQ ID NO:47], reverse primer: 5'-ACCATCTACCATTC-CCTGC-3' [SEQ ID NO:48]) targeting the H1 gene of different strains of H5N1 virus. The pcDNA3.1 plasmid, which contains the cloned H1 gene of the virus, was used as the standard.

Histopathological analysis. The lung tissues of challenged mice were immediately fixed in 10% buffered formalin and embedded in paraffin wax. Sections 4-6 µm in thickness were made and mounted on slides. Histopathological changes caused by H5N1 virus infection were examined by H&E staining and viewed under a light microscope as previously described (Du L et al. J Immunol 180:948-956. 2008; Zheng B J et al. Proc Natl Acad Sci USA 105:8091-8096. 2008).

Figure 20:
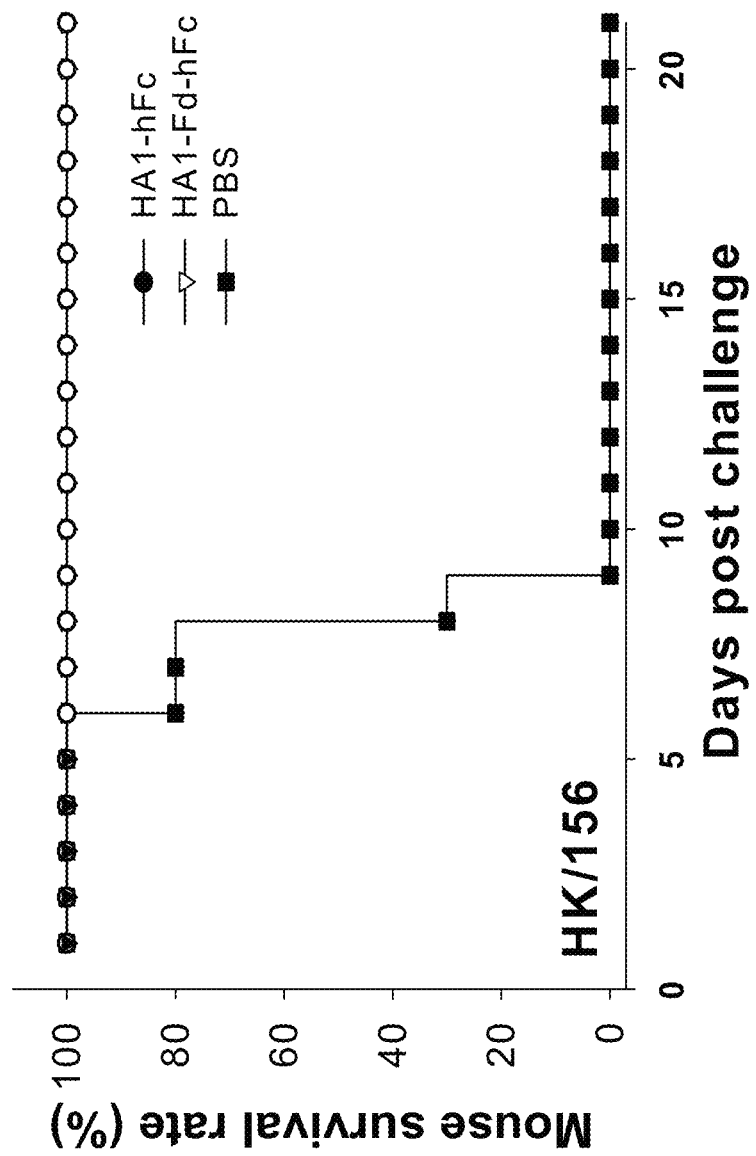
FIG. 20 depicts the cross-protection of HA1-hFc- and HA1-Fd-hFc-vaccinated mice against lethal H5N1 virus challenge, indicated by survival rate (%) of mice challenged with HK/156 strain (clade 0) of H5N1 live virus.
Figure 21:
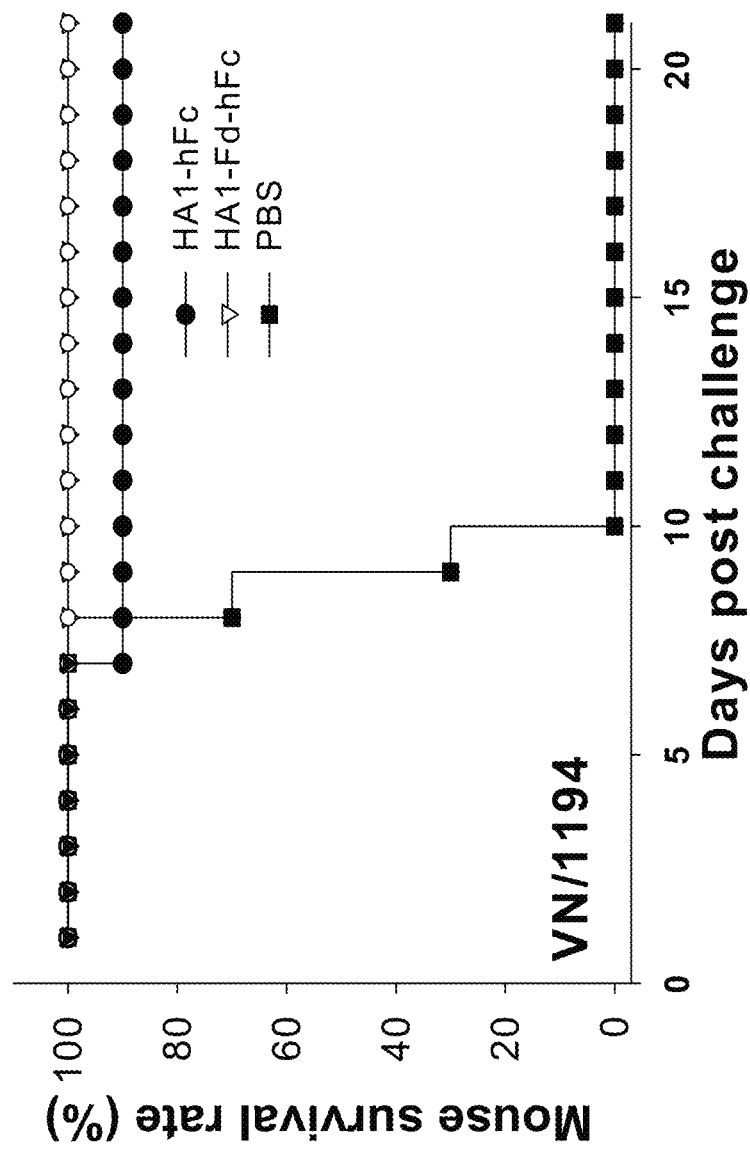
FIG. 21 depicts the cross-protection of HA1-hFc- and HA1-Fd-hFc-vaccinated mice against lethal H5N1 virus challenge, indicated by survival rate (%) of mice challenged with VN/1194 strain (clade 1) of H5N1 live virus.
Figure 22:
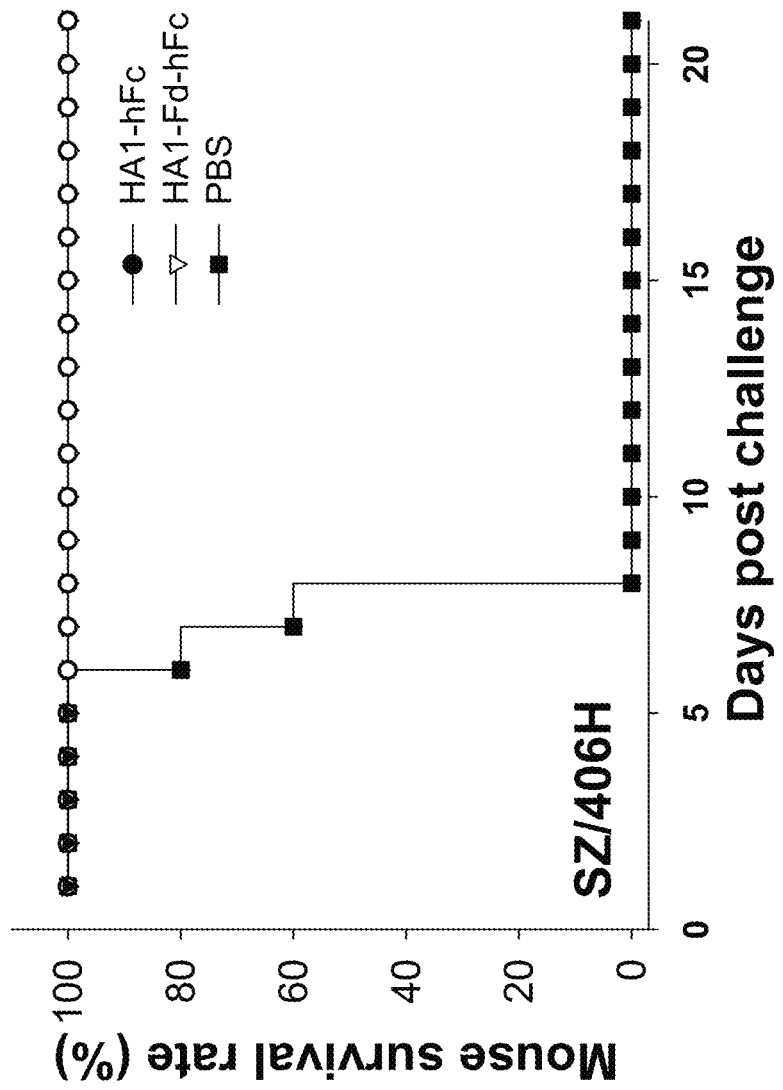
FIG. 22 depicts the cross-protection of HA1-hFc- and HA1-Fd-hFc-vaccinated mice against lethal H5N1 virus challenge, indicated by survival rate (%) of mice challenged with SZ/406H strain (clade 2.3.4) of H5N1 live virus.

The experimental results for the evaluation of cross-protection induced by recombinant HA fusion proteins against H5N1 live virus showed that all vaccinated mice survived challenge with HK/156 (clade 0, FIG. 20) and SZ/406H (clade 2.3.4, FIG. 22), suggesting that these two proteins may completely protect mice against challenges with different clades of H5N1 virus. All mice vaccinated with HA1-Fd-hFc also survived challenge with VN/1194 (clade 1), whereas about 10% of HA1-hFc-vaccinated mice did not survive challenge with this virus (FIG. 21). In contrast, no control mice injected with PBS survived the challenge with HK/156, VN/1194 and SZ/406H H5N1 viruses (FIGS. 20-22). These results demonstrated that vaccination with these fusion proteins, particularly HA1-Fd-hFc, could provide cross-clade protection against divergent strains of H5N1 virus infection.

Figure 23:
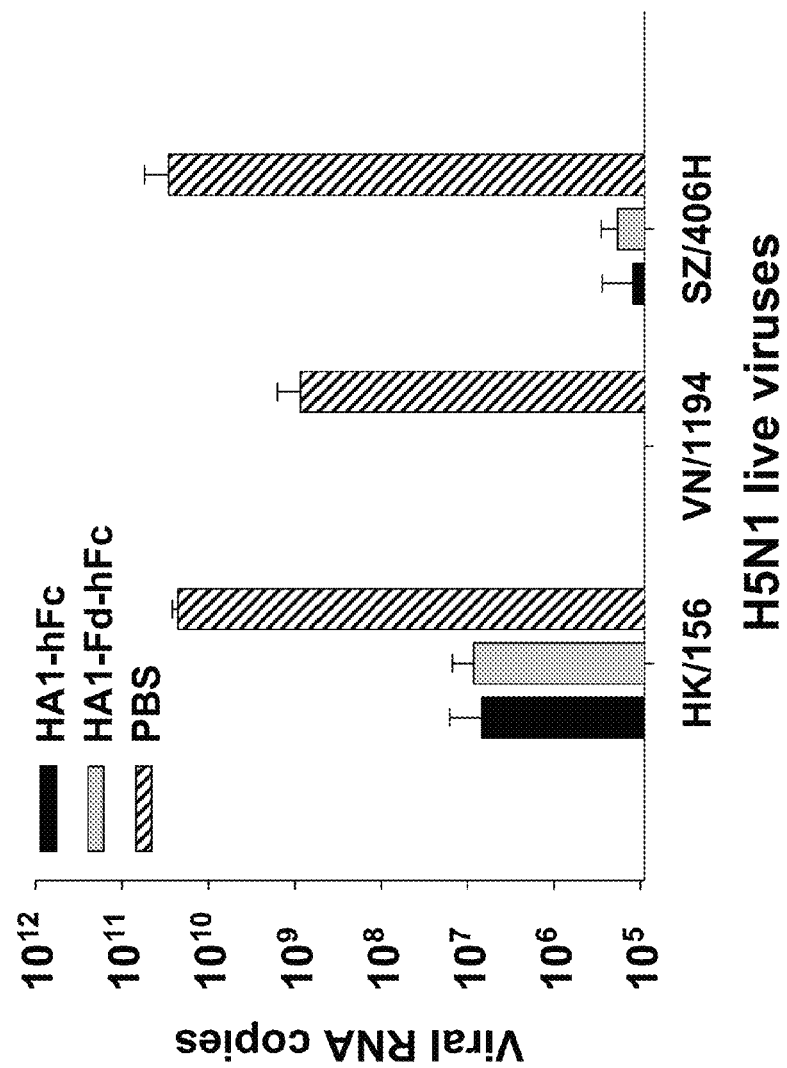
FIG. 23 depicts the quantification of viral RNA in lung tissue of H5N1 virus-challenged mice by quantitative reverse transcription PCR (QRT-PCR). Viral titers of HK/156, VN/1194 and SZ/406H strains of H5N1 virus were determined in lung tissues of the mice vaccinated with HA1-hFc and HA1-Fd-hFc proteins.

The experimental results for the evaluation of cross-protection induced by recombinant HA fusion proteins against H5N1 live virus also demonstrated that viral RNA was undetectable in the HA1-hFc- and HA1-Fd-hFc-vaccinated mice challenged with VN/1194 virus, but a high level of viral RNA ($8.6 \times 10^8$ copies) was detected in the control mice injected with PBS. Lung tissues of mice vaccinated with HA1-hFc and HA1-Fd-hFc also exhibited significantly lower levels of viral RNA than the PBS control group after challenge with HK/156 and SZ/406H virus, respectively ($P<0.05$) (FIG. 23). The data in FIG. 23 are expressed as Mean±SD.

Figure 24:
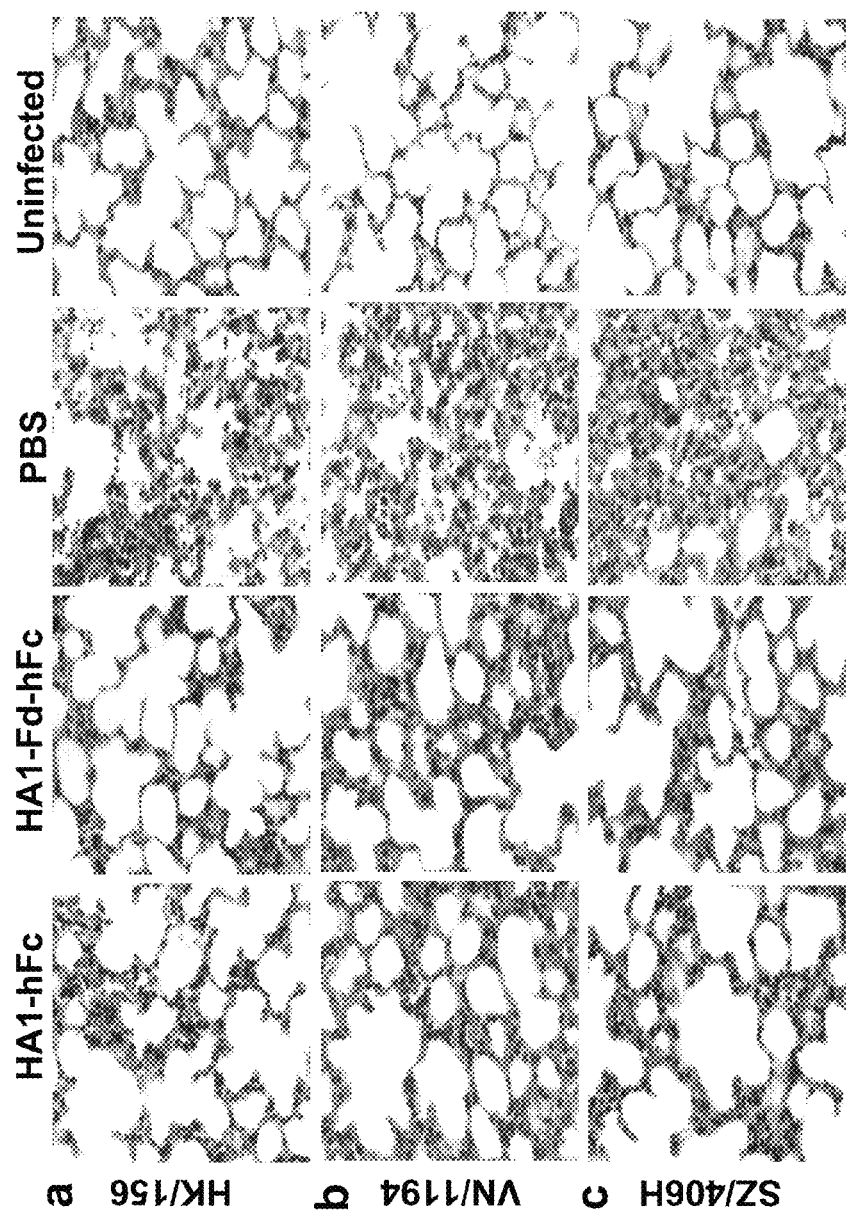
FIG. 24 depicts the evaluation of histopathological changes in the lung tissues of HA1-hFc- and HA1-Fd-hFc-vaccinated mice following lethal challenge with heterologous strains of H5N1 virus. Lung tissues from mice injected with PBS and those of uninfected mice were used as negative and normal controls, respectively. All sections of lung tissues were stained with hematoxylin and eosin (H&E) and observed under a light microscope (magnification, 100×). Representative images of histopathological damage from vaccinated mice challenged with H5N1 strains HK/156 (a), VN/1194 (b), and SZ/406H (c) are depicted.

Examination of the H&E-stained lung tissues from virus-challenged mice revealed that all of the control mice injected with PBS developed a high degree of histopathological damage, including serious interstitial pneumonia and significant inflammation, which were characterized by predominant lymphocyte infiltration, epithelial cell degeneration, broadened interstitial spaces, pulmonary vascular dilatation and congestion, and focal hemorrhage and exudation. In contrast, mice receiving HA1-hFc and HA1-Fd-hFc vaccination neither developed significant pulmonary injury nor severe inflammation after challenge with all three H5N1 viruses covering different clades, showing lung structures similar to those of normal mice (FIG. 24). These results suggest that the immunity induced by the recombinant HA fusion proteins is able to highly suppress virus replication in vaccinated mouse lungs, indicating that vaccinations of HA1-hFc and HA1-Fd-hFc proteins reduced virus replication and limited lung damage in the mice infected by divergent strains of H5N1 virus.

The above results indicate the potential of the above tested candidate influenza vaccine in developing into a universal flu vaccine against divergent influenza viruses, suggesting its ability in prevention of future flu outbreak.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible.

Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

---

What is claimed is:

1. A method of inducing a protective immune response against an influenza virus comprising:

administering an immunogenic composition to a host in need thereof, wherein the immunogenic composition comprises a fusion polypeptide comprising:

an immunogen sequence selected from the group consisting of: an influenza virus hemagglutinin, an influenza virus neuraminidase, or an influenza virus membrane protein (M);

an immunopotentiator sequence comprising the Fc fragment of human IgG or a muramyl peptide; and a foldon stabilization sequence;

wherein the immunogenic composition induces a protective immune response against challenge with infectious influenza virus in the host.

2. The method according to claim 1, wherein the immunogenic composition further comprises an adjuvant.

3. The method according to claim 1, wherein the immunogen sequence is a hemagglutinin sequence of an influenza virus.

4. The method according to claim 1, wherein the immunogen sequence is a neuraminidase sequence of an influenza virus.

5. The method according to claim 1, wherein the immunogen sequence is a membrane protein (M) sequence of the influenza virus.

6. The method according to claim 1, wherein said polypeptide is produced in a mammalian expression system.

7. The method according to claim 3, wherein the hemagglutinin sequence is a fragment of a hemagglutinin sequence selected from the group consisting of HA1, HA2 and RBD.

8. The method according to claim 1, wherein the fusion polypeptide is selected from the group consisting of HA1-Fd-hFc, HA-Fd-hFc, HA2-Fd-hFc, HA-RBD-Fd-hFc, and HA1+3-259-Fd-hFc.

* * * * *